(12) United States Patent
Kato et al.

(10) Patent No.: US 9,634,255 B2
(45) Date of Patent: Apr. 25, 2017

(54) AROMATIC AMINE DERIVATIVE AND ORGANIC ELECTROLUMINESCENCE ELEMENT USING SAME

(75) Inventors: Tomoki Kato, Chiba (JP); Takahiro Fujiyama, Chiba (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 463 days.

(21) Appl. No.: 14/345,066

(22) PCT Filed: Sep. 11, 2012

(86) PCT No.: PCT/JP2012/073224
§ 371 (c)(1),
(2), (4) Date: Jul. 1, 2014

(87) PCT Pub. No.: WO2013/039073
PCT Pub. Date: Mar. 21, 2013

(65) Prior Publication Data
US 2014/0374720 A1 Dec. 25, 2014

(30) Foreign Application Priority Data
Sep. 15, 2011 (JP) ................................ 2011-202389

(51) Int. Cl.
*H01L 51/50* (2006.01)
*H01L 51/00* (2006.01)
(Continued)

(52) U.S. Cl.
CPC ........ *H01L 51/0058* (2013.01); *C07D 209/86* (2013.01); *C07D 271/107* (2013.01);
(Continued)

(58) Field of Classification Search
None
See application file for complete search history.

(56) References Cited

U.S. PATENT DOCUMENTS

2004/0265630 A1* 12/2004 Suh .................... H01L 51/5052
428/690
2009/0066235 A1    3/2009 Yabunouchi et al.
(Continued)

FOREIGN PATENT DOCUMENTS

JP    2005-112765 A    4/2005
JP    3695714          9/2005
(Continued)

OTHER PUBLICATIONS

International Search Report Issued Oct. 9, 2012 in PCT/JP12/073224 Filed Sep. 11, 2012.
(Continued)

*Primary Examiner* — Gregory Clark
(74) *Attorney, Agent, or Firm* — Oblon, McClelland, Maier & Neustadt, L.L.P.

(57) ABSTRACT

An aromatic amine derivative represented by formula (1):

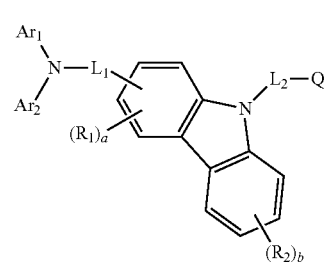

(1)

wherein $L_1$, $L_2$, $Ar_1$, $Ar_2$, $R_1$, $R_2$, a, b, and Q are as defined in the specification. An organic electroluminescence device (Continued)

having at least one organic thin film layer which includes the aromatic amine derivative has high emission efficiency and long lifetime.

18 Claims, 1 Drawing Sheet

(51) Int. Cl.
*C09K 11/06* (2006.01)
*H05B 33/14* (2006.01)
*C07D 405/14* (2006.01)
*C07D 403/10* (2006.01)
*C07D 405/04* (2006.01)
*C07D 405/10* (2006.01)
*C07D 409/04* (2006.01)
*C07D 409/14* (2006.01)
*C07D 271/107* (2006.01)
*C07D 209/86* (2006.01)
*H01L 51/52* (2006.01)
*C07D 471/14* (2006.01)
*C09B 57/00* (2006.01)

(52) U.S. Cl.
CPC ......... *C07D 403/10* (2013.01); *C07D 405/04* (2013.01); *C07D 405/10* (2013.01); *C07D 405/14* (2013.01); *C07D 409/04* (2013.01); *C07D 409/14* (2013.01); *C07D 471/14* (2013.01); *C09B 57/00* (2013.01); *C09B 57/008* (2013.01); *C09K 11/06* (2013.01); *H01L 51/006* (2013.01); *H01L 51/0052* (2013.01); *H01L 51/0061* (2013.01); *H01L 51/0072* (2013.01); *H01L 51/0073* (2013.01); *H01L 51/0074* (2013.01); *H01L 51/52* (2013.01); *H05B 33/14* (2013.01); *C09K 2211/1074* (2013.01); *H01L 51/0059* (2013.01); *H01L 51/0085* (2013.01); *H01L 51/5016* (2013.01); *H01L 51/5068* (2013.01)

(56) References Cited

U.S. PATENT DOCUMENTS

| | | | |
|---|---|---|---|
| 2009/0066239 A1* | 3/2009 | Yabunouchi | C07C 211/58 313/504 |
| 2009/0096360 A1 | 4/2009 | Tanaka et al. | |
| 2011/0017983 A1 | 1/2011 | Mizuki et al. | |

FOREIGN PATENT DOCUMENTS

| | | | | |
|---|---|---|---|---|
| JP | 2008 78362 | | 4/2008 | |
| JP | 2008 195841 | | 8/2008 | |
| JP | 2009 267257 | | 11/2009 | |
| KR | 10 2010 0033265 | | 3/2010 | |
| KR | 10 2011 0079402 | | 7/2011 | |
| WO | WO 2007/004384 | * | 4/2007 | ........... C07D 209/88 |
| WO | WO 2007/043484 A1 | | 4/2007 | |
| WO | 2007 077810 | | 7/2007 | |
| WO | 2009 020095 | | 2/2009 | |
| WO | 2009 060780 | | 5/2009 | |
| WO | 2009 104488 | | 8/2009 | |
| WO | 2009 110360 | | 9/2009 | |
| WO | 2010 044342 | | 4/2010 | |
| WO | 2011 040607 | | 4/2011 | |
| WO | 2011 093220 | | 8/2011 | |

OTHER PUBLICATIONS

Office Action issued Nov. 4, 2015 in Japanese Patent Application No. 2012-200412.

\* cited by examiner

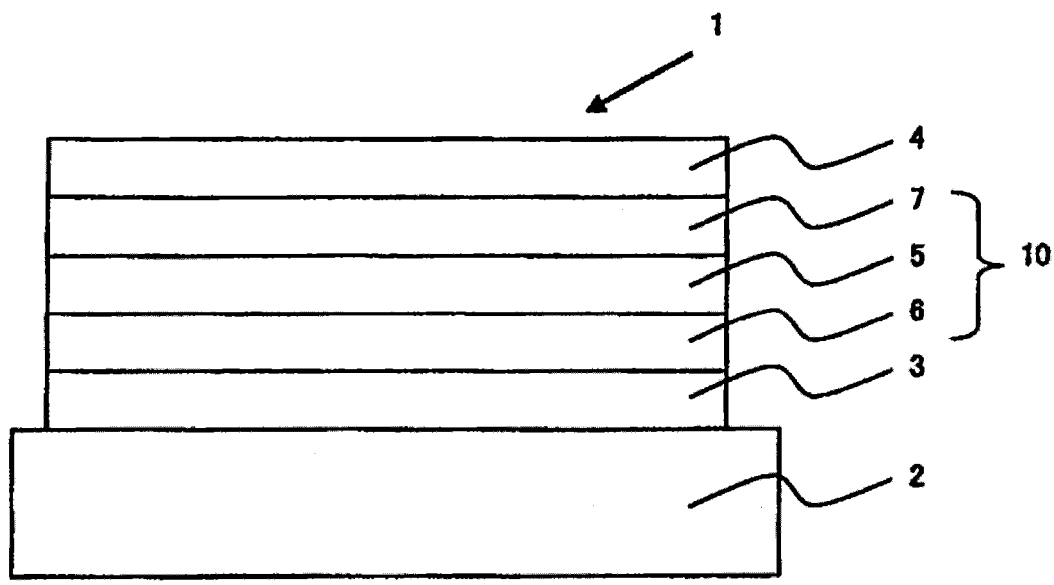

AROMATIC AMINE DERIVATIVE AND ORGANIC ELECTROLUMINESCENCE ELEMENT USING SAME

TECHNICAL FIELD

The present invention relates to aromatic amine derivatives and organic electroluminescence devices (hereinafter also referred to as organic EL device).

BACKGROUND ART

Organic electroluminescence (EL) devices are much expected to be useful as inexpensive, large-sized full color display devices of solid state emission type and many developments have been made thereon. An organic EL device is generally constructed from a light emitting layer and a pair of opposite electrodes sandwiching the light emitting layer. When an electric field is applied between the electrodes, electrons are injected from a cathode and holes are injected from an anode into the light emitting layer. The injected electrons recombine with the injected holes in the light emitting layer to form excited states. When the excited states return to the ground state, the energy is released as light.

A phosphorescent organic EL device wherein a phosphorescent organic material is used in the light emitting layer has been proposed. Utilizing the singlet excited state and the triplet excited state of the phosphorescent organic material, a high emission efficiency can be obtained by the phosphorescent organic EL device. When electrons and holes are recombined in an organic EL device, singlet excitons and triplet excitons may generate in a ratio of 1:3 in accordance with their difference in the spin multiplicity. Therefore, an organic EL device employing the phosphorescent emitting material would achieve an emission efficiency three to four times higher than that of an organic EL device employing only the fluorescent emitting material.

The early organic EL device requires a high driving voltage and is insufficient in the emission efficiency and durability. To eliminate these problems, various technical improvements have been made.

The improved emission efficiency and the prolonged lifetime are very important for reducing the power consumption of displays and improving the durability. Therefore, further improvements have been still required. In addition, many studies have been made in order to improve the emission efficiency and the device lifetime of organic EL devices employing a phosphorescent emitting material.

A carbazole derivative has been used particularly as a phosphorescent host material because it has a high triplet energy. It has been also studied to use the carbazole derivative as a hole transporting material in the vicinity of a phosphorescent host, because the carbazole derivative makes the ionization potential (Ip) shallow to increase the hole transporting ability.

Patent Document 1 discloses a derivative having a bis-carbazole skeleton as a carbazole derivative which has been further modified in its molecular structure.

Patent Documents 2 and 3 disclose derivatives each having a monoaminocarbazole skeleton as fluorescent hosts, in which a pyrene residue and an anthracene residue are essential, respectively.

PRIOR ART

Patent Documents

Patent Document 1: KR 10-2010-0033265A
Patent Document 2: JP 2008-78362A
Patent Document 3: JP 2008-195841A

SUMMARY OF THE INVENTION

Problem to be Solved by the Invention

An object of the invention is to provide a highly efficient, long-lifetime organic EL device and an organic EL material which realizes such an organic EL device.

Means for Solving Problem

As a result of extensive research for achieving the above object, the inventor have found that the electron affinity of the monoaminocarbazole compound is reduced by introducing a specific heteroaryl group to the nitrogen atom of the carbazole structure directly or via a linking group. It has been further found that the electron affinity difference between a hole transporting material and a host material in adjacent light emitting layer is reduced when such a compound is used as the hole transporting material, and therefore, the electrons are prevented from moving into the hole transporting layer from the light emitting layer, thereby increasing the degree of recombination of electrons and holes in the light emitting layer and improving the emission efficiency. The present invention is based on these findings.

The present invention provide:

1. An aromatic amine derivative represented by formula (1):

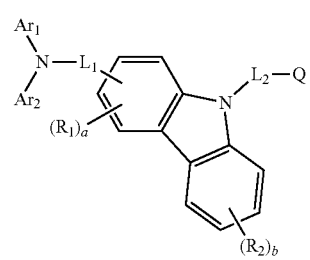

wherein:

$L_1$ represents a single bond, a substituted or unsubstituted arylene group having 6 to 30 ring carbon atoms, or a substituted or unsubstituted heteroarylene group having 5 to 30 ring carbon atoms;

$L_2$ represents a single bond, a substituted or unsubstituted heteroarylene group having 5 to 30 ring carbon atoms, or a substituted or unsubstituted arylene group, wherein the arylene group is selected from a phenylene group, a biphenylene group, a terphenylene group, a naphthylene group, a phenanthrylene group, a chrysenylene group, a perylenylene group, and a fluorenylene group;

each of $Ar_1$ and $Ar_2$ independently represents a substituted or unsubstituted aryl group having 6 to 30 ring carbon atoms or a substituted or unsubstituted heteroaryl group having 5 to 30 ring carbon atoms;

each of $R_1$ and $R_2$ independently represents a fluorine atom, a cyano group, a substituted or unsubstituted alkyl group having 1 to 20 carbon atoms, a substituted or unsubstituted cycloalkyl group having 3 to 20 carbon atoms, a substituted or unsubstituted alkoxy group having 1 to 20 carbon atoms, a substituted or unsubstituted haloalkyl group having 1 to 20 carbon atoms, a substituted or unsubstituted haloalkoxy group having 1 to 20 carbon atoms, a substituted or unsubstituted alkylsilyl group having 1 to 10 carbon atoms, a substituted or unsubstituted arylsilyl group having 6 to 30 carbon atoms, a substituted or unsubstituted aralkyl group having 7 to 30 carbon atoms, a substituted or unsubstituted aryl group having 6 to 30 ring carbon atoms, or a substituted or unsubstituted heteroaryl group having 5 to 30 ring carbon atoms, wherein adjacent $R_1$ groups and adjacent $R_2$ groups may be respectively bonded to each other to form a ring structure together with ring carbon atoms of the benzene ring;

a represents an integer of 0 to 3;

b represents an integer of 0 to 4; and

Q represents a group represented by formula (a):

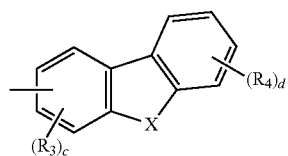

(a)

wherein:

X represents an oxygen atom or a sulfur atom;

each of $R_3$ and $R_4$ independently represents a fluorine atom, a cyano group, a substituted or unsubstituted alkyl group having 1 to 20 carbon atoms, a substituted or unsubstituted cycloalkyl group having 3 to 20 carbon atoms, a substituted or unsubstituted alkoxy group having 1 to 20 carbon atoms, a substituted or unsubstituted haloalkyl group having 1 to 20 carbon atoms, a substituted or unsubstituted haloalkoxy group having 1 to 20 carbon atoms, a substituted or unsubstituted alkylsilyl group having 1 to 10 carbon atoms, a substituted or unsubstituted arylsilyl group having 6 to 30 carbon atoms, a substituted or unsubstituted aralkyl group having 7 to 30 carbon atoms, a substituted or unsubstituted aryl group having 6 to 30 ring carbon atoms, or a substituted or unsubstituted heteroaryl group having 5 to 30 ring carbon atoms, wherein adjacent $R_3$ groups and adjacent $R_4$ groups may be respectively bonded to each other to form a ring structure together with ring carbon atoms of the benzene ring;

c represents an integer of 0 to 3; and d represents an integer of 0 to 4;

2. The aromatic amine derivative according to item 1, wherein the aromatic amine derivative is represented by formula (1-1):

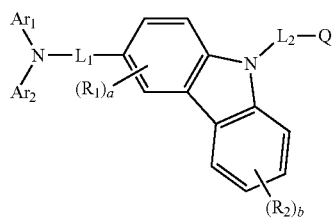

(1-1)

wherein $L_1$, $L_2$, $Ar_1$, $Ar_2$, $R_1$, $R_2$, a, b, and Q are as defined in formula (1);

3. The aromatic amine derivative according to item 1 or 2, wherein Q is represented by formula (a-1):

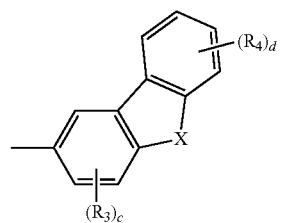

(a-1)

wherein $R_3$, $R_4$, c, d, and X are as defined in formula (a);

4. The aromatic amine derivative according to item 1 or 2, wherein Q is represented by formula (a-2):

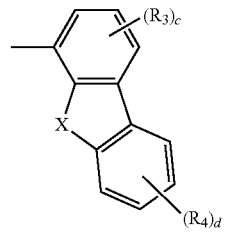

(a-2)

wherein $R_3$, $R_4$, c, d, and X are as defined in formula (a);

5. The aromatic amine derivative according to any one of items 1 to 4, wherein at least one of $L_1$ and $L_2$ represents a single bond or a linking group represented by any one of formulae (b-1) to (b-3):

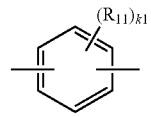

(b-1)

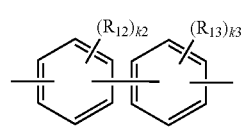

(b-2)

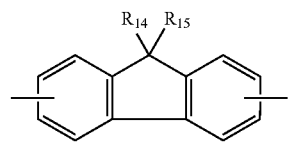

(b-3)

wherein:

each of $R_{11}$ to $R_{13}$ independently represents a fluorine atom, a cyano group, a substituted or unsubstituted alkyl group having 1 to 20 carbon atoms, a substituted or unsubstituted cycloalkyl group having 3 to 20 carbon atoms, a substituted or unsubstituted alkoxy group having 1 to 20 carbon atoms, a substituted or unsubstituted haloalkyl group having 1 to 20 carbon atoms, a substituted or unsubstituted haloalkoxy group having 1 to 20 carbon atoms, a substituted or unsubstituted alkylsilyl group having 1 to 10 carbon atoms, a substituted or unsubstituted arylsilyl group having 6 to 30 carbon atoms, a substituted or unsubstituted aralkyl group having 7 to 30 carbon atoms, a substituted or unsubstituted aryl group having 6 to 30 ring carbon atoms, or a substituted or unsubstituted heteroaryl group having 5 to 30 ring carbon atoms, wherein adjacent $R_{11}$ groups, adjacent $R_{12}$ groups, and adjacent $R_{13}$ groups may be respectively bonded to each other to form a ring structure together with ring carbon atoms of the benzene ring;

each of $R_{14}$ and $R_{15}$ independently represents a hydrogen atom, a substituted or unsubstituted alkyl group having 1 to 20 carbon atoms, a substituted or unsubstituted cycloalkyl group having 3 to 20 carbon atoms, a substituted or unsubstituted haloalkyl group having 1 to 20 carbon atoms, a substituted or unsubstituted aralkyl group having 7 to 30 carbon atoms, a substituted or unsubstituted aryl group having 6 to 30 ring carbon atoms, or a substituted or unsubstituted heteroaryl group having 5 to 30 ring carbon atoms; and each of $k_1$ to $k_3$ represents an integer of 0 to 4;

6. The aromatic amine derivative according to item 5, wherein $L_1$ represents a linking group represented by any one of formulae (b-1) to (b-3).

7. The aromatic amine derivative according to item 5, wherein $L_2$ represents a single bond or a linking group represented by any one of formulae (b-1) to (b-3);

8. The aromatic amine derivative according to item 7, wherein $L_2$ represents a single bond or a linking group represented by formula (b-1);

9. The aromatic amine derivative according to any one of items 1 to 8, wherein X represents an oxygen atom;

10. The aromatic amine derivative according to any one of items 1 to 8, wherein X represents a sulfur atom;

11. A material for electroluminescence device which comprises the aromatic amine derivative according to any one of items 1 to 10;

12. The material for electroluminescence device according to item 11, wherein the material is a hole transporting material;

13. An organic electroluminescence device comprising an anode, a cathode, and one or more organic thin film layers between the anode and the cathode, wherein the organic thin film layers comprise a light emitting layer and at least one layer of the organic thin film layers comprises the aromatic amine derivative according to any one of items 1 to 10;

14. The organic electroluminescence device according to item 13, wherein the organic thin film layers comprise a hole transporting layer and the hole transporting layer comprises the aromatic amine derivative;

15. The organic electroluminescence device according to item 14, wherein a layer comprising an acceptor material is disposed in contact with the hole transporting layer;

16. The organic electroluminescence device according to item 15, wherein the acceptor material is represented by formula (10):

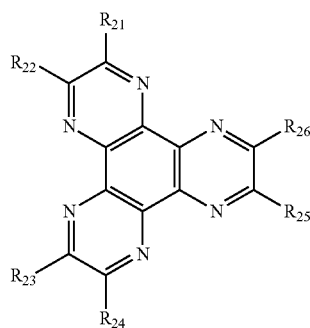

(10)

wherein each of $R_{21}$ to $R_{26}$ independently represents a cyano group, —$CONH_2$, a carboxyl group, or —$COOR_{27}$, wherein $R_{27}$ represents an alkyl group having 1 to 20 carbon atoms or a cycloalkyl group having 3 to 20 carbon atoms, and one or more pairs of $R_{21}$ and $R_{22}$, $R_{23}$ and $R_{24}$, and $R_{25}$ and $R_{26}$ may be respectively bonded to each other to form a group represented by —CO—O—CO—;

17. The organic electroluminescence device according to any one of items 13 to 16, wherein the light emitting layer comprises a phosphorescent emitting material; and 18. The organic electroluminescence device according to item 17, wherein the phosphorescent emitting material is an ortho metallated complex of a metal selected from iridium (Ir), osmium (Os) and platinum (Pt).

Effect of the Invention

According to the invention, an organic EL device having high emission efficiency and long lifetime, and an organic EL material which realizes such an organic EL device are provided.

BRIEF DESCRIPTION OF DRAWINGS

FIG. 1 is a schematic cross-sectional view of an example of the organic EL device of the invention.

Mode for Carrying Out the Invention

The carbon number of a to b in the expression of "a substituted or unsubstituted X group having a to b carbon atoms" is the carbon number of the unsubstituted X group and does not include the carbon atom of the optional substituent. The same is equally applied to "a substituted or unsubstituted X group having a to b ring carbon atoms" and "a substituted or unsubstituted X group having a to b ring atoms," i.e., "a to b" is the number of carbon atoms or atoms which form a ring and does not include the carbon atoms and atoms in a substituent.

Aromatic Amine Derivative

The aromatic amine derivative of the invention is represented by formula (1):

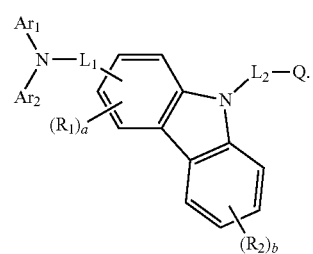

(1)

In formula (1), $L_1$ represents a single bond, a substituted or unsubstituted arylene group having 6 to 30, preferably 6 to 24, and more preferably 6 to 12 ring carbon atoms, or a substituted or unsubstituted heteroarylene group having 5 to 30, preferably 5 to 24, and more preferably 5 to 12 ring carbon atoms.

In formula (1), $L_2$ represents a single bond, a substituted or unsubstituted heteroarylene group having 5 to 30, preferably 5 to 24, and more preferably 5 to 12 ring carbon atoms, or a substituted or unsubstituted arylene group. The arylene group is selected from a phenylene group, a biphenylene group, a terphenylene group, a naphthylene group, a phenanthrylene group, a chrysenylene group, a perylenylene group, and a fluorenylene group.

In formula (1), each of $Ar_1$ and $Ar_2$ independently represents a substituted or unsubstituted aryl group having 6 to 30, preferably 6 to 24, and more preferably 6 to 12 ring carbon atoms or a substituted or unsubstituted heteroaryl group having 5 to 30, preferably 5 to 24, and more preferably 5 to 12 ring carbon atoms.

In formula (1), each of $R_1$ and $R_2$ independently represents a fluorine atom, a cyano group, a substituted or unsubstituted alkyl group having 1 to 20, preferably 1 to 10, and more preferably 1 to 5 carbon atoms, a substituted or unsubstituted cycloalkyl group having 3 to 20, preferably 3 to 10, and more preferably 3 to 6 carbon atoms, a substituted or unsubstituted alkoxy group having 1 to 20, preferably 1 to 10, and more preferably 1 to 5 carbon atoms, a substituted or unsubstituted haloalkyl group having 1 to 20, preferably 1 to 10, and more preferably 1 to 5 carbon atoms, a substituted or unsubstituted haloalkoxy group having 1 to 20, preferably 1 to 10, and more preferably 1 to 5 carbon atoms, a substituted or unsubstituted alkylsilyl group having 1 to 10, preferably 1 to 5, and more preferably 1 to 3 carbon atoms, a substituted or unsubstituted arylsilyl group having 6 to 30, preferably 6 to 24, and more preferably 6 to 18 carbon atoms, a substituted or unsubstituted aralkyl group having 7 to 30, preferably 7 to 25, and more preferably 7 to 13 carbon atoms, a substituted or unsubstituted aryl group having 6 to 30, preferably 6 to 24, and more preferably 6 to 12 ring carbon atoms, or a substituted or unsubstituted heteroaryl group having 5 to 30, preferably 5 to 24, and more preferably 5 to 12 ring carbon atoms. Adjacent $R_1$ groups and adjacent $R_2$ groups may be respectively bonded to each other to form a ring structure together with a nitrogen atom.

In formula (1), a represents an integer of 0 to 3, preferably an integer of 0 to 2, and particularly preferably 0; and b represents an integer of 0 to 4, preferably an integer of 0 to 2, and particularly preferably 0, wherein a=0 and b=0 mean that the substituents $R_1$ and $R_2$ are not present.

In formula (1), Q represents a group represented by formula (a):

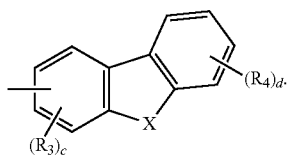

(a)

In formula (a), X represents an oxygen atom or a sulfur atom.

In formula (a), each of $R_3$ and $R_4$ independently represents a fluorine atom, a cyano group, a substituted or unsubstituted alkyl group having 1 to 20, preferably 1 to 10, and more preferably 1 to 5 carbon atoms, a substituted or unsubstituted cycloalkyl group having 3 to 20, preferably 3 to 10, and more preferably 3 to 6 carbon atoms, a substituted or unsubstituted alkoxy group having 1 to 20, preferably 1 to 10, and more preferably 1 to 5 carbon atoms, a substituted or unsubstituted haloalkyl group having 1 to 20, preferably 1 to 10, and more preferably 1 to 5 carbon atoms, a substituted or unsubstituted haloalkoxy group having 1 to 20, preferably 1 to 10, and more preferably 1 to 5 carbon atoms, a substituted or unsubstituted alkylsilyl group having 1 to 10, preferably 1 to 5, and more preferably 1 to 3 carbon atoms, a substituted or unsubstituted arylsilyl group having 6 to 30, preferably 6 to 24, and more preferably 6 to 18 carbon atoms, a substituted or unsubstituted aralkyl group having 7 to 30, preferably 7 to 25, and more preferably 7 to 13 carbon atoms, a substituted or unsubstituted aryl group having 6 to 30, preferably 6 to 24, and more preferably 6 to 12 ring carbon atoms, or a substituted or unsubstituted heteroaryl group having 5 to 30, preferably 5 to 24, and more preferably 5 to 12 ring carbon atoms. Adjacent $R_3$ groups and adjacent $R_4$ groups may be respectively bonded to each other to form a ring structure together with the ring carbon atoms of the benzene ring.

In formula (a), c represents an integer of 0 to 3, preferably an integer of 0 to 2, and particularly preferably 0; and d represents an integer of 0 to 4, preferably an integer of 0 to 2, and particularly preferably 0, wherein c=0 and d=0 mean that the substituents $R_3$ and $R_4$ are not present.

The group represented by formula (a) for Q is preferably represented by formula (a-1) or (a-2) and particularly preferably represented by formula (a-2).

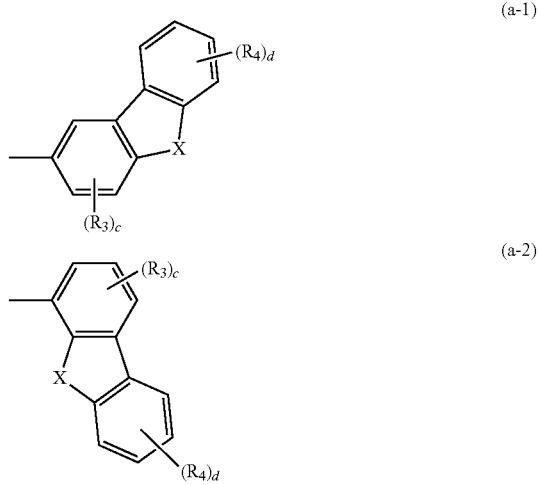

wherein $R_3$, $R_4$, c, d, and X are as defined in formula (a).

Examples of the arylene group for $L_1$ include divalent residues of aromatic compounds selected from benzene, naphthalene, phenanthrene, biphenyl, terphenyl (inclusive of isomers), quaterphenyl (inclusive of isomers), fluoranthene, triphenylene, 9,9-dimethylfluorene, benzo[c]phenanthrene, benzo[a]triphenylene, naphtho[1,2-c]phenanthrene, naphtho[1,2-a]triphenylene, dibenzo[a,c]triphenylene, and benzo[b]fluoranthene. Preferred examples thereof include 1,4-phenylene group, 1,3-phenylene group, biphenyl-4,4'-diyl group, biphenyl-3,3'-diyl group, biphenyl-3,4'-diyl group, p-terphenyl-4,4''-diyl group, m-terphenyl-3,3'-diyl group, naphthalene-2,6-diyl group, naphthalene-2,7-diyl group, naphthalene-1,4-diyl group, naphthalene-1,5-diyl group, phenanthrene-2,7-diyl group, fluoranthene-3,9-diyl group, 9,9-dimethylfluorene-2,7-diyl group, 9,9-diphenylfluorene-2,7-diyl group, 9-methyl-9-phenylfluorene-2,7-diyl group, 6,6,12,12-tetramethylindeno[1,2-b]fluorene-2,8-diyl group, and 2-phenyl-9,9-dimethylfluoranthene-2,4'-diyl group. Particularly preferred examples thereof include 1,4-a phenylene group, biphenyl-4,4'-diyl group, 9,9-dimethylfluorene-2,7-diyl group, and 9,9-diphenylfluorene-2,7-diyl group.

The heteroarylene group for $L_1$ includes at least one, preferably 1 to 3 hetero atoms selected from a nitrogen atom, an oxygen atom, and a sulfur atom. Examples thereof include divalent residues of heterocyclic compounds selected from pyrrole, furan, thiophene, pyridine, pyridazine, pyrimidine, pyrazine, triazine, imidazole, oxazole, thiazole, pyrazole, isoxazole, isothiazole, oxadiazole, thiadiazole, triazole, indoline, isoindoline, benzofuran, isobenzofuran, benzothiophene, indolizine, quinolizine, quinoline, isoquinoline, cinnoline, phthalazine, quinazoline, quinoxaline, benzimidazole, benzoxazole, benzothiazole, indazole, benzisoxazole, benzisothiazole, carbazole, dibenzofuran, dibenzothiophene, phenanthridine, acridine, phenanthroline, phenazine, phenothiazine, phenoxazine, and xanthene. Preferred examples thereof include divalent residues of heterocyclic compounds selected from furan, thiophene, pyridine, benzofuran, benzothiophene, dibenzofuran, and dibenzothiophene. More preferred examples include pyridine-2,5-diyl group, benzothiophene-2,5-diyl group, dibenzofuran-2,8-diyl group, and dibenzothiophene-2,8-diyl group.

The arylene group for $L_2$ is preferably 1,4-phenylene group, 1,3-phenylene group, biphenyl-4,4'-diyl group, biphenyl-3,4'-diyl group, biphenyl-3,3'-diyl group, naphthalene-2,6-diyl group, naphthalene-1,4-diyl group, naphthalene-1,5-diyl group, phenanthrene-2,7-diyl group, and 9,9-dimethylfluorene-2,7-diyl group, and particularly preferably 1,4-phenylene group, biphenyl-4,4'-diyl group, and 9,9-dimethylfluorene-2,7-diyl group.

Examples and preferred examples of the heteroarylene group for $L_2$ are defined as in the heteroarylene group for $L_1$.

Examples of the aryl group for $Ar_1$ and $Ar^2$ include phenyl group, naphthyl group, phenanthryl group, biphenylyl group, terphenylyl group, quaterphenyl group, fluoranthenyl group, triphenylenyl group, 9,9-dimethyl fluorenyl group, benzo[c]phenanthrenyl group, benzo[a]triphenylenyl group, naphtho[1,2-c]phenanthrenyl group, naphtho[1,2-a]triphenylenyl group, dibenzo[a,c]triphenylenyl group, and benzo[b]fluoranthenyl group. Preferred examples thereof include phenyl group, 4-biphenylyl group, 3-biphenylyl group, m-terphenyl-4-yl group, m-terphenyl-5'-yl group, p-terphenyl-4-yl group, o-terphenyl-4-yl group, o-terphenyl-3'-yl group, 1-naphthyl group, 2-naphthyl group, fluoranthene-3-yl group, 4-(1-naphthyl)phenyl group, 4-(2-naphthyl)phenyl group, 4-(m-terphenyl-3'-yl)phenyl group, 9,9-dimethyl-fluorene-2-yl group, 7-phenyl-9,9-dimethylfluorene-2-yl group, 7-(2-naphthyl)-9,9-dimethylfluorene-2-yl group, 4-(9,9-dimethylfluorene-2-yl)phenyl group, triphenylene-2-yl group, and phenanthrene-9-yl group. Particularly preferred examples include phenyl group, 4-biphenylyl group, 1-naphthyl group, 2-naphthyl group, 9,9-dimethylfluorene-2-yl group, and p-terphenyl-4-yl group.

The heteroaryl group for $Ar_1$ and $Ar_2$ includes at least one, preferably 1 to 3 hetero atoms selected from a nitrogen atom, an oxygen atom, and a sulfur atom. Examples thereof include pyrrolyl group, furyl group, thienyl group, pyridyl group, pyridazinyl group, pyrimidinyl group, pyrazinyl group, triazinyl group, imidazolyl group, oxazolyl group, thiazolyl group, pyrazolyl group, isoxazolyl group, isothiazolyl group, oxadiazolyl group, thiadiazolyl group, triazolyl group, indolyl group, isoindolyl group, benzofuranyl group, isobenzofuranyl group, benzothiophenyl group, isoindolyl group, quinolizinyl group, quinolyl group, isoquinolyl group, cinnolyl group, phthalazinyl group, quinazolinyl group, quinoxalinyl group, benzimidazolyl group, benzoxazolyl group, benzothiazolyl group, indazolyl group, benzisoxazolyl group, benzisothiazolyl group, carbazolyl group, dibenzofuranyl group, dibenzothiophenyl group, phenanthridinyl group, acridinyl group, phenanthrolinyl group, phenazinyl group, phenothiazinyl group, phenoxazinyl group, and xanthenyl group. Preferred examples thereof include furyl group, thienyl group, benzofuranyl group, benzothiophenyl group, dibenzofuranyl group, and dibenzothiophenyl group. More preferred examples thereof include 2-dibenzofuranyl group, 3-dibenzofuranyl group, 4-dibenzofuranyl group, 2-dibenzothiophenyl group, 3-dibenzothiophenyl group, and 4-dibenzothiophenyl group.

Examples of the alkyl group for $R_1$ to $R_4$ include methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptylctyl group, and 3-methylpentyl group. Preferred examples thereof include methyl group, t-butyl group, ethyl group, n-propyl group, and isopropyl group.

Examples of the cycloalkyl group for $R_1$ to $R_4$ include cyclopropyl group, cyclobutyl group, cyclopentyl group, cyclohexyl group, and cyclooctyl group, with cyclopentyl group and cyclohexyl group being preferred.

Examples of the haloalkyl group for $R_1$ to $R_4$ include chloromethyl group, 1-chloromethyl group, 2-chloroethyl group, 2-chloroisobutyl, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, fluoromethyl group, 1-fluoromethyl group, 2-fluoromethyl group, 2-fluoroisobutyl group, 1,2-difluoroethyl group, difluoromethyl group, trifluoromethyl group, pentafluoroethyl group, perfluoroisopropyl group, perfluorobutyl group, and perfluorocyclohexyl group, with trifluoromethyl group, pentafluoroethyl group, 2,2,2-trifluoroethyl group, and heptafluoropropyl group being preferred.

The alkoxy group for $R_1$ to $R_4$ is represented by $OX^1$, wherein $X^1$ represents an alkyl group which is selected from the alkyl groups and the preferred alkyl groups for $R_1$ to $R_4$ mentioned above.

The haloalkoxy group for $R_1$ to $R_4$ is represented by $OX^2$, wherein $X^2$ represents a haloalkyl group which is selected from the haloalkyl groups and the preferred haloalkyl groups for $R_1$ to $R_4$ mentioned above.

The alkylsilyl group for $R_1$ to $R_4$ is represented by —$SiH_2R$, —$SiHR_2$, or —$SiR_3$, wherein R represents an alkyl group which is selected from the alkyl groups and the preferred alkyl groups for $R_1$ to $R_4$ mentioned above. Two or three R groups may be the same or different. Preferred examples of the alkylsilyl group include trimethylsilyl group, triethylsilyl group, and t-butyldimethylsilyl group.

Examples of the aryl group for $R_1$ to $R_4$ include phenyl group, naphthyl group, phenanthryl group, biphenyl group, terphenylyl group, quaterphenylyl group, fluoranthenyl group, triphenylenyl group, 9,9-dimethylfluorenyl group, benzo[c]phenanthrenyl group, benzo[a]triphenylenyl group, naphtho[1,2-c]phenanthrenyl group, naphtho[1,2-a]triphenylenyl group, dibenzo[a,c]triphenylenyl group, and benzo[b]fluoranthenyl group, with phenyl group, 4-biphenyl group, 3-biphenyl group, 5'-m-terphenylyl group, 1-naphthyl group, 9,9-dimethylfluorene-2-yl group, 2-naphthyl group, and 9-phenanthrenyl group being preferred.

The arylsilyl group for $R_1$ to $R_4$ is represented by —$SiH_2Ar$, —$SiHAr_2$, or —$SiAr_3$, wherein Ar is an aryl group which is selected from the aryl groups and the preferred aryl groups for $R_1$ to $R_4$ mentioned above. Two or three Ar groups may be the same or different. Preferred is a triphenylsilyl group.

Examples of the aralkyl group for $R_1$ to $R_4$ include benzyl group, 1-phenylethyl group, 2-phenylethyl group, 1-phenylisopropyl group, 2-phenylisopropyl group, and phenyl-t-butyl group, with benzyl group, 1-phenylethyl group, and 2-phenylethyl group being preferred.

The heteroaryl group for $R_1$ to $R_4$ comprises at least one, preferably 1 to 3 hetero atoms selected from a nitrogen atom, an oxygen atom, and a sulfur atom. Examples thereof include pyrrolyl group, furyl group, thienyl group, pyridyl group, pyridazinyl group, pyrimidinyl group, pyrazinyl group, triazinyl group, imidazolyl group, oxazolyl group, thiazolyl group, pyrazolyl group, isoxazolyl group, isothiazolyl group, oxadiazolyl group, thiadiazolyl group, triazolyl group, indolyl group, isoindolyl group, benzofuranyl group, isobenzofuranyl group, benzothiophenyl group, indolizinyl group, quinolizinyl group, quinolyl group, isoquinolyl group, cinnolyl group, phthalazinyl group, quinazolinyl group, quinoxalinyl group, benzimidazolyl group, benzoxazolyl group, benzothiazolyl group, indazolyl group, benzisoxazolyl group, benzisothiazolyl group, carbazolyl group, dibenzofuranyl group, dibenzothiophenyl group, phenanthridinyl group, acridinyl group, phenanthrolinyl group, phenazinyl group, phenothiazinyl group, phenoxazinyl group, and xanthenyl group, with furyl group, thienyl group, benzofuranyl group, benzothiophenyl group, dibenzofuranyl group, and dibenzothiophenyl being preferred.

Examples of the divalent group which is formed by adjacent $R_1$ groups, adjacent $R_2$ groups, adjacent $R_3$ groups, or adjacent $R_4$ groups include butane-1,4-diyl group and 1,3-butadiene-1,4-diyl group. Examples of the ring structure formed by the bonded $R_1$ groups, the bonded $R_2$ groups, the bonded $R_3$ groups, or the bonded $R_4$ groups together with the ring carbon atoms of the benzene ring include an aromatic hydrocarbon ring having 6 to 30 ring carbon atoms, an aromatic heterocyclic ring having 5 to 30 ring carbon atoms, and the aromatic hydrocarbon ring or the aromatic heterocyclic ring which are partly saturated.

At least one of $L_1$ and $L_2$ preferably represents a single bond or a linking group represented by any of formulae (b-1) to (b-3) and particularly preferably represents a single bond or a linking group represented by formula (b-1).

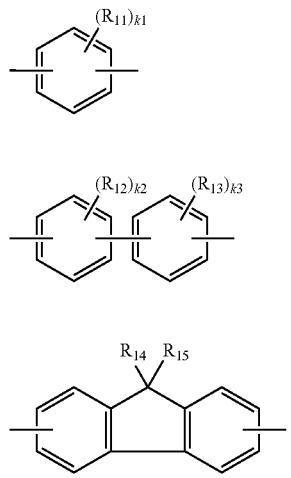

In formulae (b-1) to (b-3), each of $R_{11}$ to $R_{13}$ independently represents a fluorine atom, a cyano group, a substituted or unsubstituted alkyl group having 1 to 20, preferably 1 to 10, and more preferably 1 to 5 carbon atoms, a substituted or unsubstituted cycloalkyl group having 3 to 20, preferably 3 to 10, and more preferably 3 to 6 carbon atoms, a substituted or unsubstituted alkoxy group having 1 to 20, preferably 1 to 10, and more preferably 1 to 5 carbon atoms, a substituted or unsubstituted haloalkyl group having 1 to 20, preferably 1 to 10, and more preferably 1 to 5 carbon atoms, a substituted or unsubstituted haloalkoxy group having 1 to 20, preferably 1 to 10, and more preferably 1 to 5 carbon atoms, a substituted or unsubstituted alkylsilyl group having 1 to 10, preferably 1 to 5, and more preferably 1 to 3 carbon atoms, a substituted or unsubstituted arylsilyl group having 6 to 30, preferably 6 to 24, and more preferably 6 to 18 carbon atoms, a substituted or unsubstituted aralkyl group having 7 to 30, preferably 7 to 25, and more preferably 7 to 13 carbon atoms, a substituted or unsubstituted aryl group having 6 to 30, preferably 6 to 24, and more preferably 6 to 12 ring carbon atoms, or a substituted or unsubstituted heteroaryl group having 5 to 30, preferably 5 to 24, and more preferably 5 to 12 ring carbon atoms; and adjacent $R_{11}$ groups, adjacent $R_{12}$ groups, and adjacent $R_{13}$ groups may be respectively bonded to each other to form a ring structure together with ring carbon atoms of the benzene ring.

Each of the alkyl group, the cycloalkyl group, the alkoxy group, the haloalkyl group, the haloalkoxy group, the alkylsilyl group, the arylsilyl group, the aralkyl group, the aryl group, and the heteroaryl group for $R_{11}$ to $R_{13}$ is defined as in the corresponding group for $R_1$ to $R_4$.

Examples of the divalent group which is formed by adjacent $R_{11}$ groups, adjacent $R_{12}$ groups, or adjacent $R_{13}$ groups include butane-1,4-diyl group and 1,3-butadiene-1,4-diyl group. Examples of the ring structure formed by the bonded $R_{11}$ groups, the bonded $R_{12}$ groups, or the bonded $R_{13}$ groups together with the ring carbon atoms of the benzene ring include an aromatic hydrocarbon ring having 6 to 30 ring carbon atoms, an aromatic heterocyclic ring having 5 to 30 ring carbon atoms, and the aromatic hydrocarbon ring or the aromatic heterocyclic ring which are partly saturated.

Each of $k_1$ to $k_3$ represents an integer of 0 to 4, preferably an integer of 0 to 2, and particularly preferably 0. When each of $k_1$ to $k_3$ represents 0, each of $R_{11}$, $R_{12}$, and $R_{13}$ groups is not present, respectively.

Each of $R_{14}$ and $R_{15}$ independently represents a hydrogen atom, a substituted or unsubstituted alkyl group having 1 to 20, preferably 1 to 10, and more preferably 1 to 5 carbon atoms, a substituted or unsubstituted cycloalkyl group having 3 to 20, preferably 3 to 10, and more preferably 3 to 6 carbon atoms, a substituted or unsubstituted haloalkyl group having 1 to 20, preferably 1 to 10, and more preferably 1 to 5 carbon atoms, a substituted or unsubstituted aralkyl group having 7 to 30, preferably 7 to 25, and more preferably 7 to 13 carbon atoms, a substituted or unsubstituted aryl group having 6 to 30, preferably 6 to 24, and more preferably 6 to 12 ring carbon atoms, or a substituted or unsubstituted heteroaryl group having 5 to 30, preferably 5 to 24, and more preferably 5 to 12 ring carbon atoms.

Each of the alkyl group, the cycloalkyl group, the haloalkyl group, the aralkyl group, the aryl group, and the heteroaryl group for $R_{14}$ and $R_{15}$ is defined as in the corresponding group for $R_1$ to $R_4$.

The phenylene group represented by formula (b-1) includes, for example, 1,2-phenylene group, 1,3-phenylene group, and 1,4-phenylene group, with 1,4-phenylene group being particularly preferred.

The biphenyldiyl group represented by formula (b-2) includes, for example, biphenyl-4,4'-diyl group, biphenyl-3,4'-diyl group, and biphenyl-3,3'-diyl group, with biphenyl-4,4'-diyl group being particularly preferred.

The fluorenediyl group represented by formula (b-3) includes, for example, 9,9-dimethylfluorene-2,7-diyl group, 9,9-diphenylfluorene-2,7-diyl group, and 9-methyl-9-phenylfluorene-2,7-diyl group, with 9,9-dimethylfluorene-2,7-diyl group being particularly preferred.

The aromatic amine derivative of the invention is preferably represented by formula (1-1):

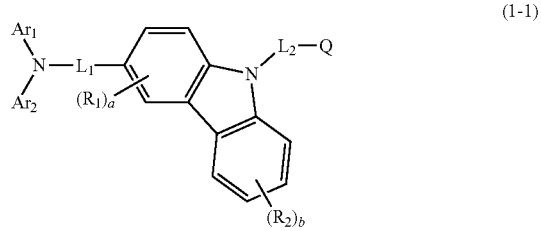

(1-1)

wherein $L_1$, $L_2$, $Ar_1$, $Ar_2$, $R_1$, $R_2$, a, b, and Q are as defined above.

Examples of the optional substituent when saying "substituted or unsubstituted" hereinbefore and hereinafter include a fluorine atom, a cyano group, an alkyl group having 1 to 20, preferably 1 to 5 carbon atoms, a cycloalkyl group having 3 to 20, preferably 5 to 12 carbon atoms, an alkoxy group having 1 to 20, preferably 1 to 5 carbon atoms, a haloalkyl group having 1 to 20, preferably 1 to 5 carbon atoms, a haloalkoxy group having 1 to 20, preferably 1 to 5 carbon atoms, an alkylsilyl group having 1 to 10, preferably 1 to 5 carbon atoms, an aryl group having 6 to 30, preferably 6 to 18 ring carbon atoms, an aryloxy group having 6 to 30, preferably 6 to 18 ring carbon atoms, an arylsilyl group having 6 to 30, preferably 6 to 18 carbon atoms, an aralkyl group having 7 to 30, preferably 7 to 20 carbon atoms, and a heteroaryl group having 5 to 30, preferably 5 to 18 ring atoms.

Examples of the aromatic amine derivative are shown below, although not limited to the following compounds.

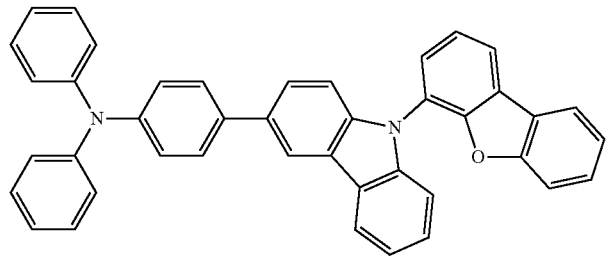

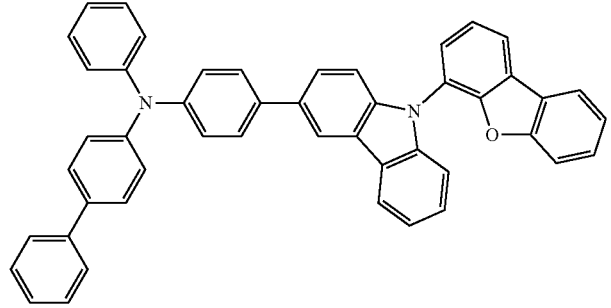

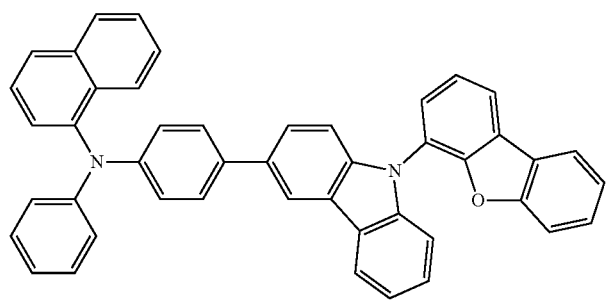

-continued
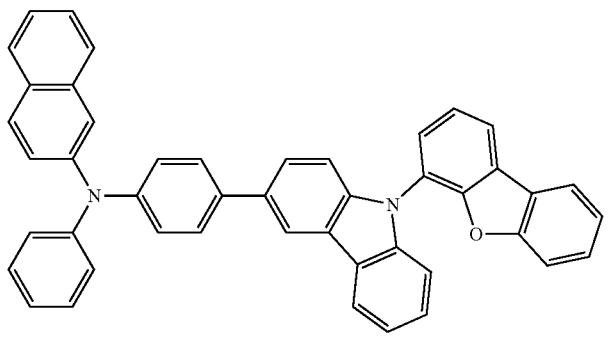
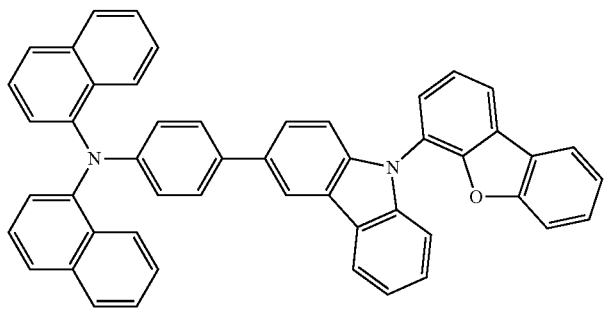
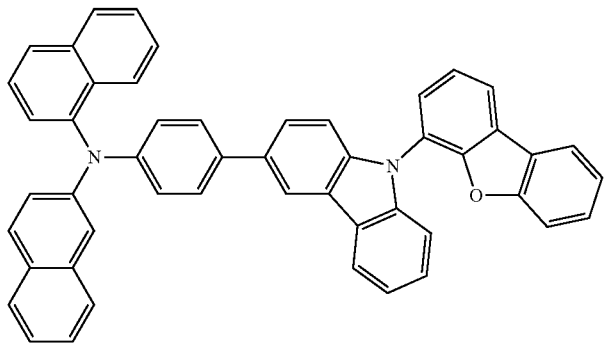
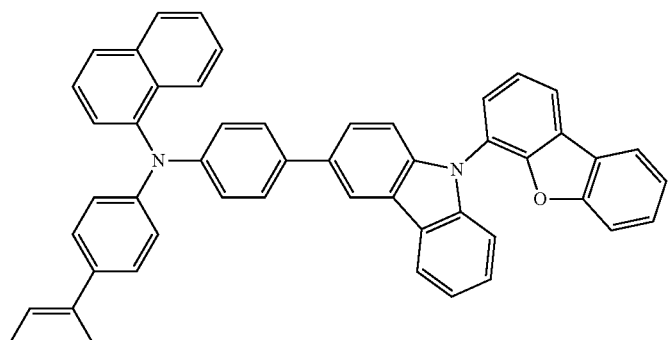
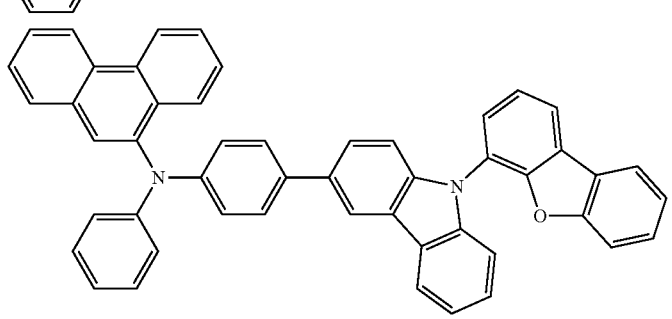

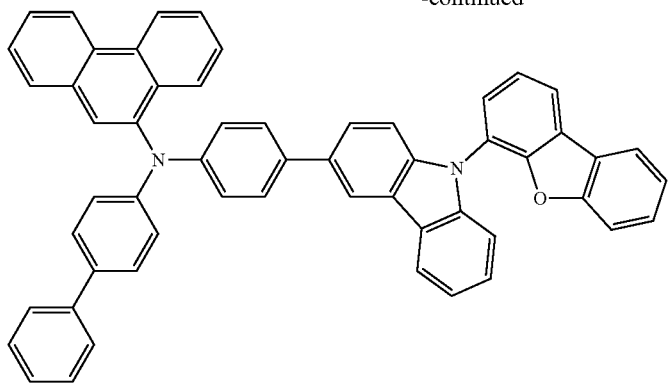
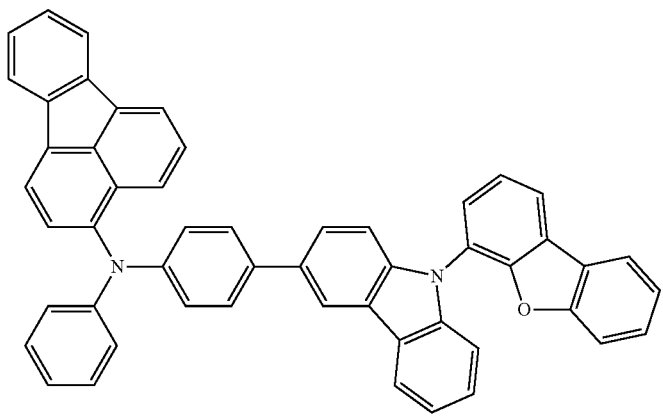
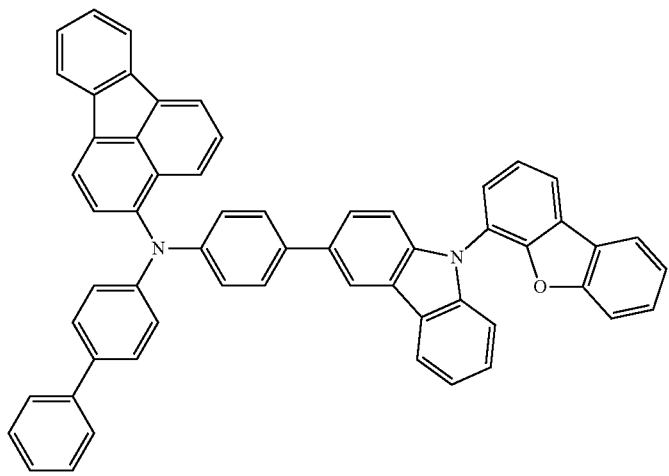

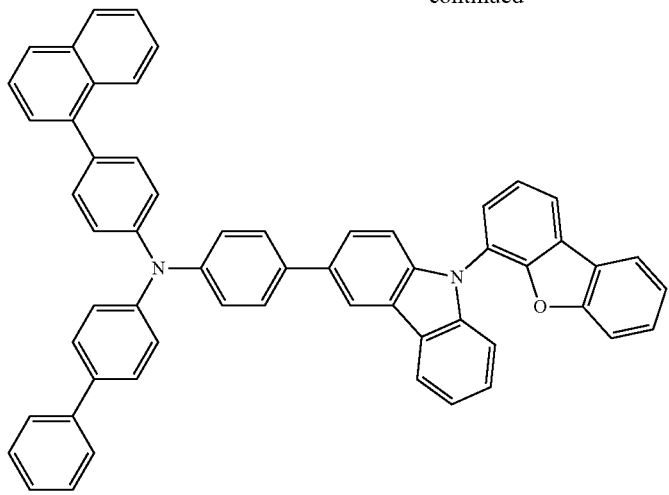
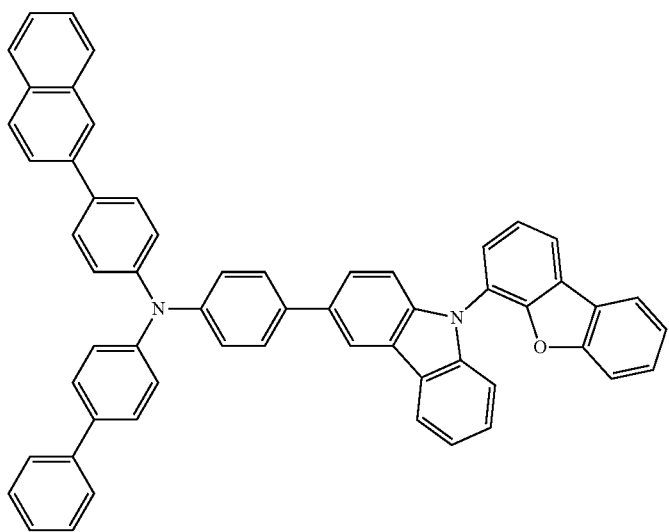
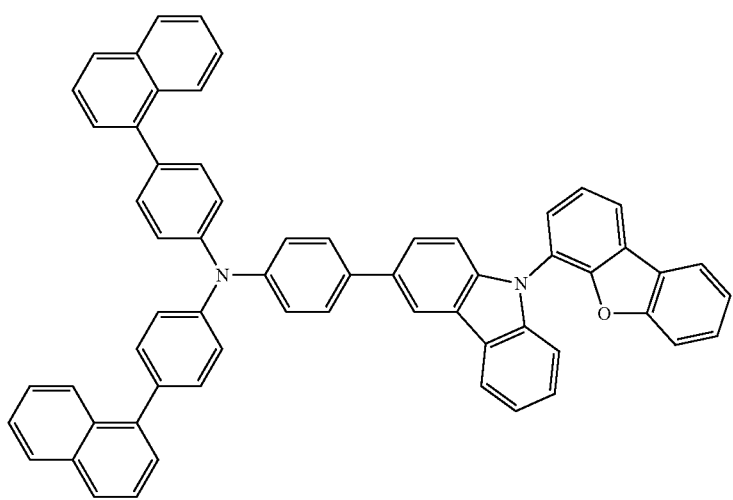

-continued
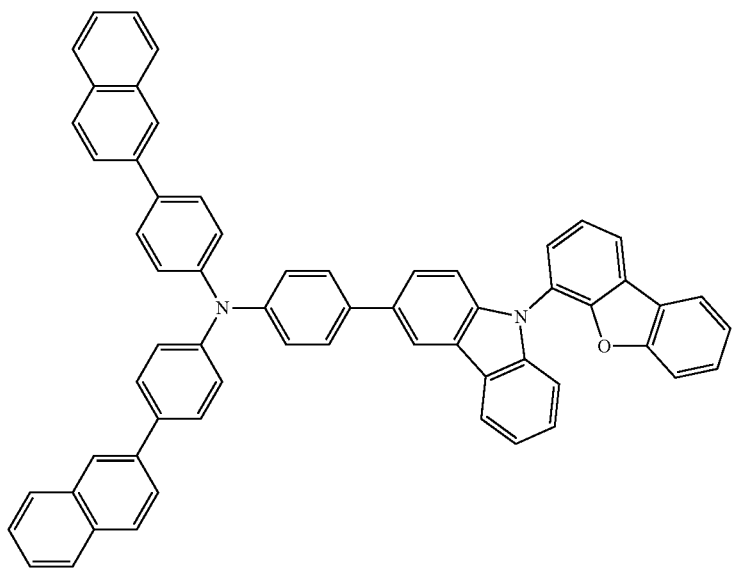
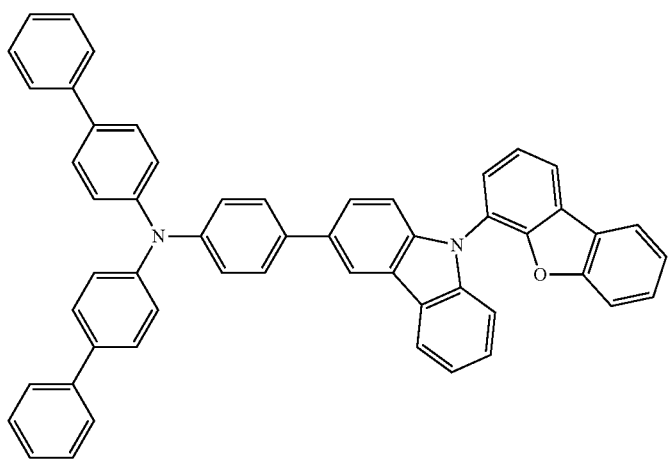
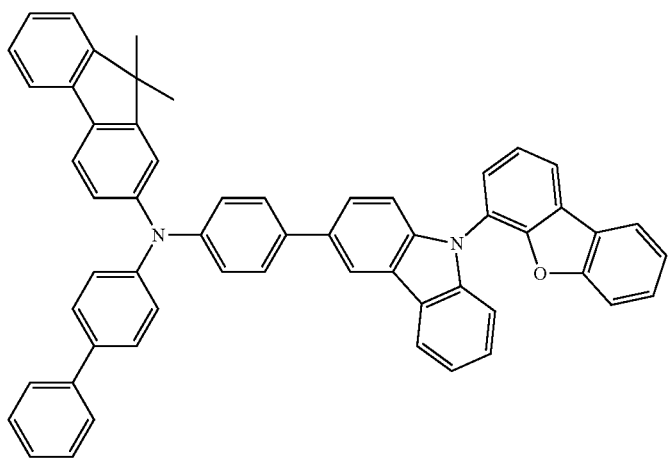

-continued
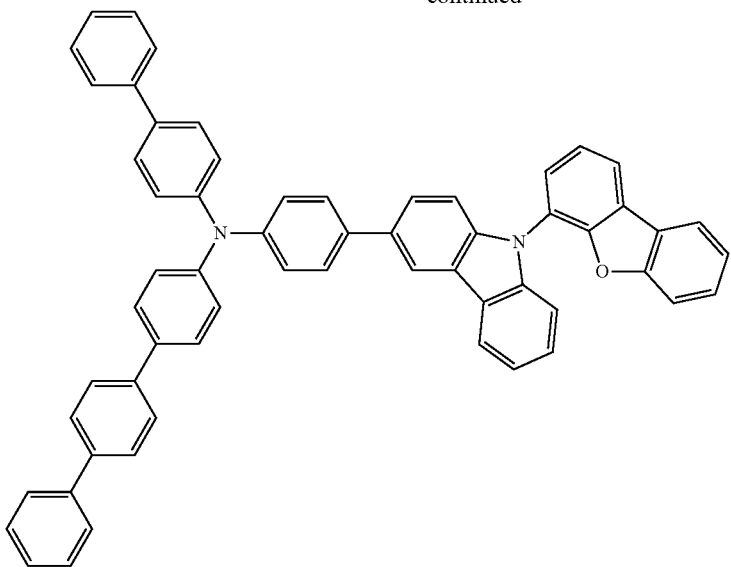
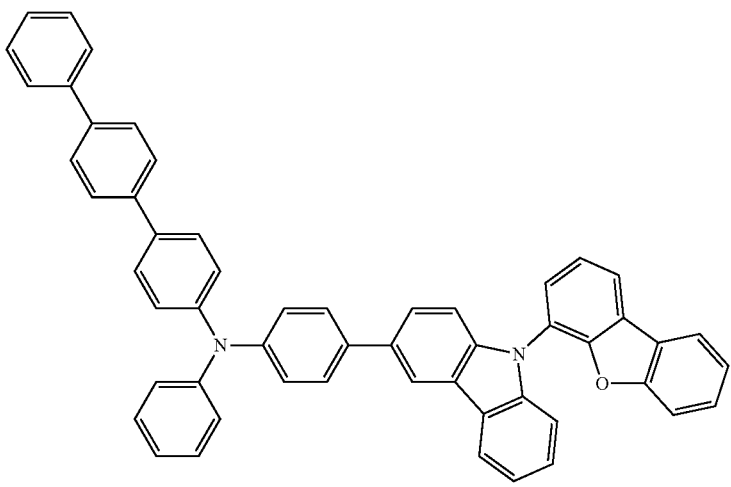
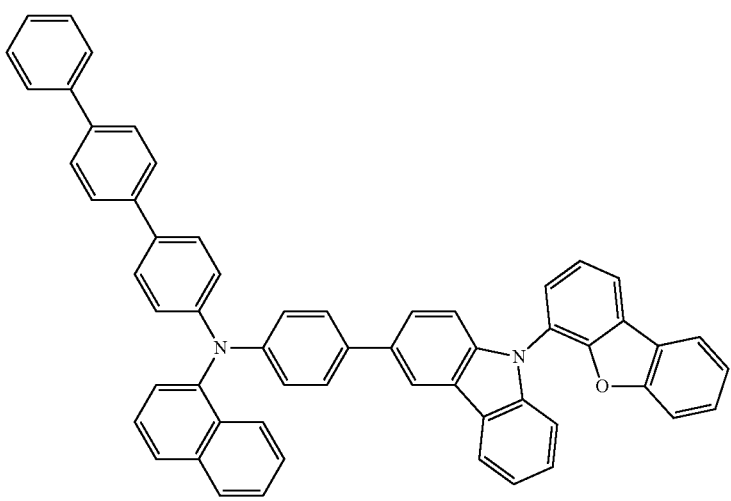

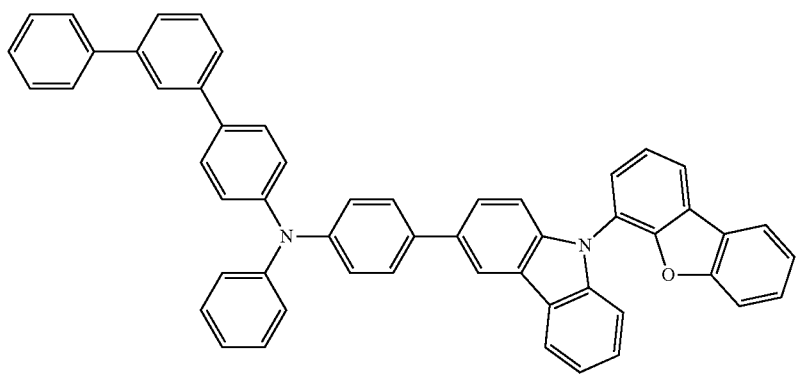
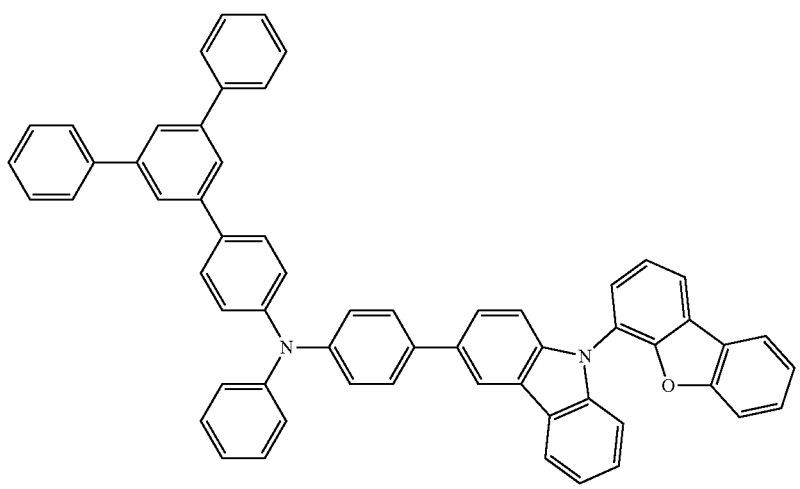
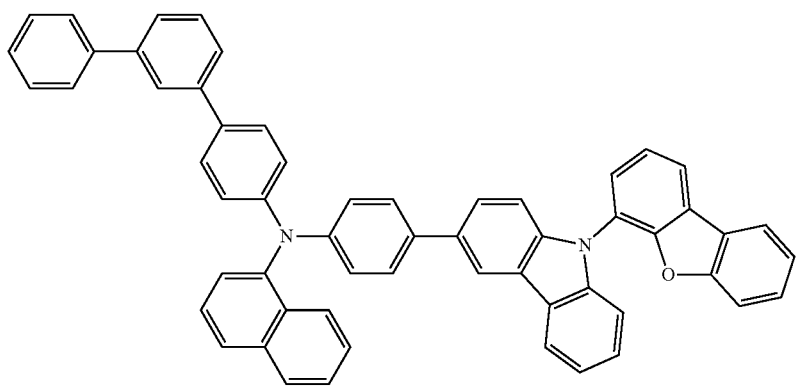

-continued
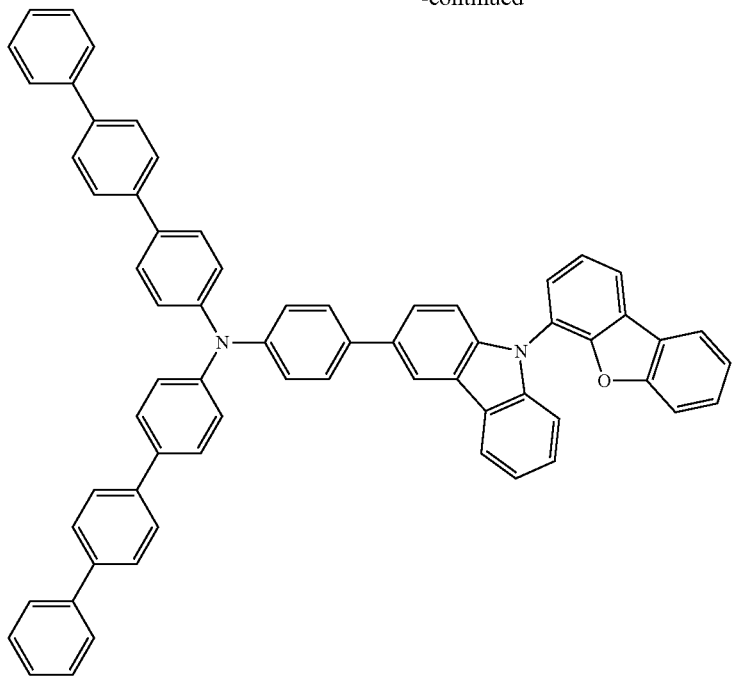
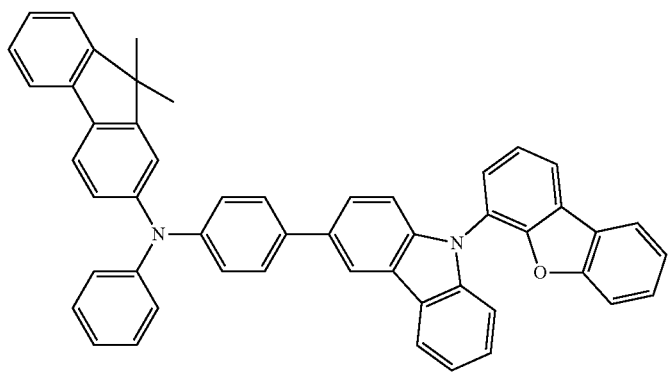
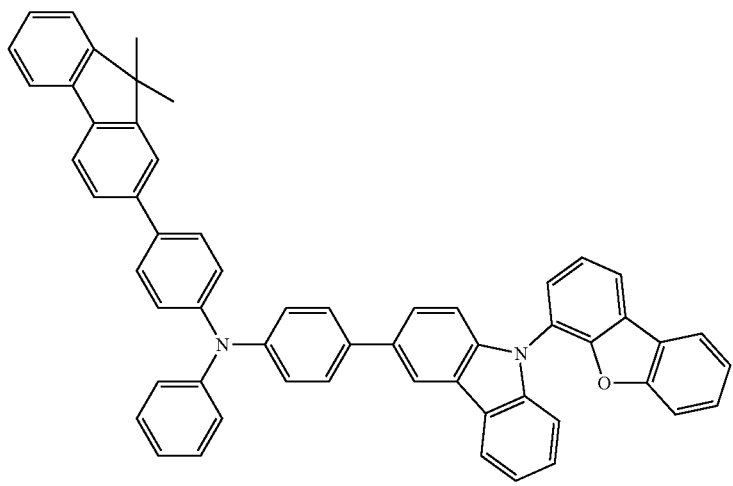

-continued
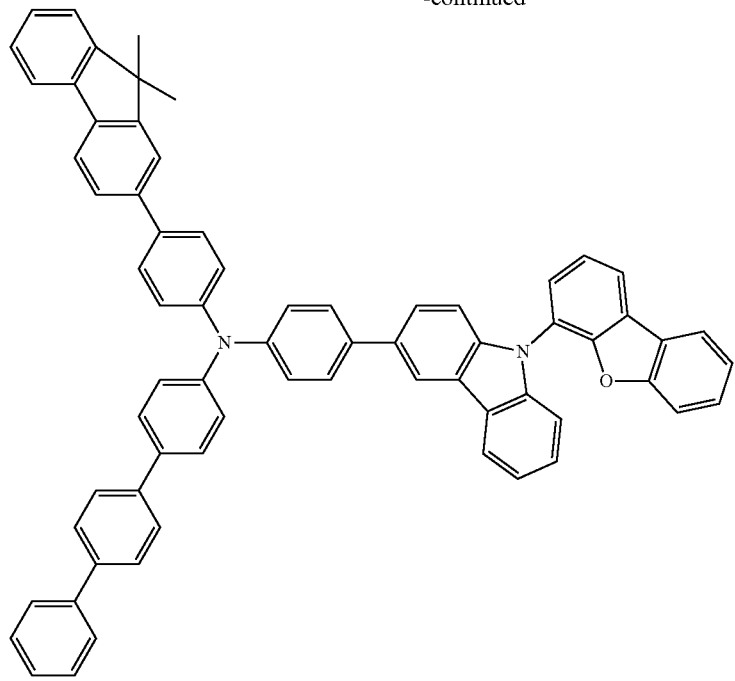
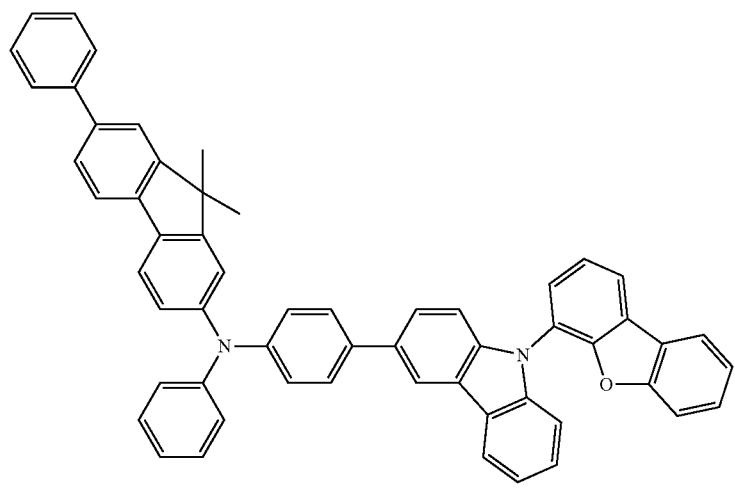
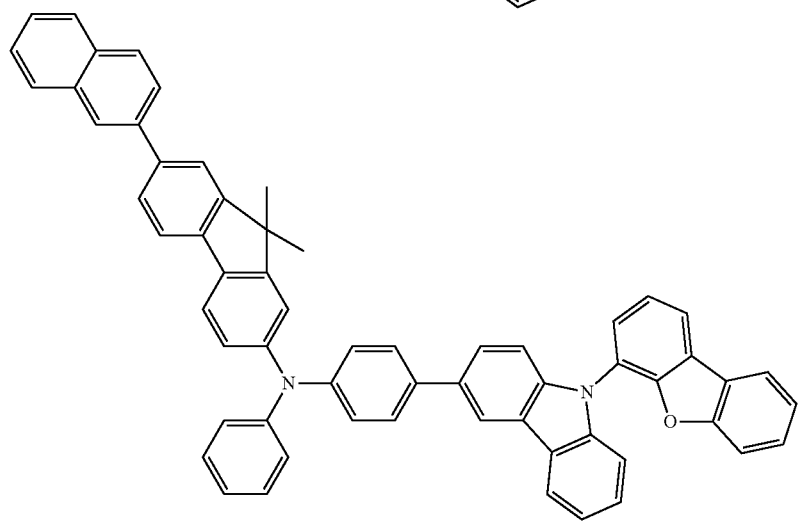

-continued
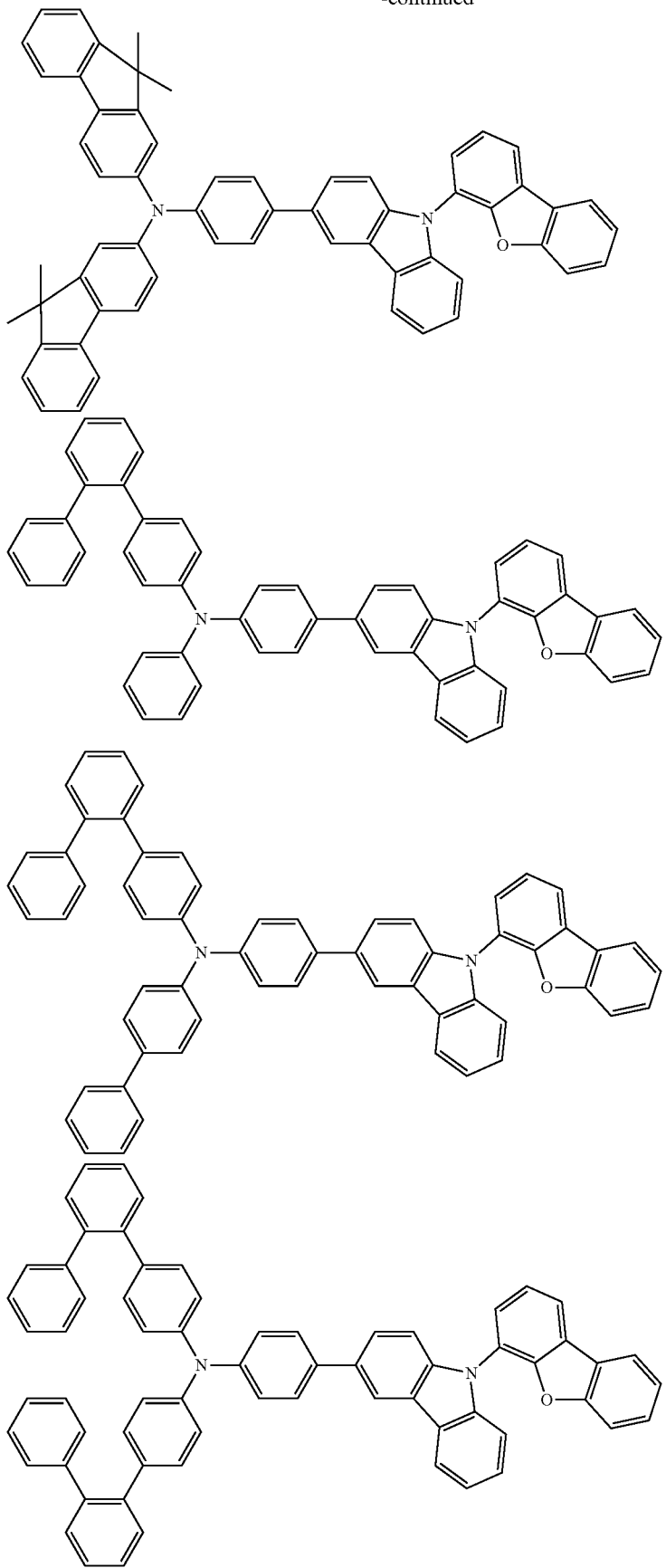

-continued
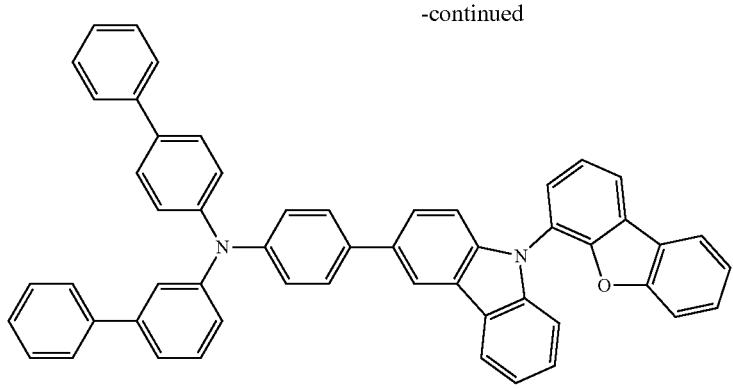
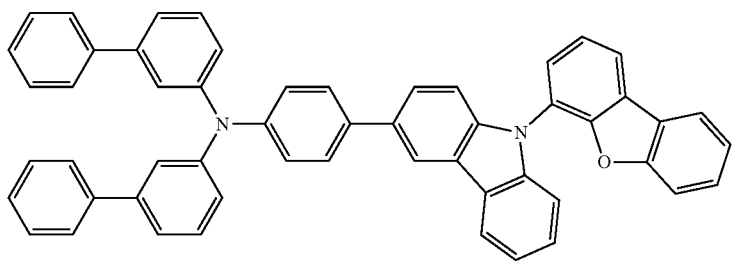
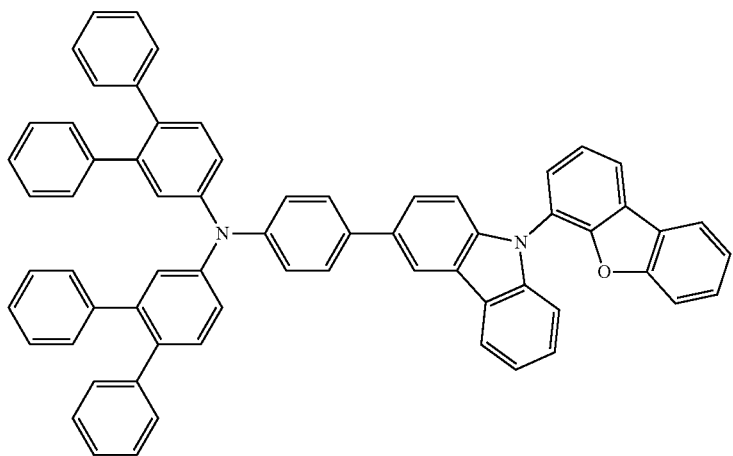
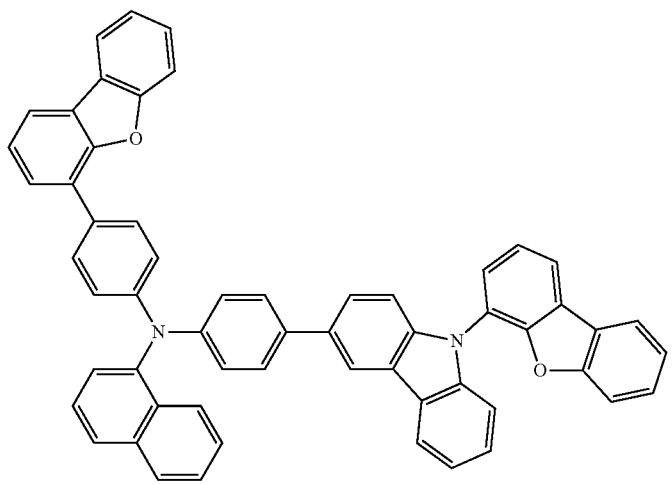

-continued
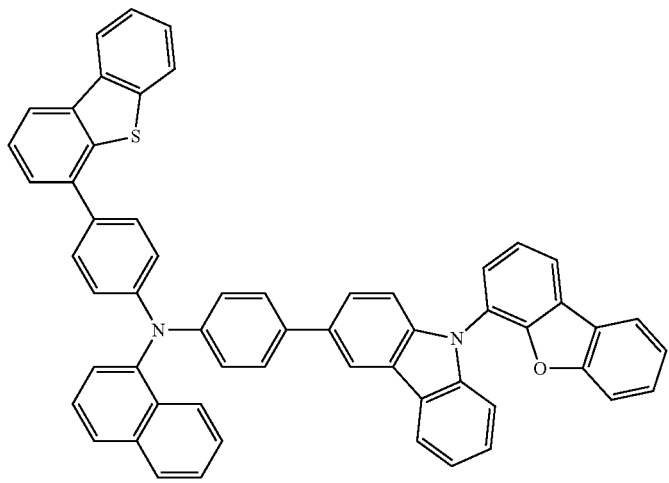
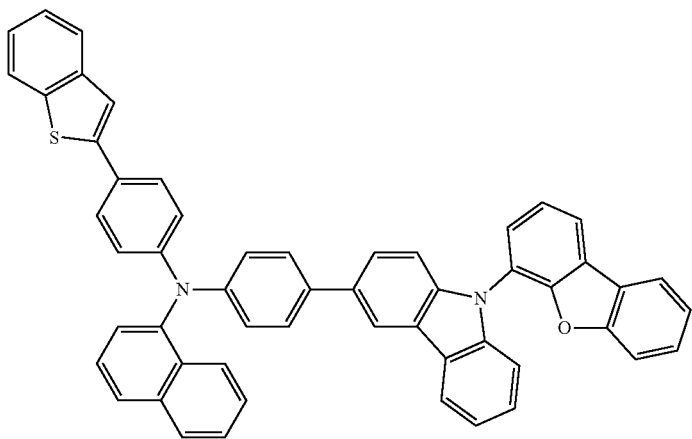
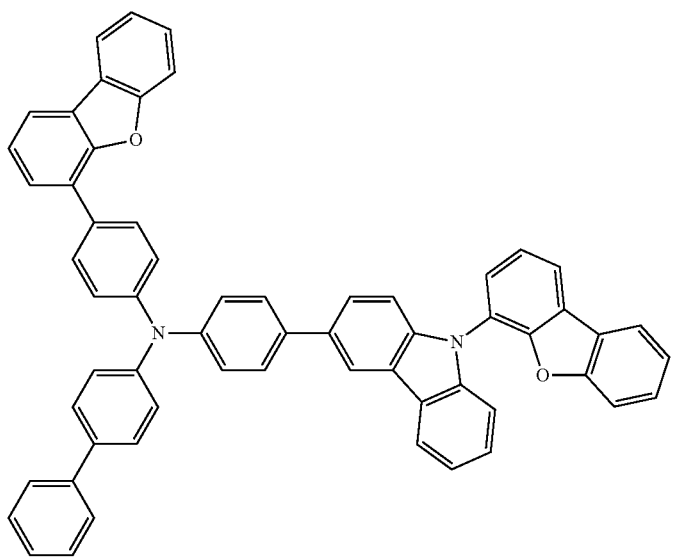

-continued
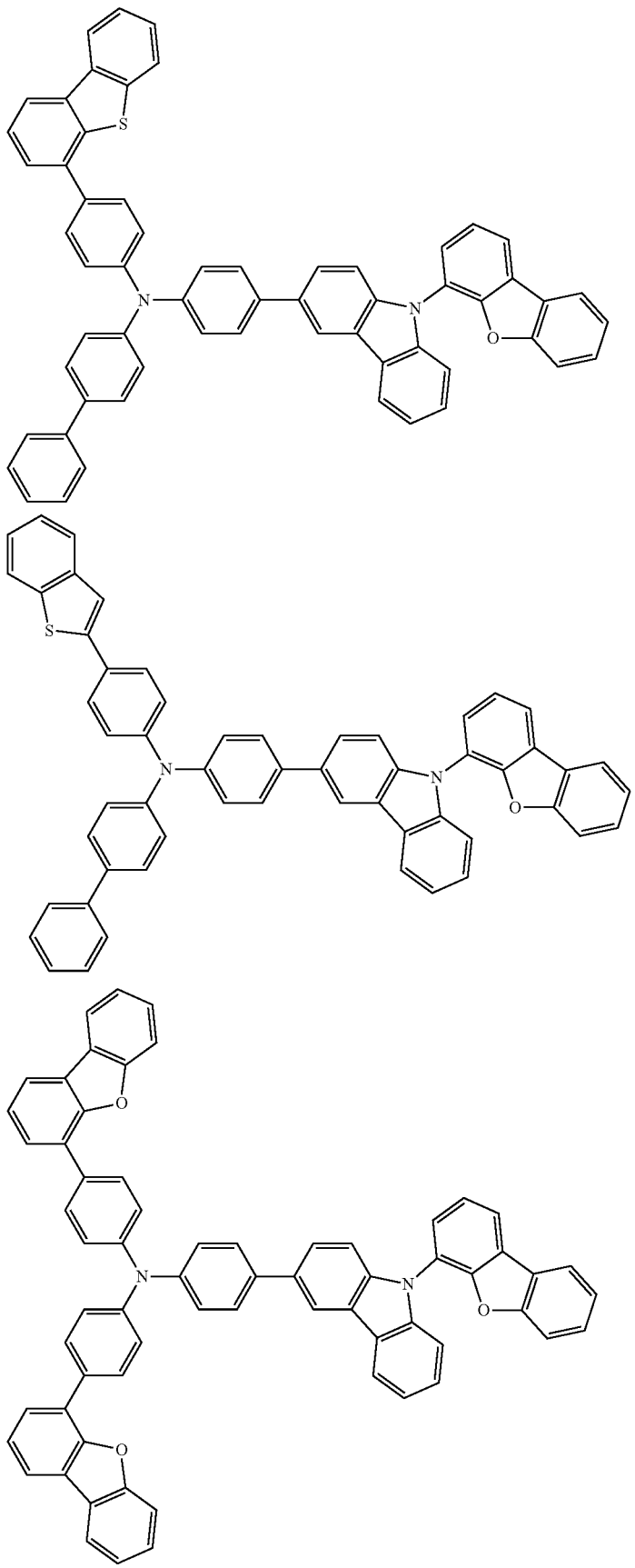

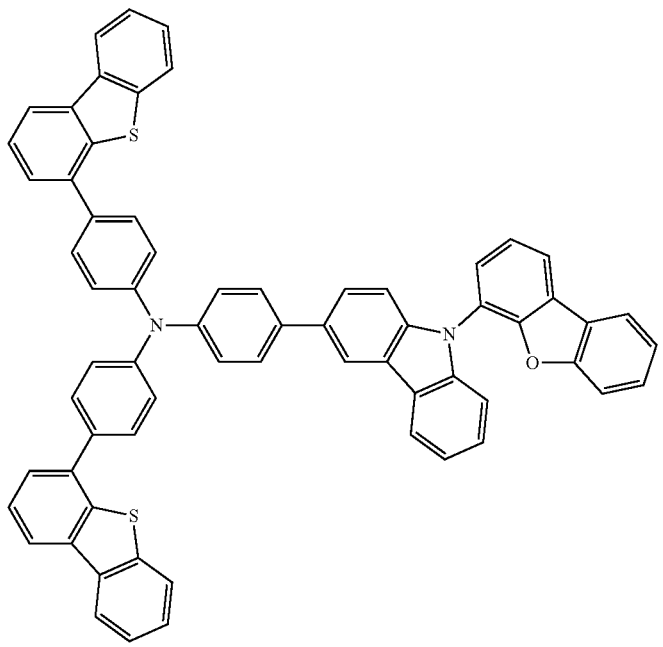
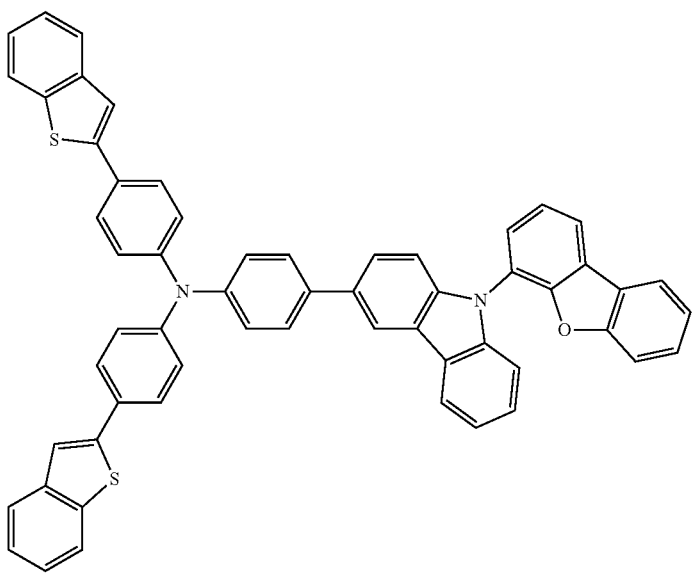
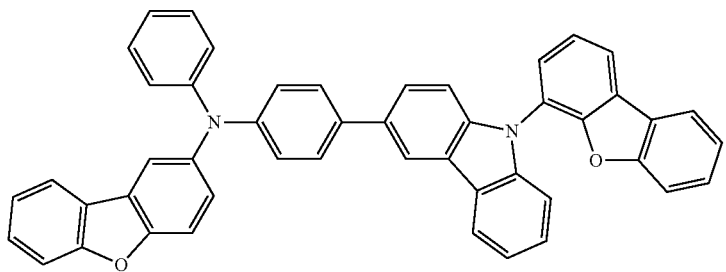

-continued
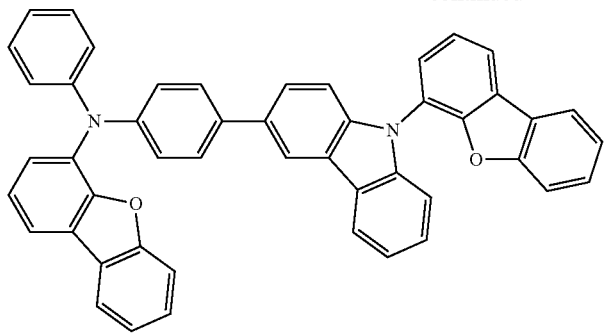
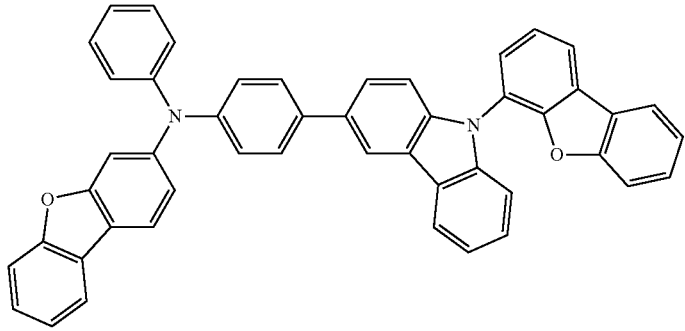
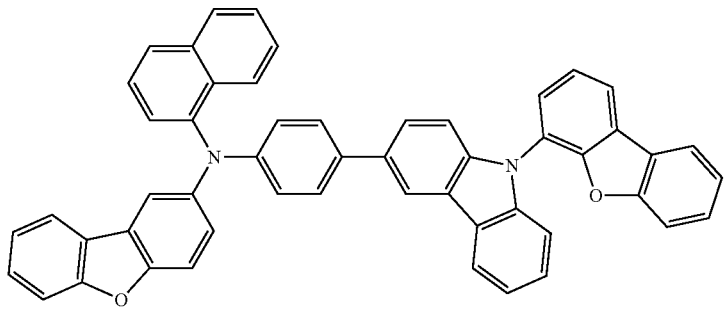
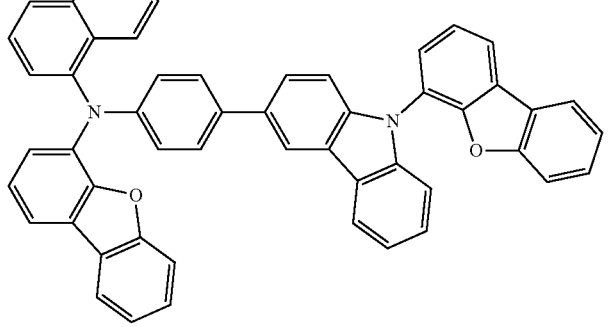
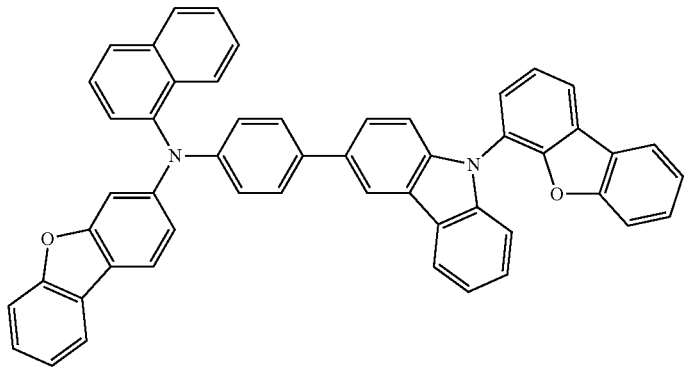

-continued
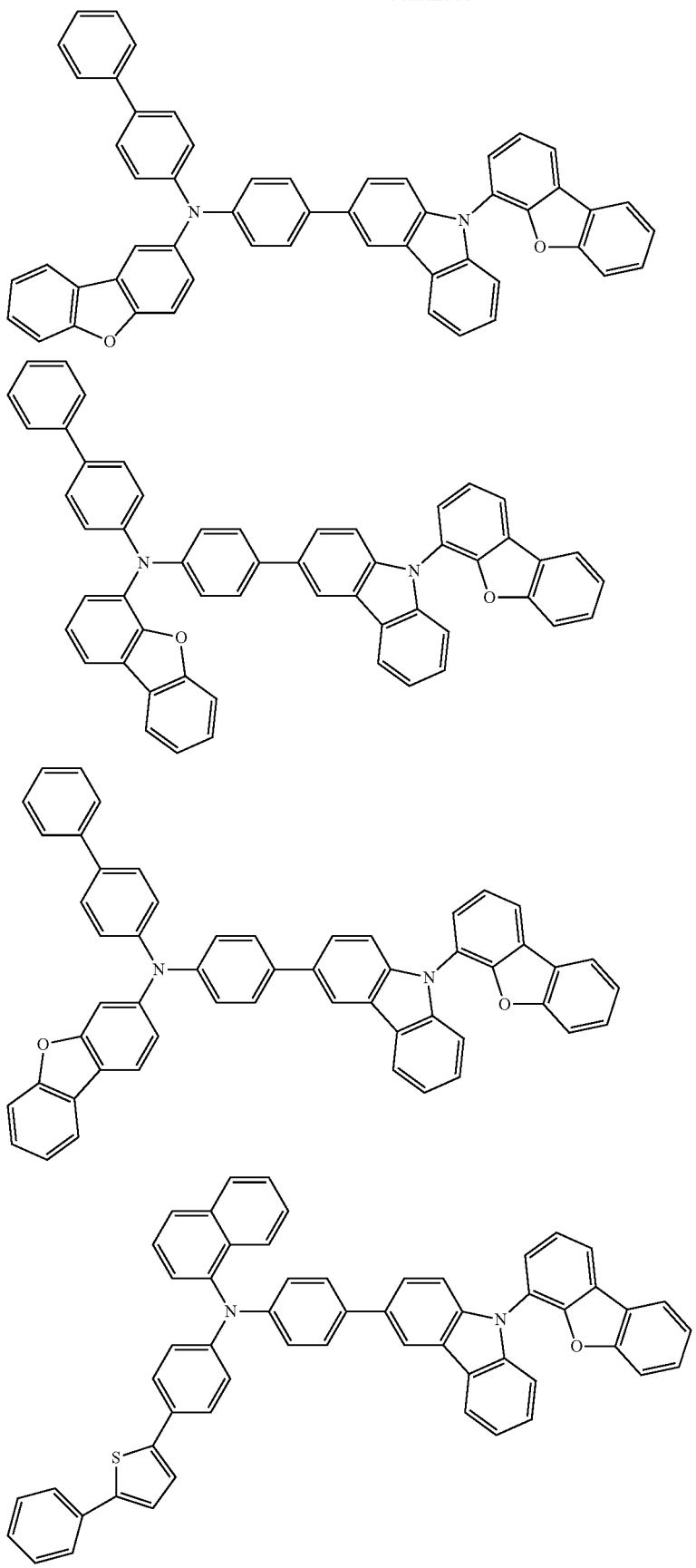

-continued
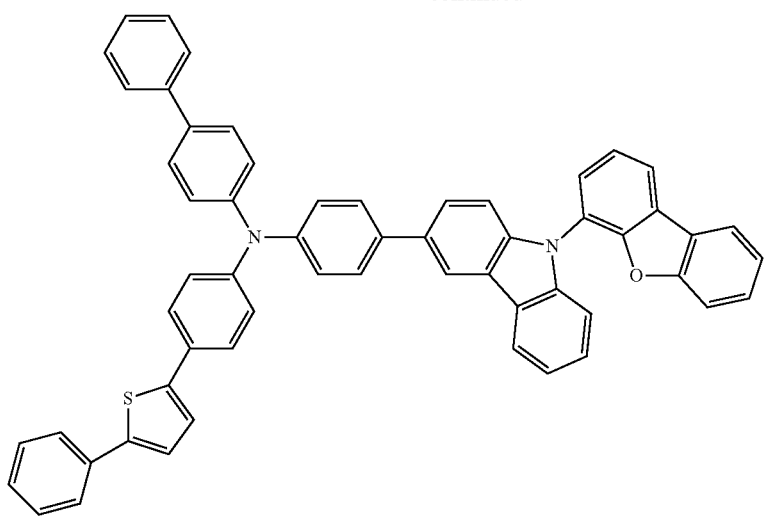
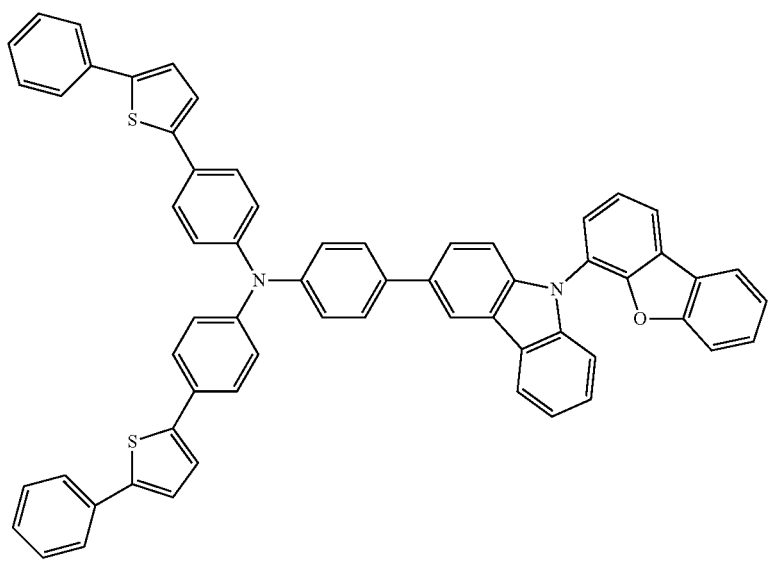
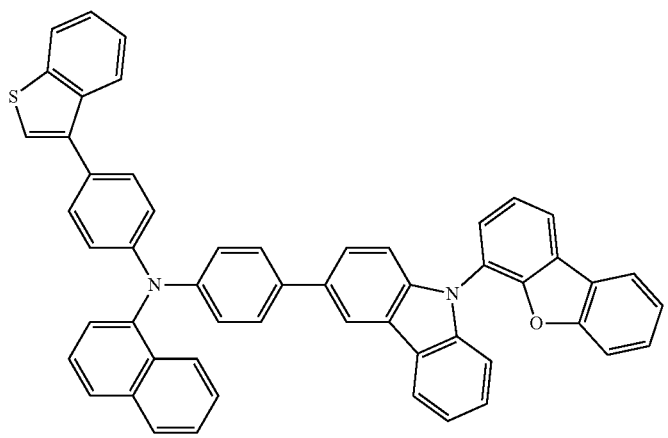

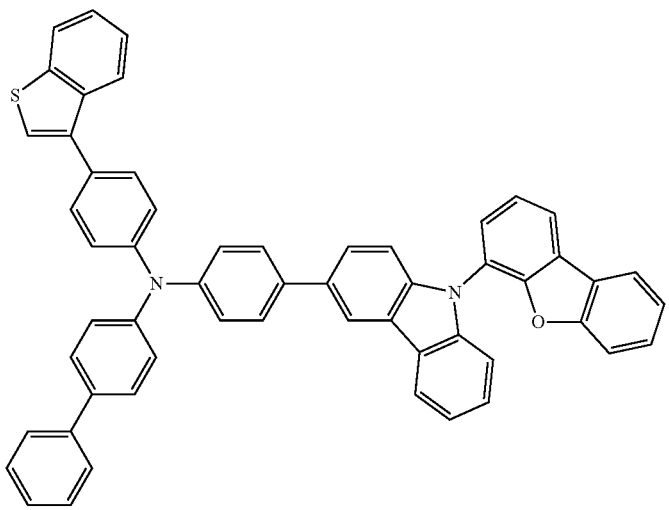
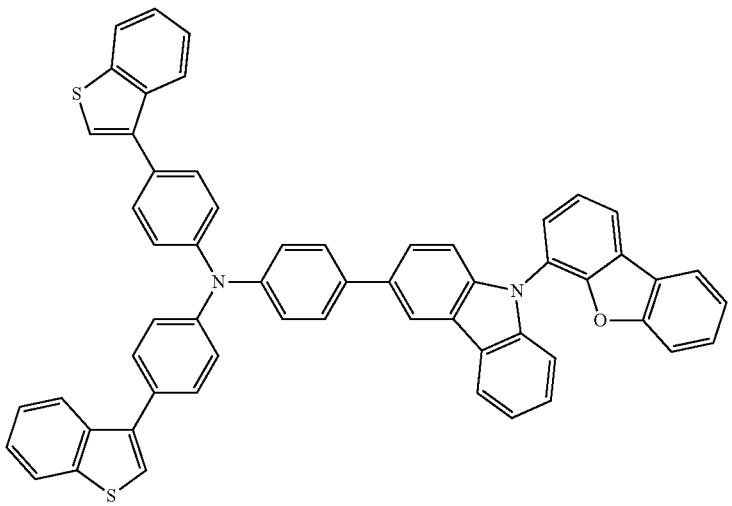
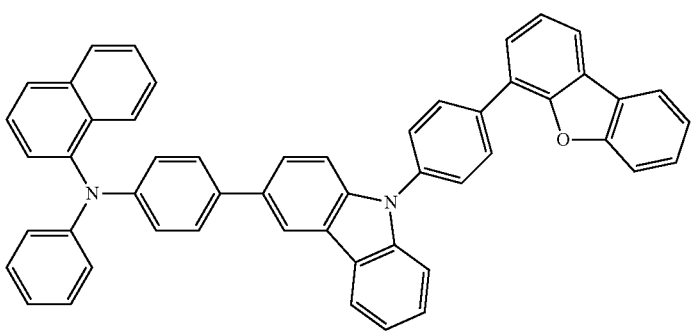
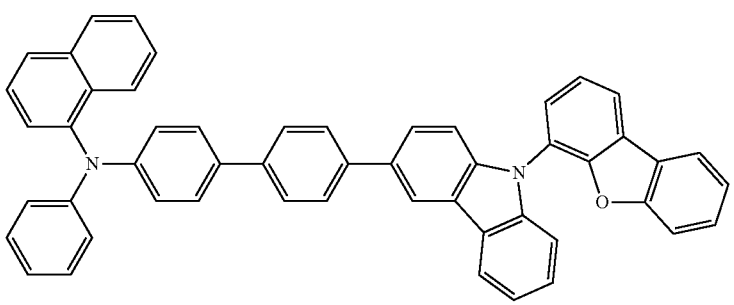

-continued
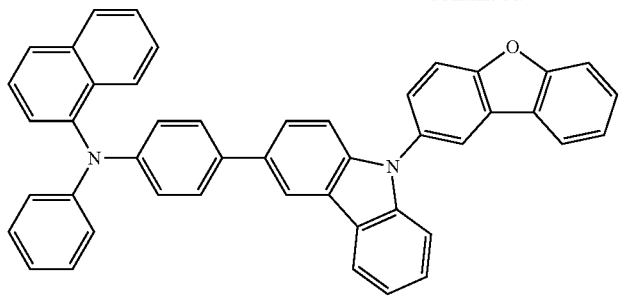
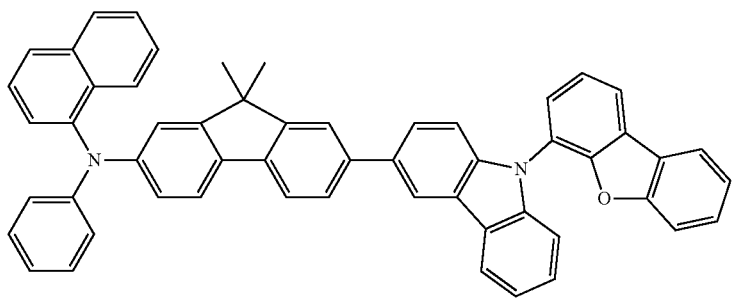
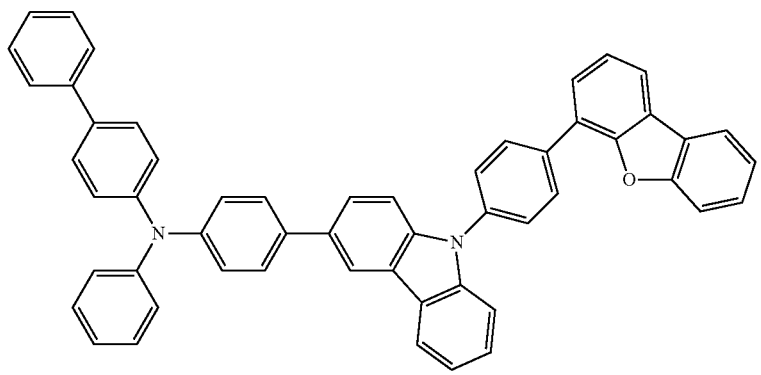
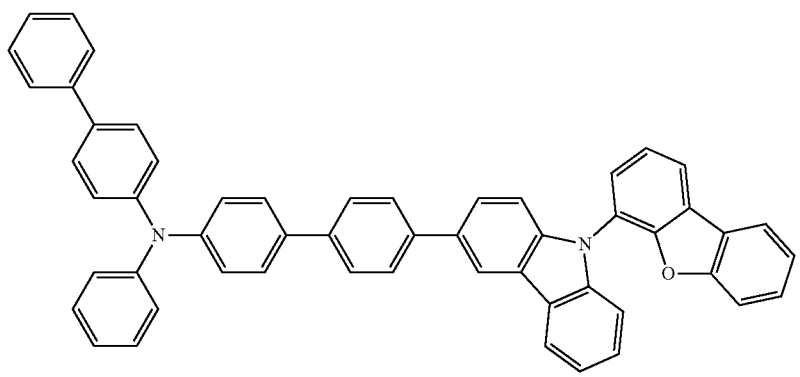

-continued
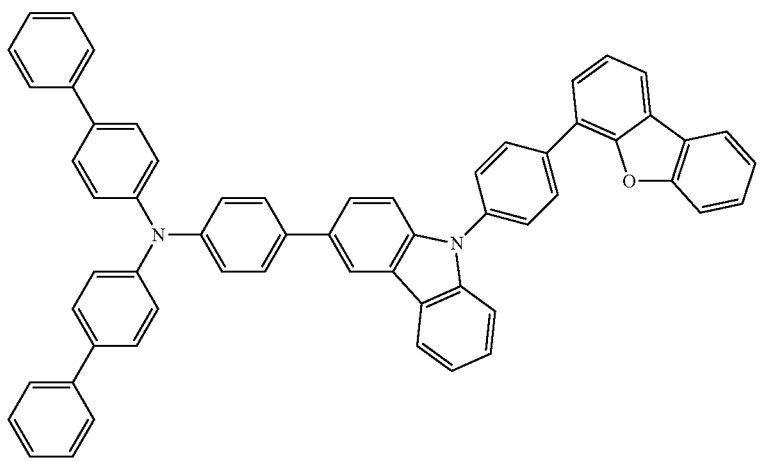
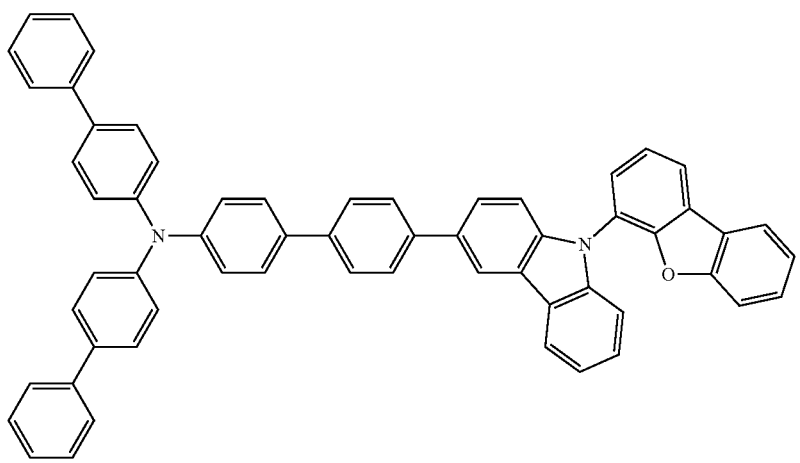
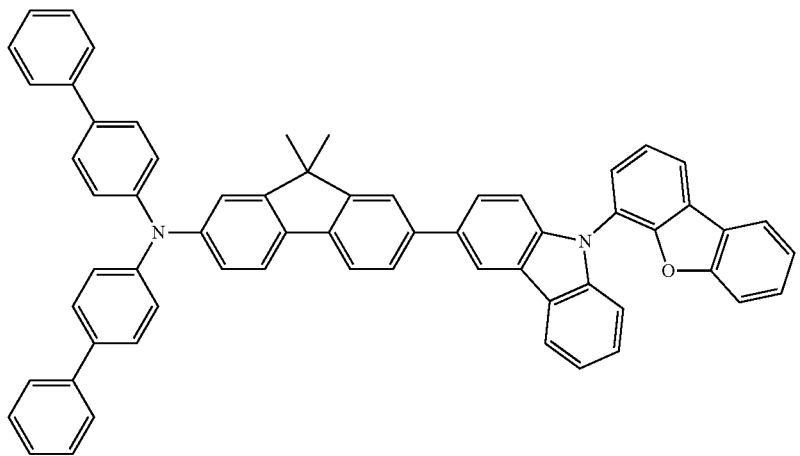

-continued
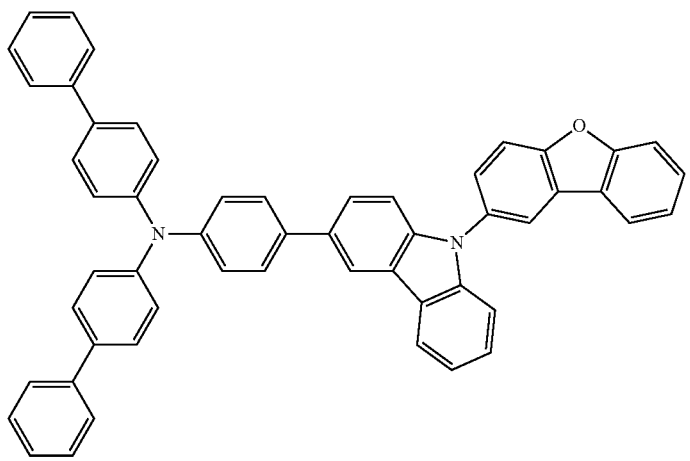
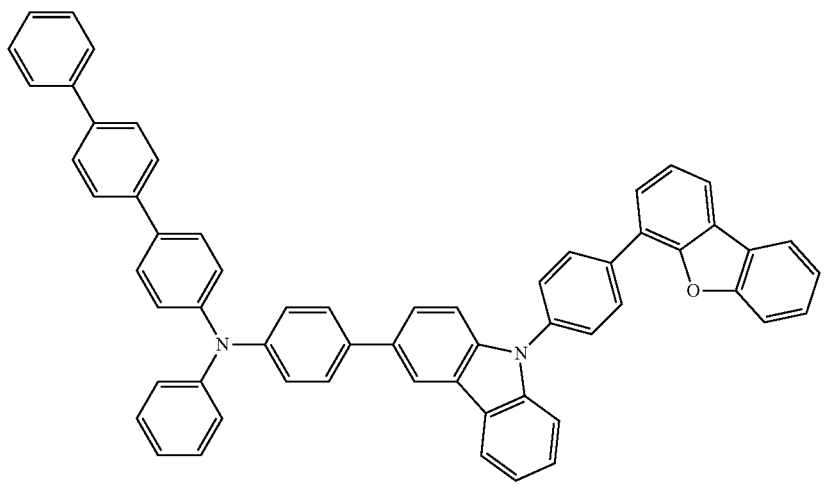
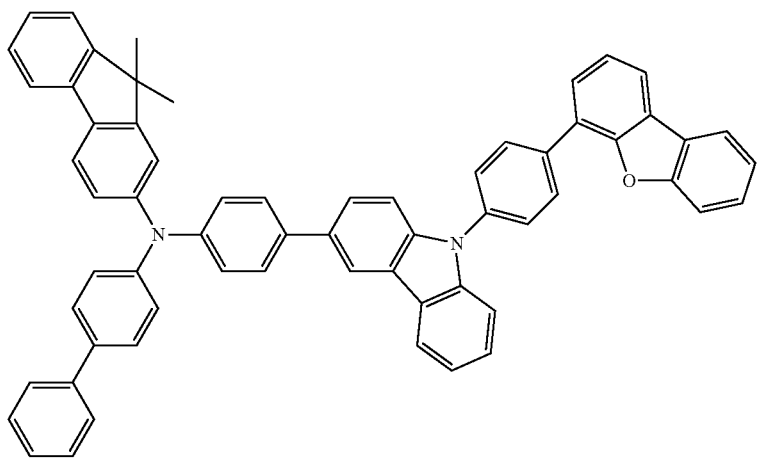

-continued
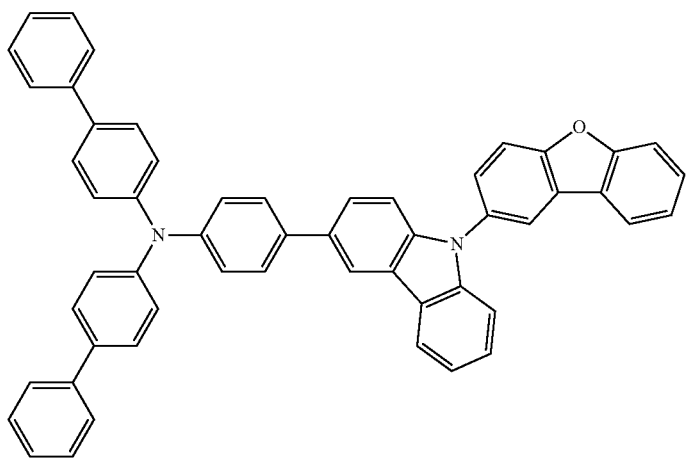
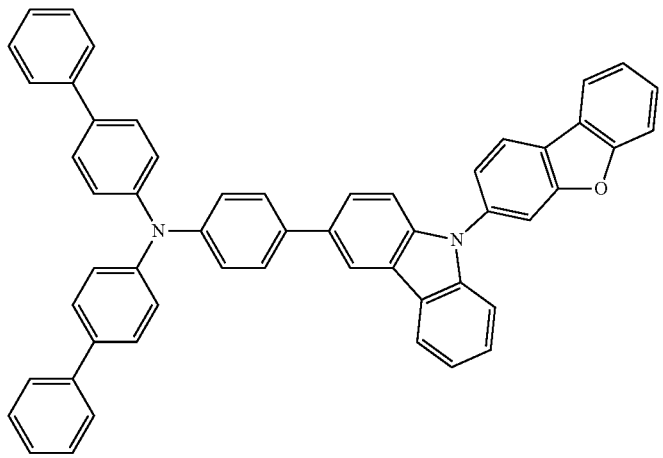
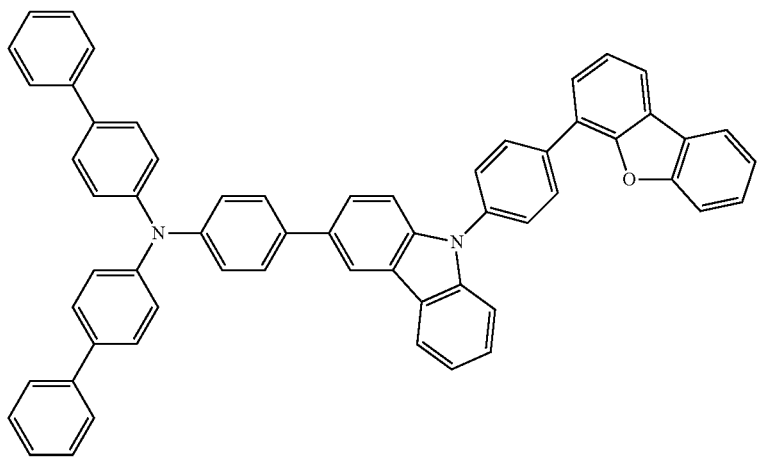

-continued
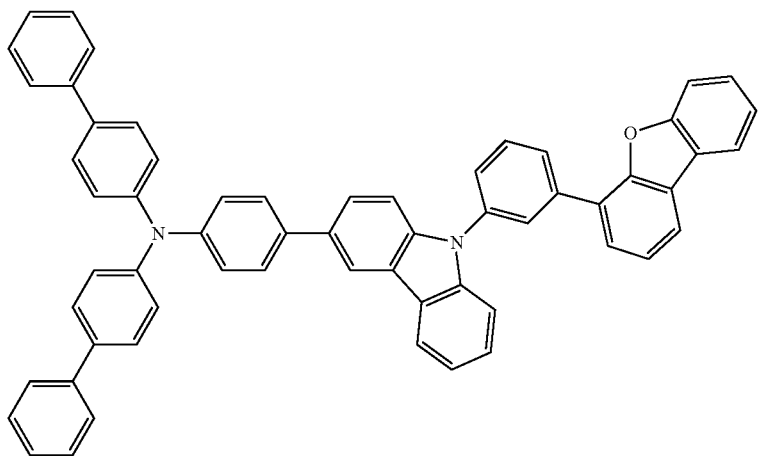
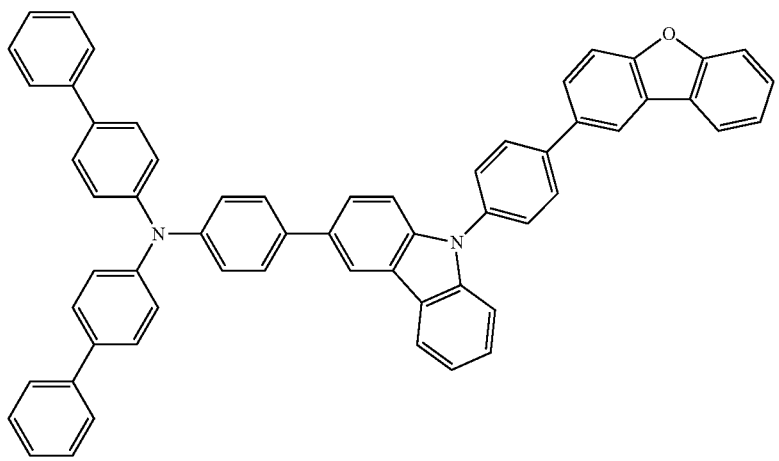
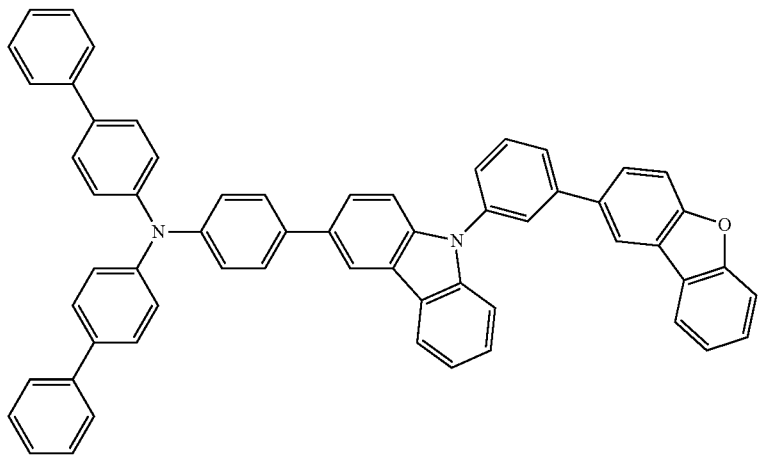

-continued
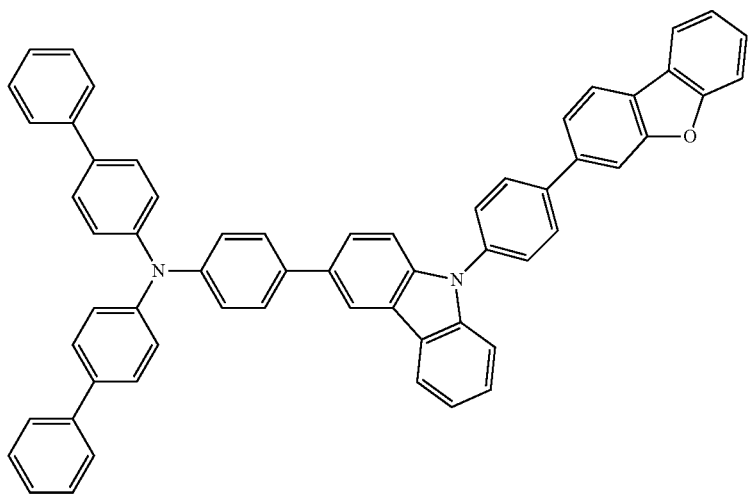
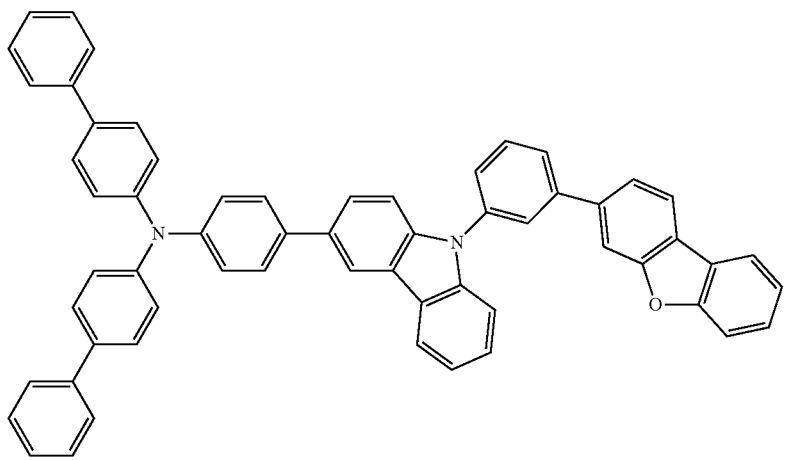
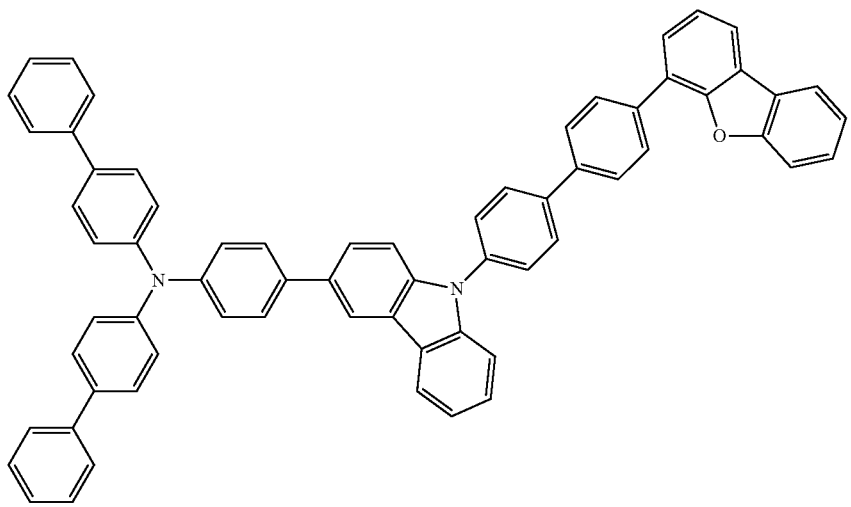

-continued
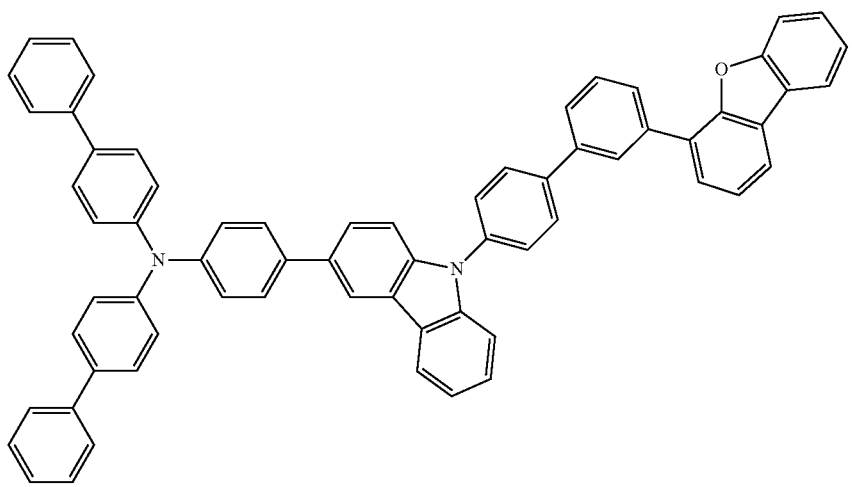
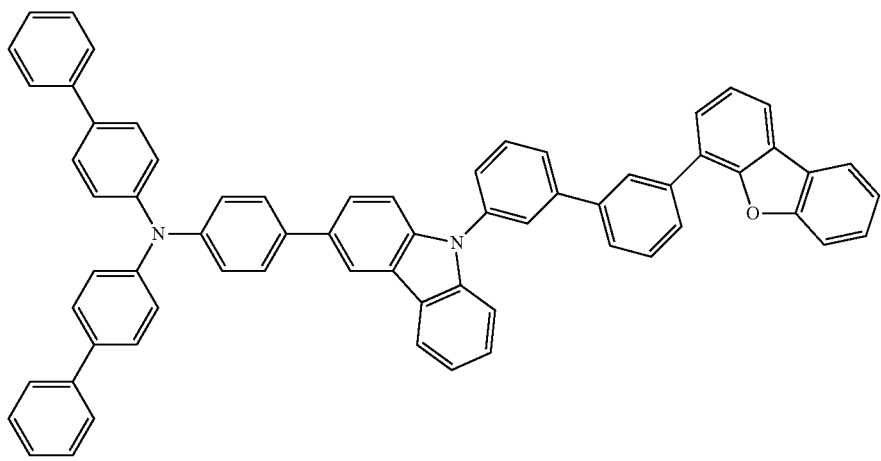
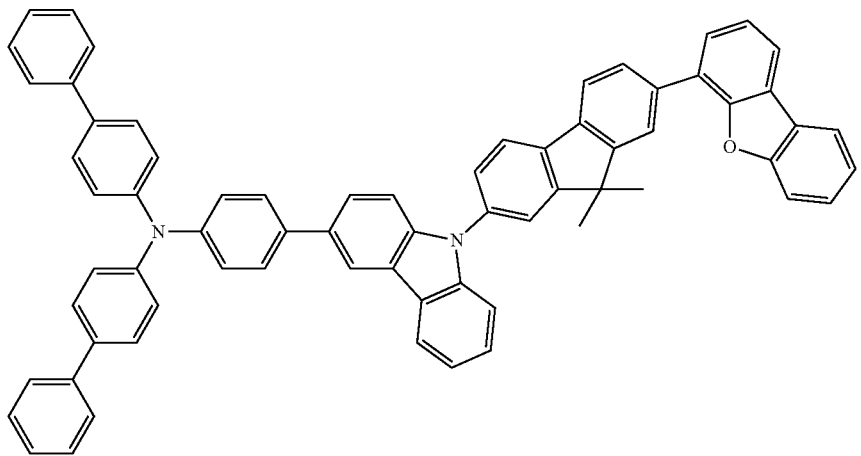

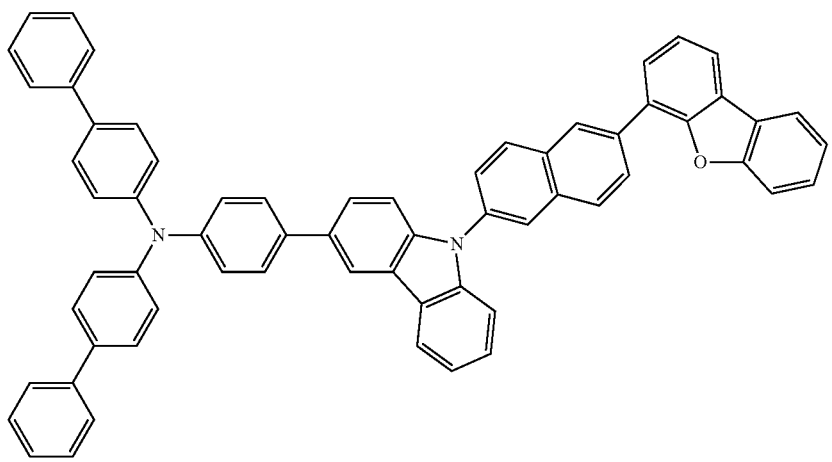
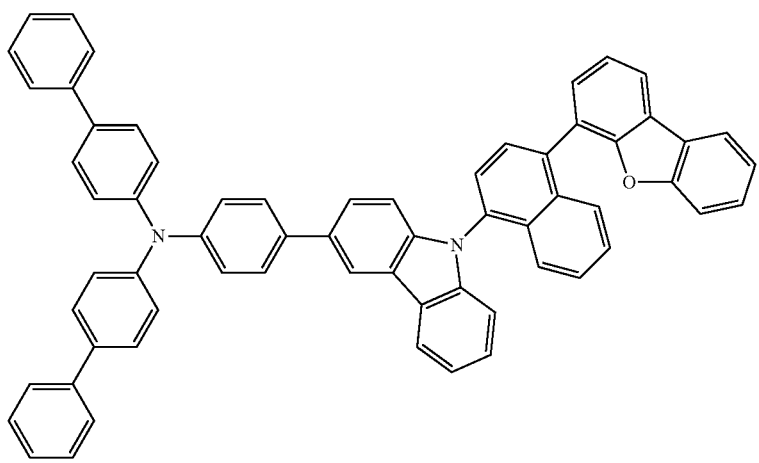
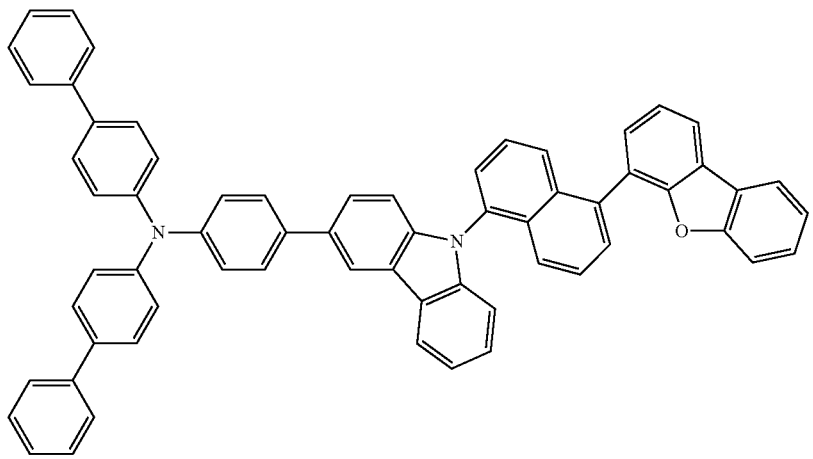

-continued
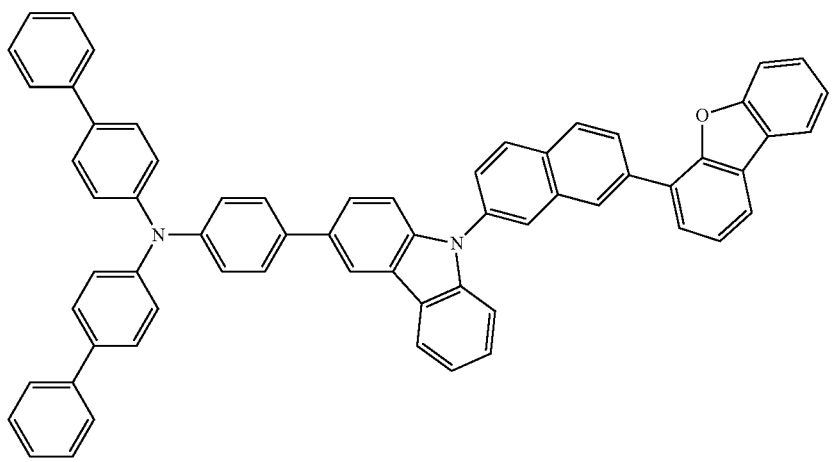
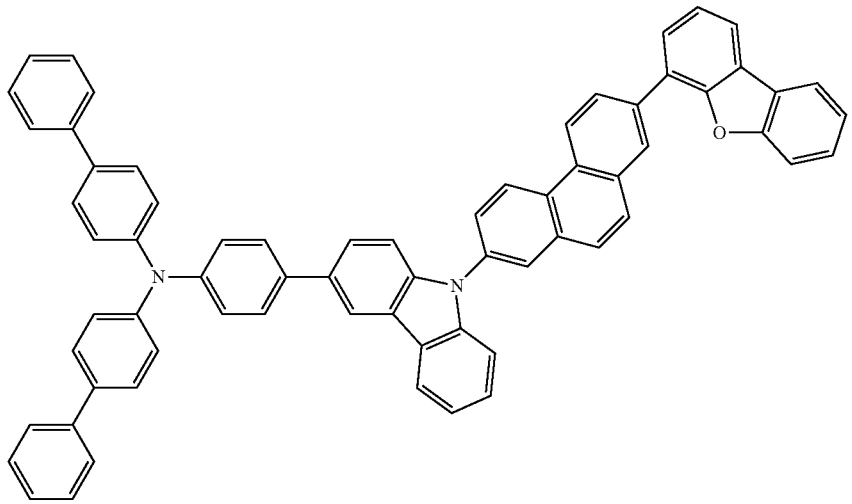
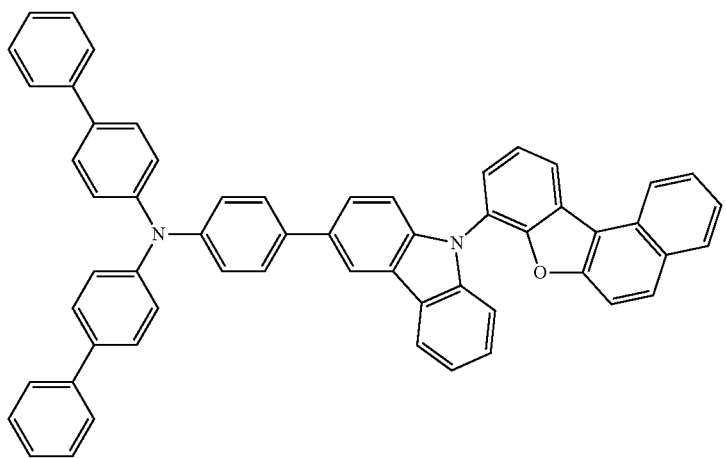

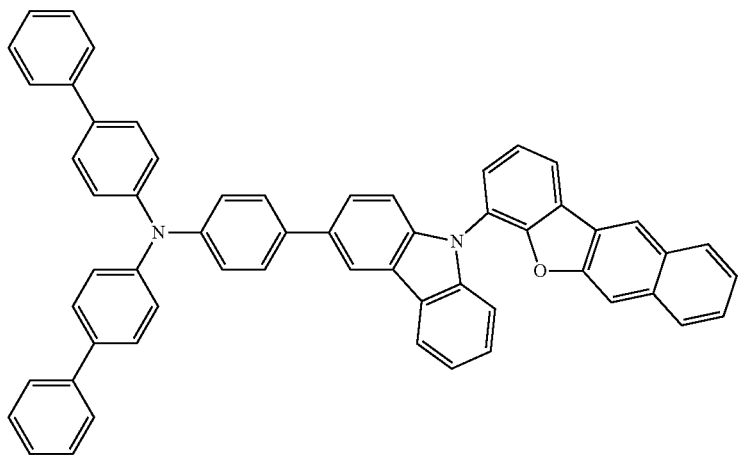
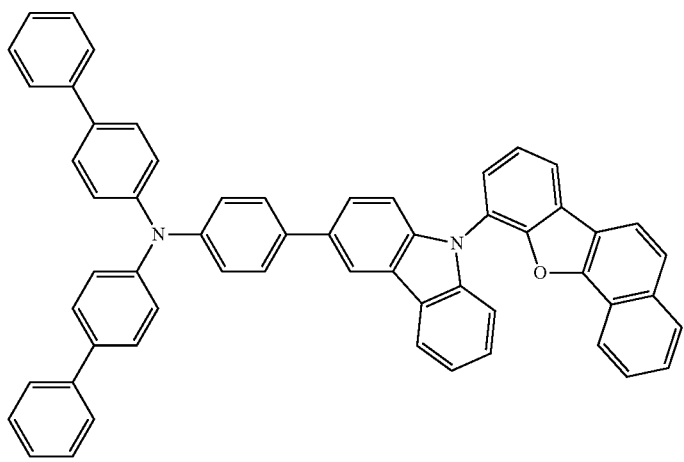
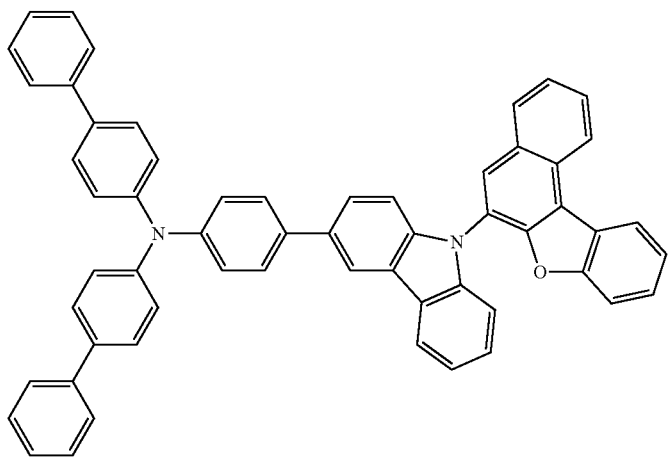

-continued
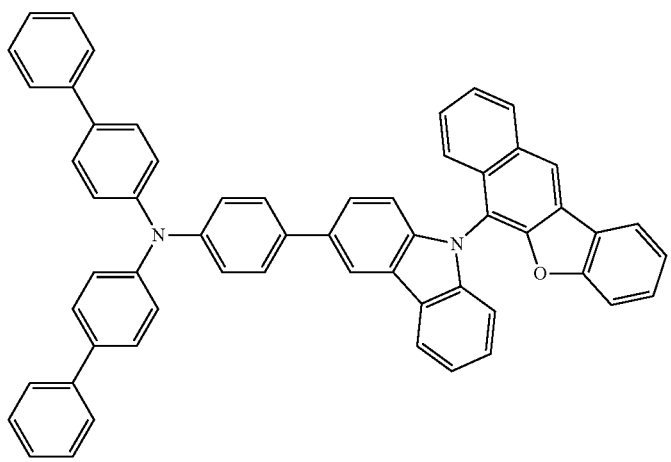
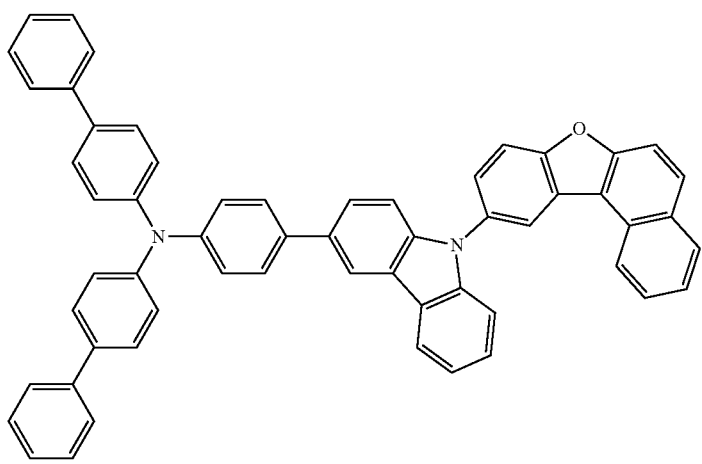
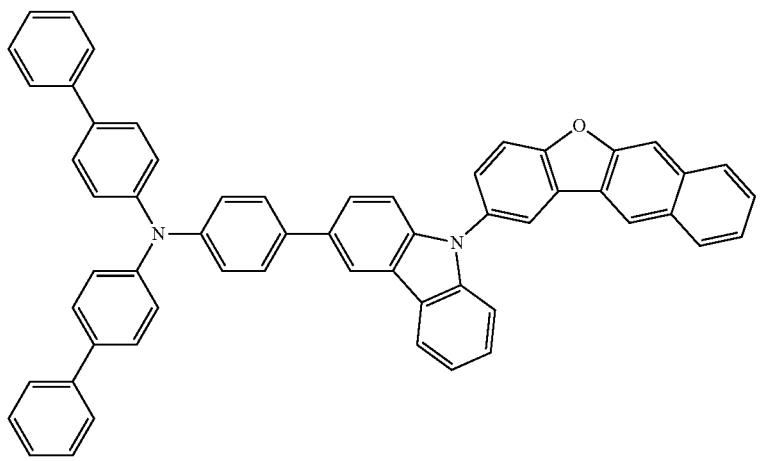

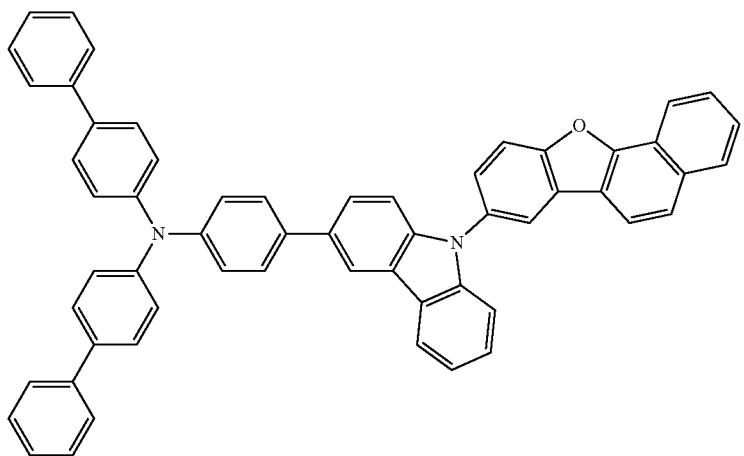
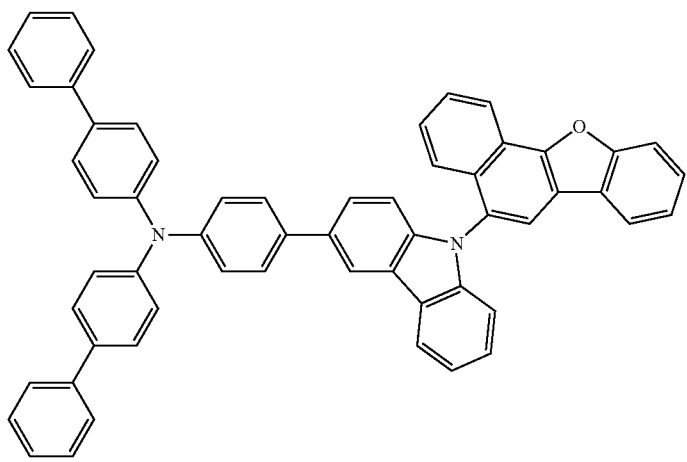
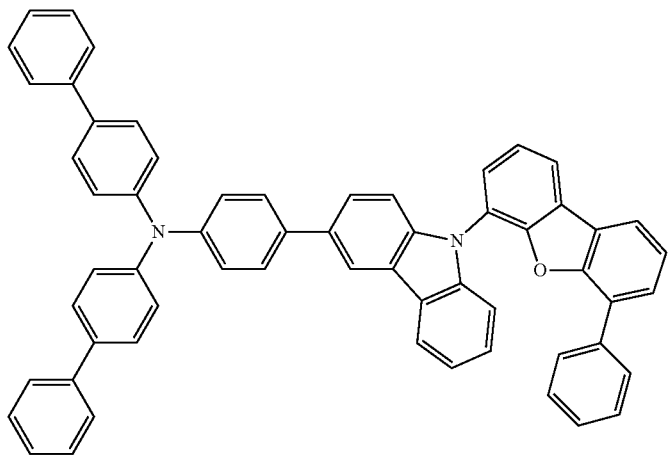

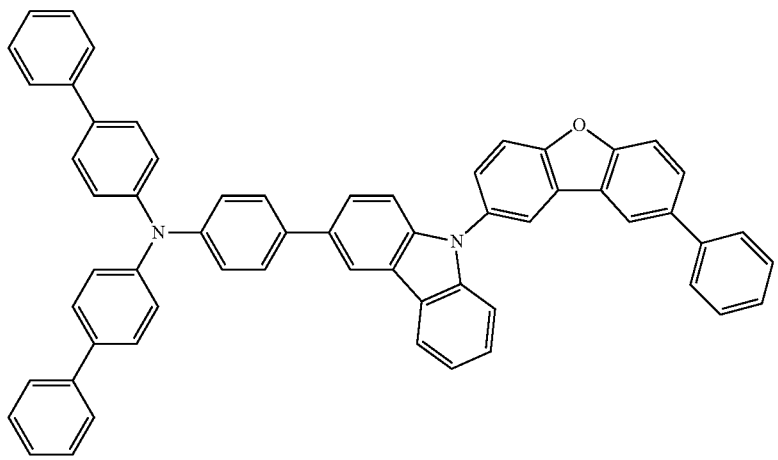
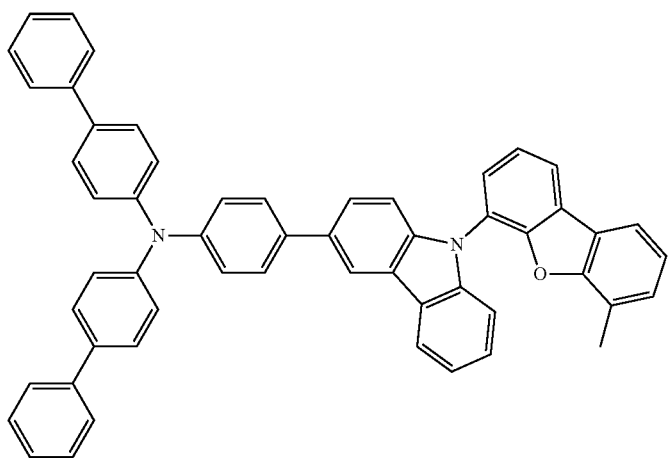
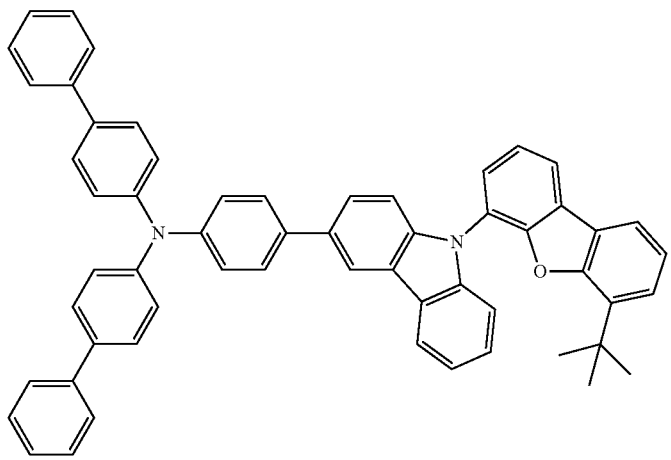

-continued
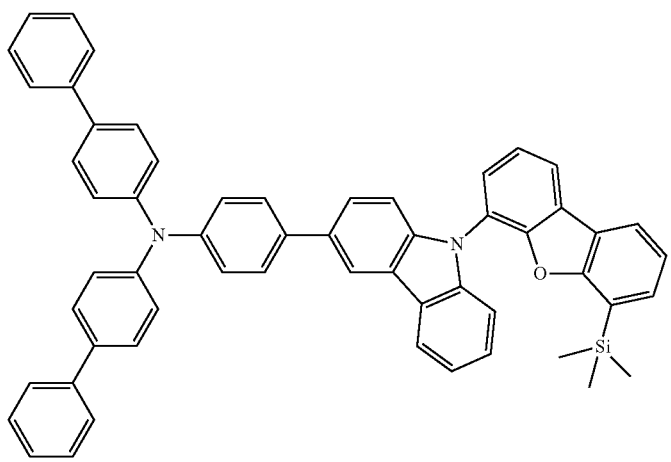
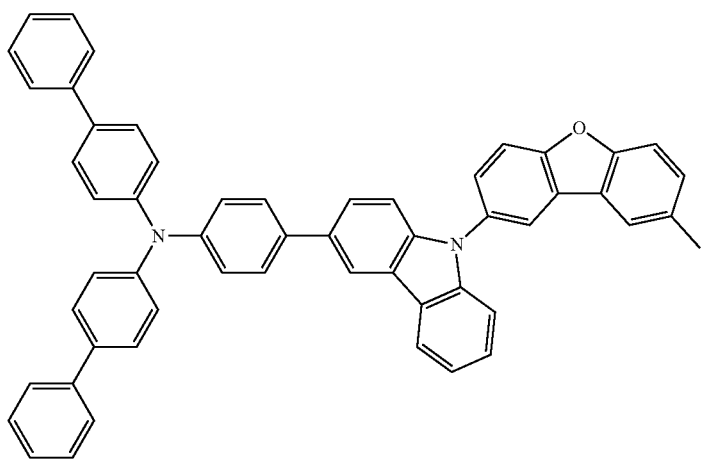
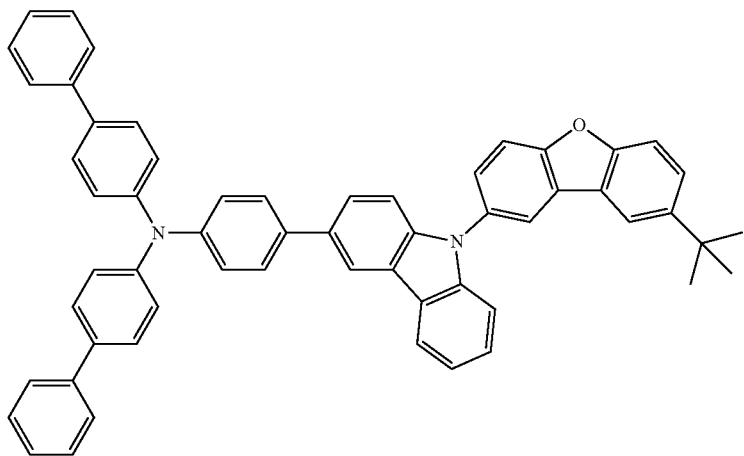

-continued
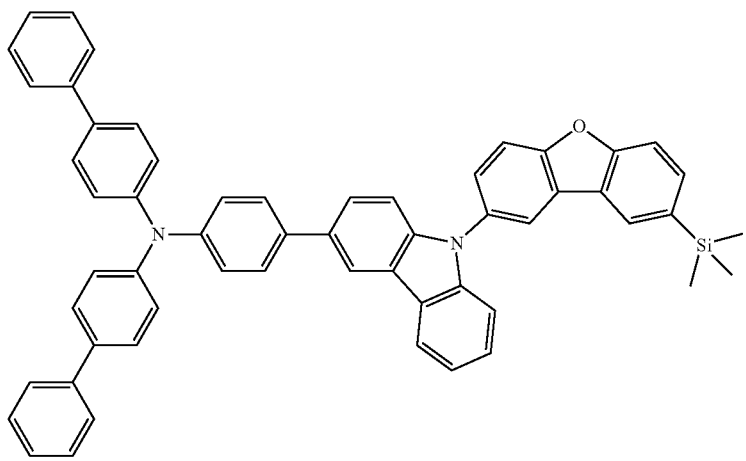
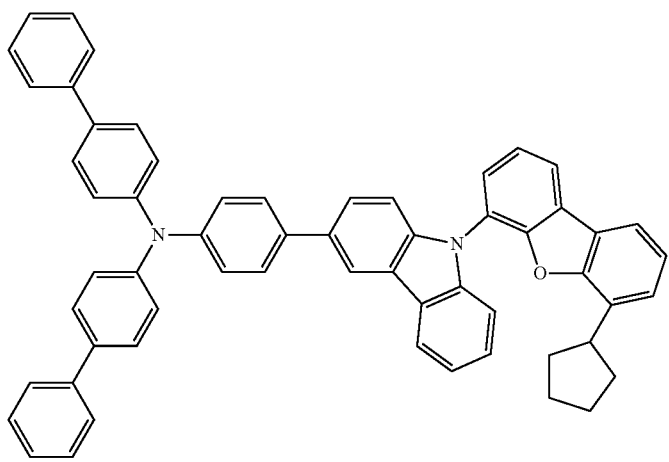
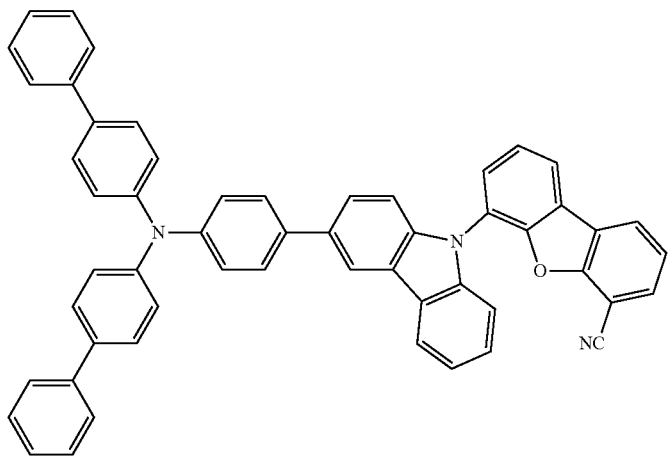

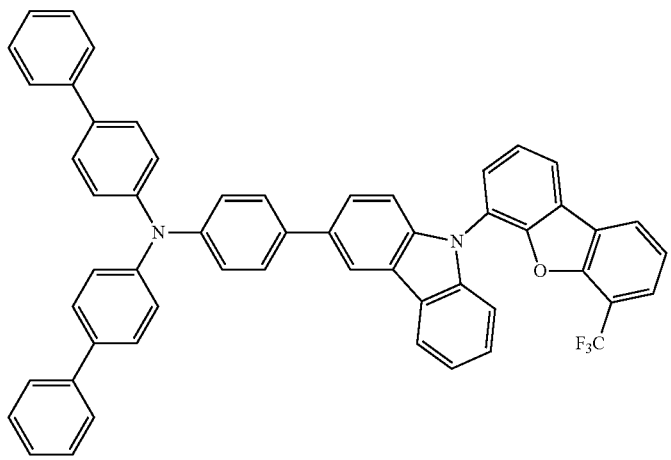
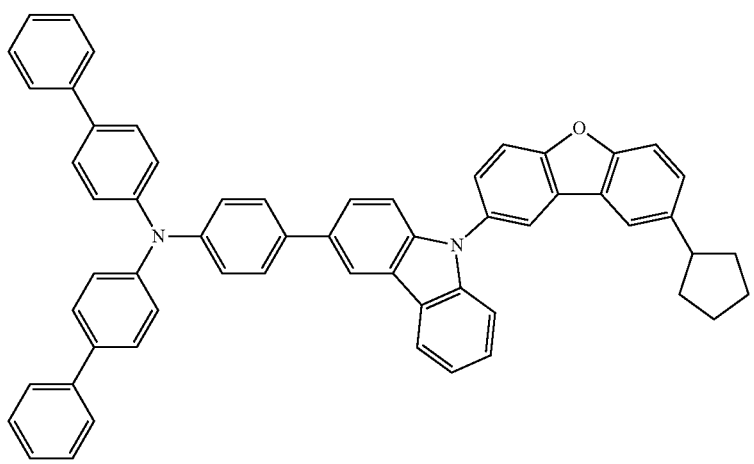
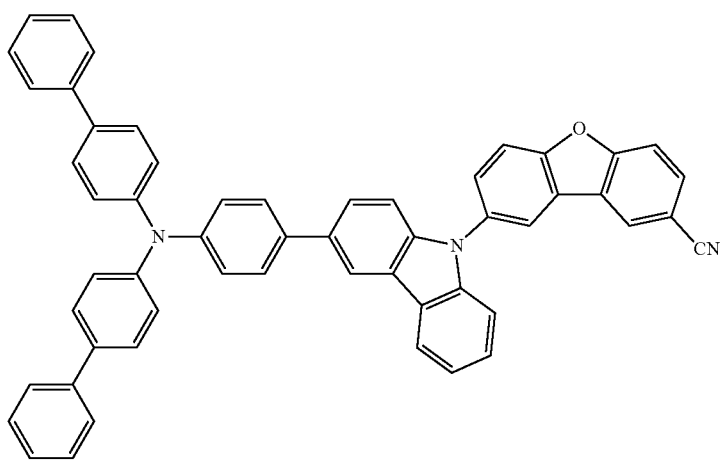

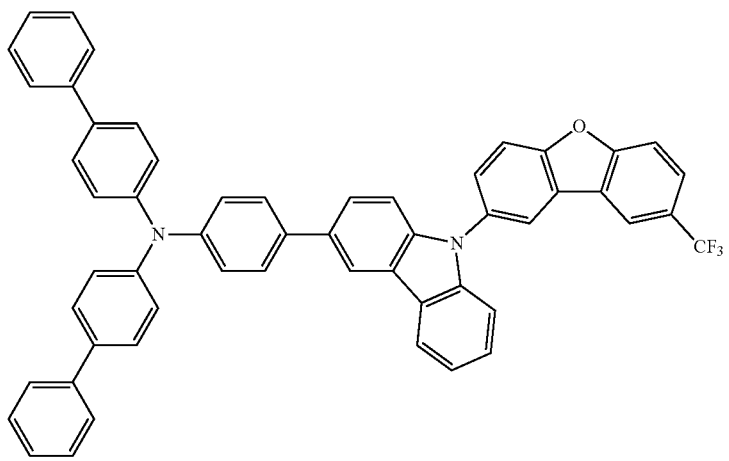
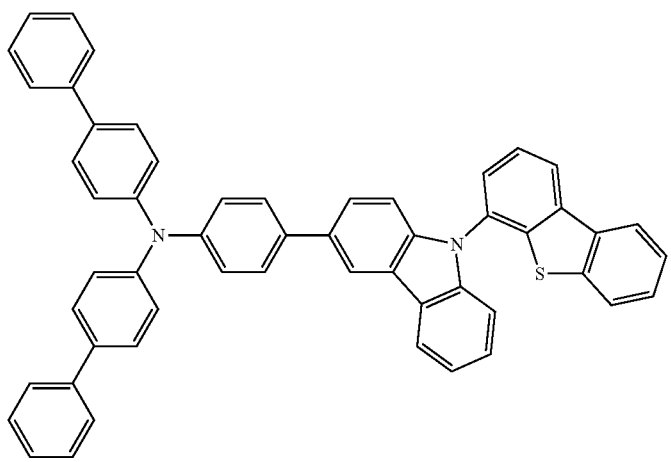
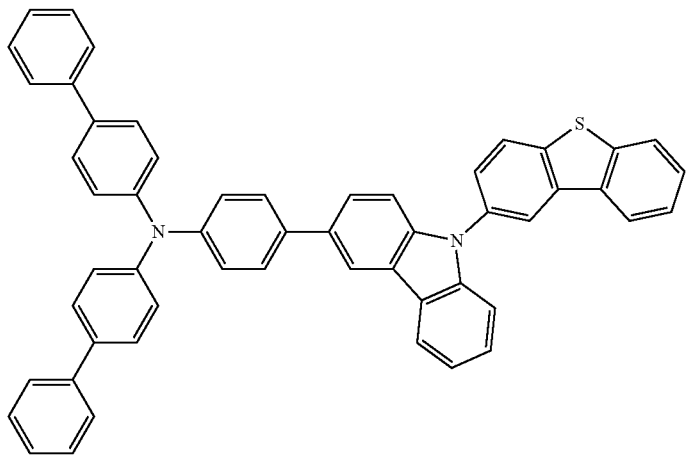

-continued
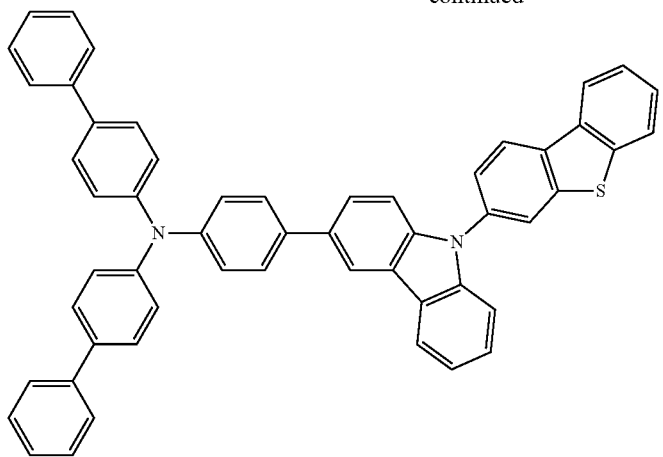
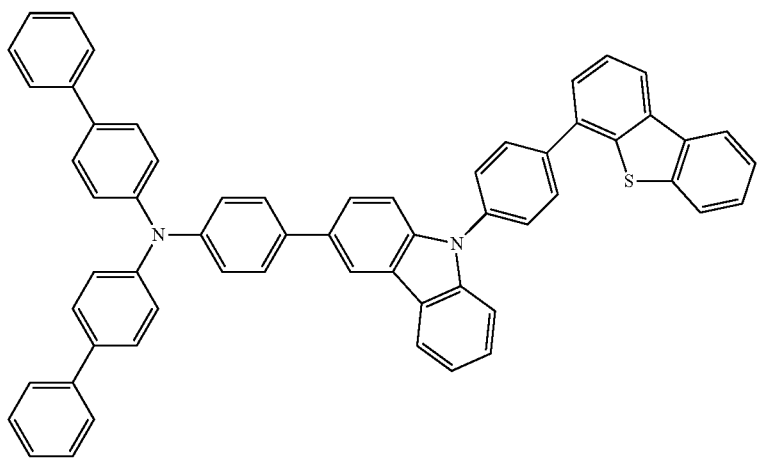
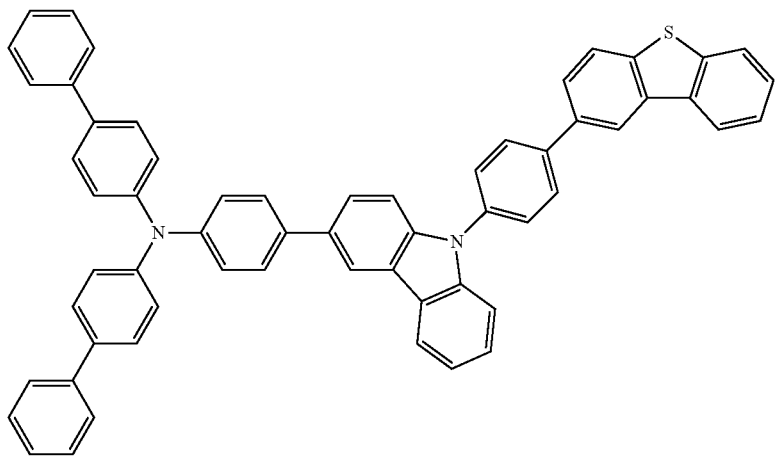

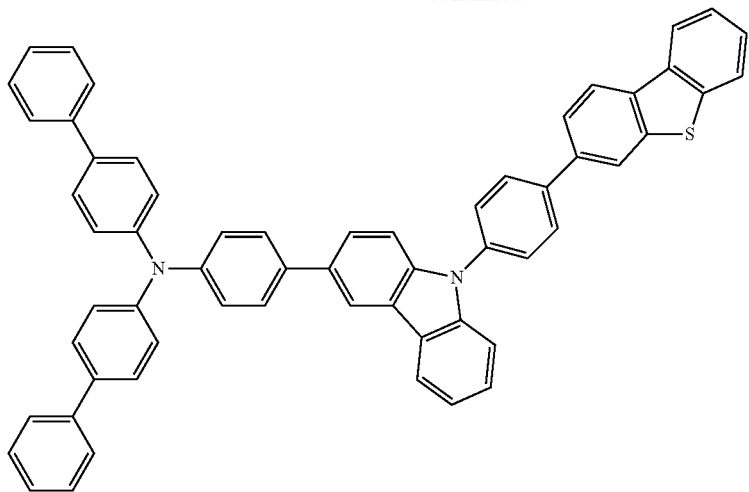
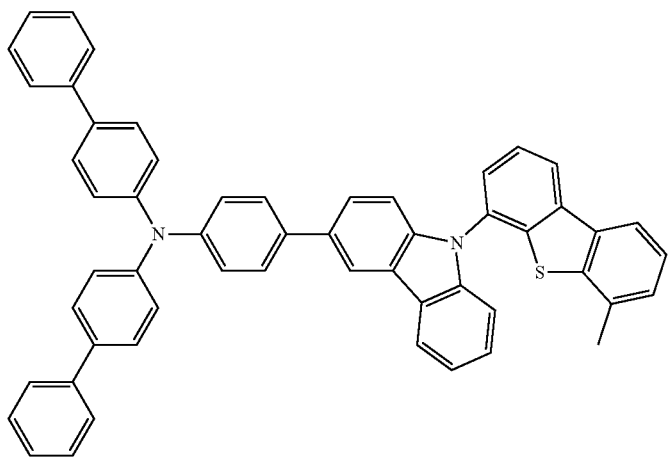
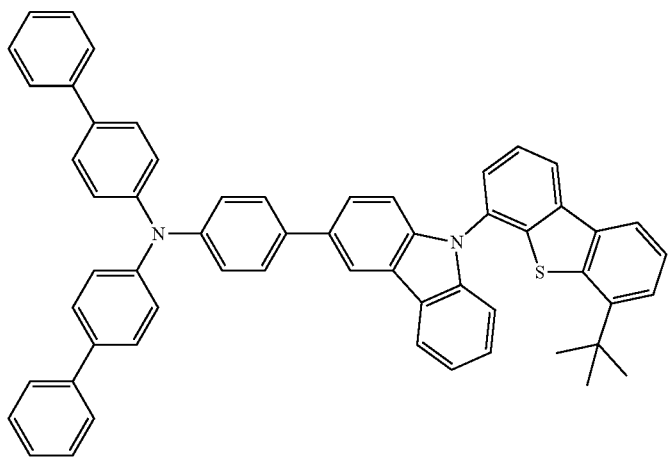

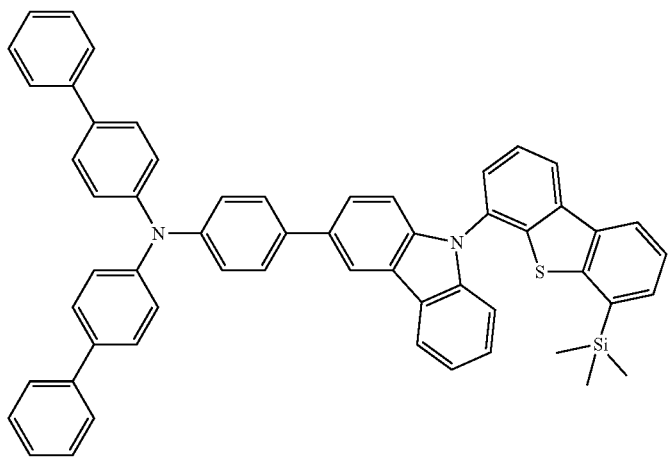
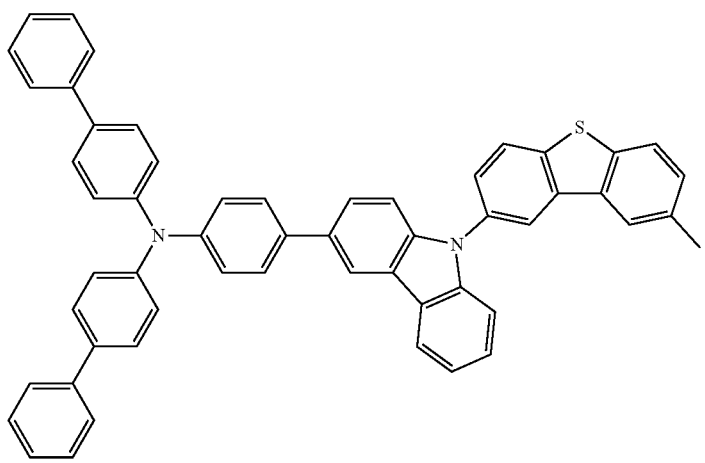
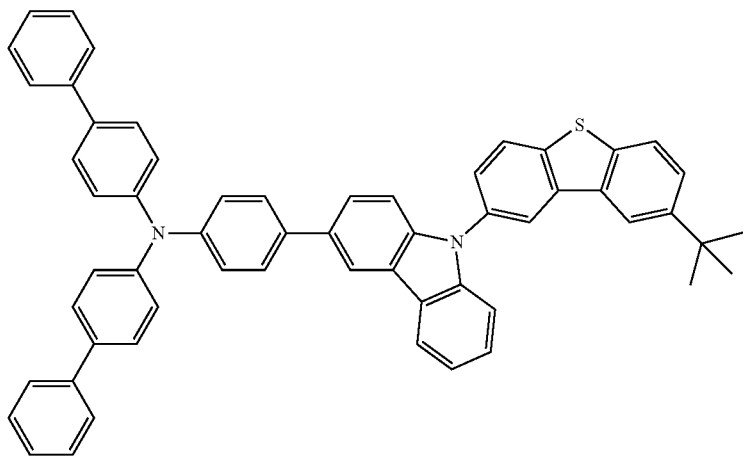

-continued
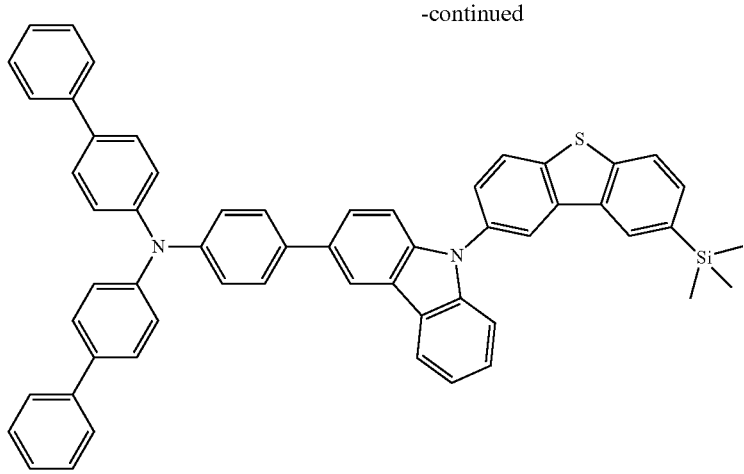
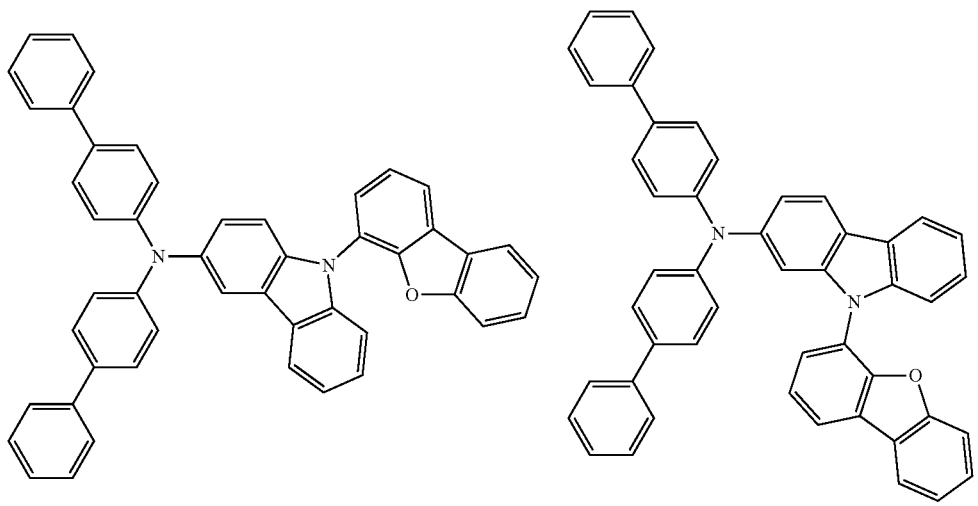
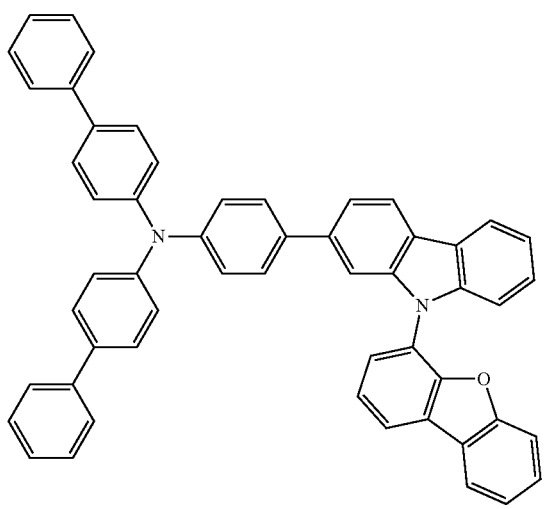

-continued
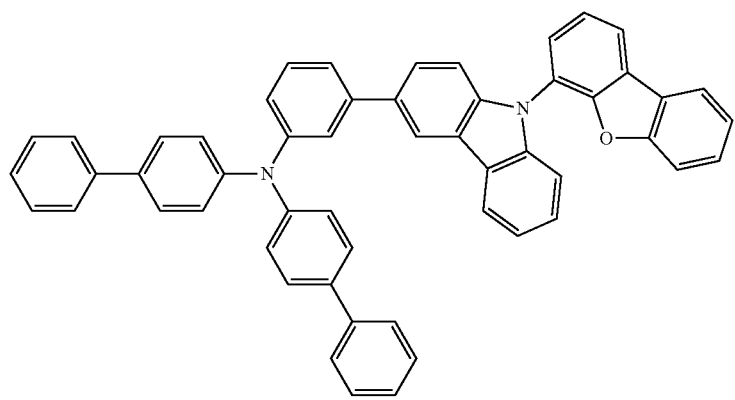
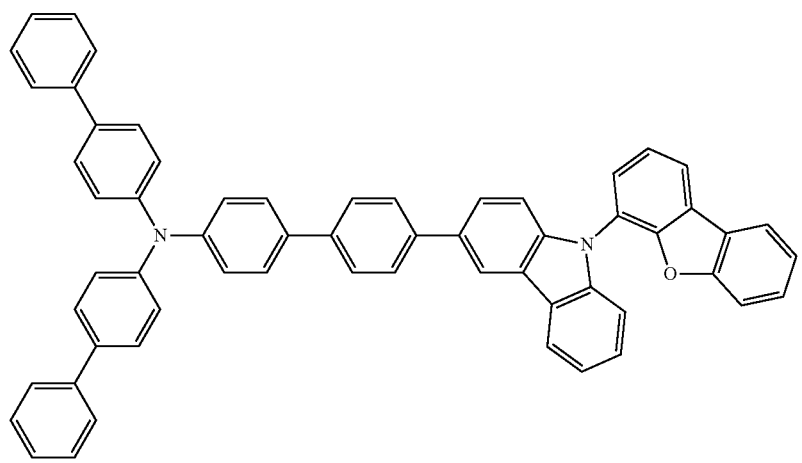
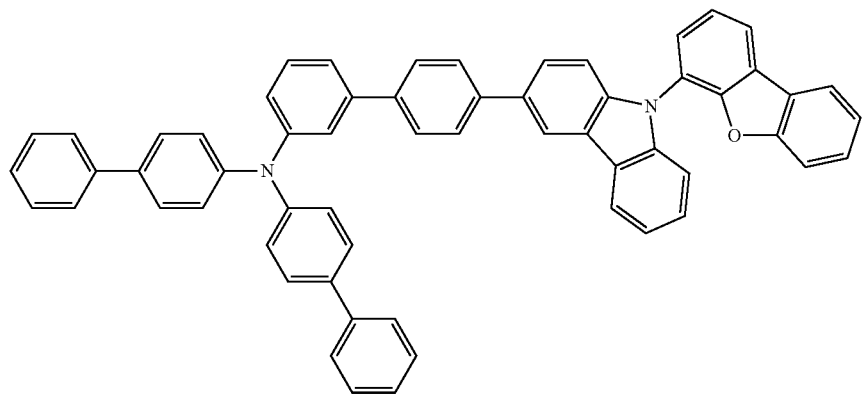
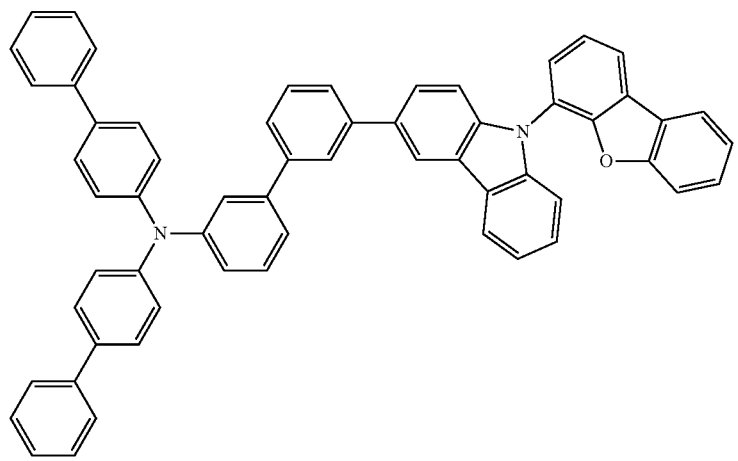

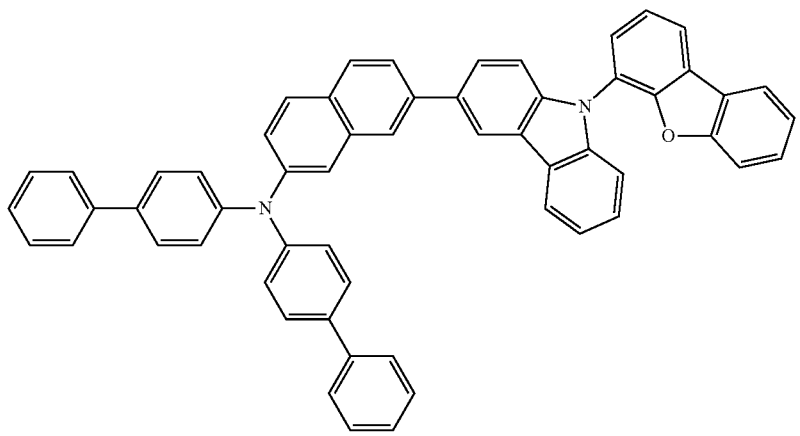
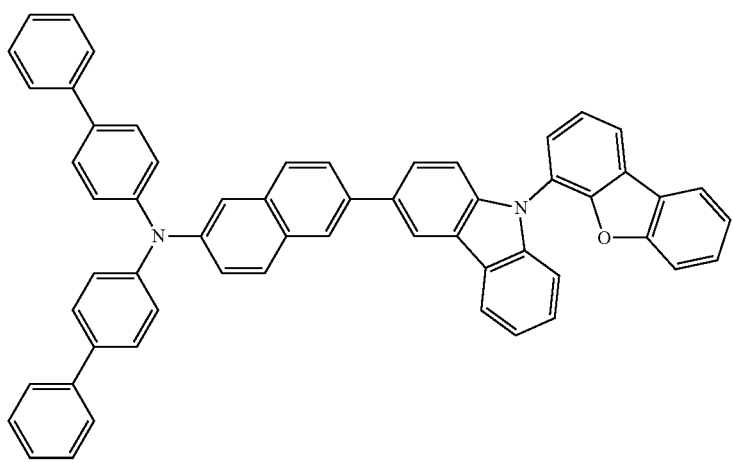
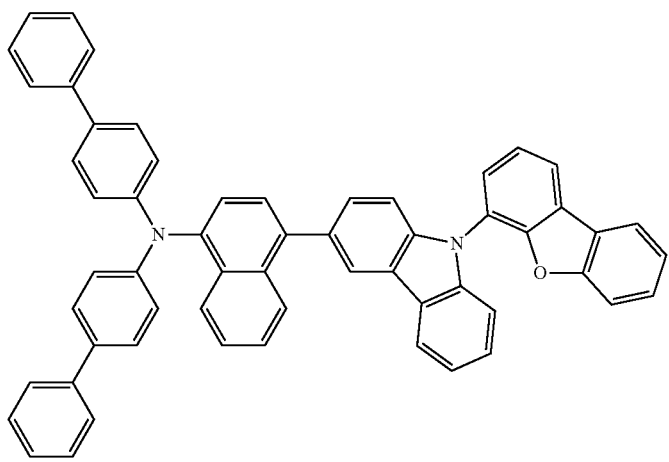

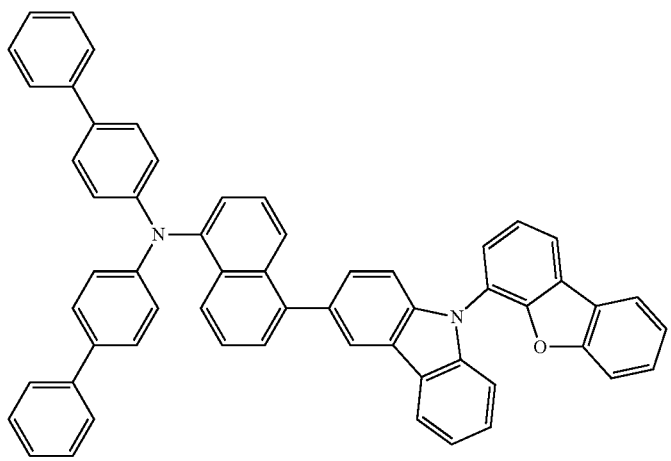
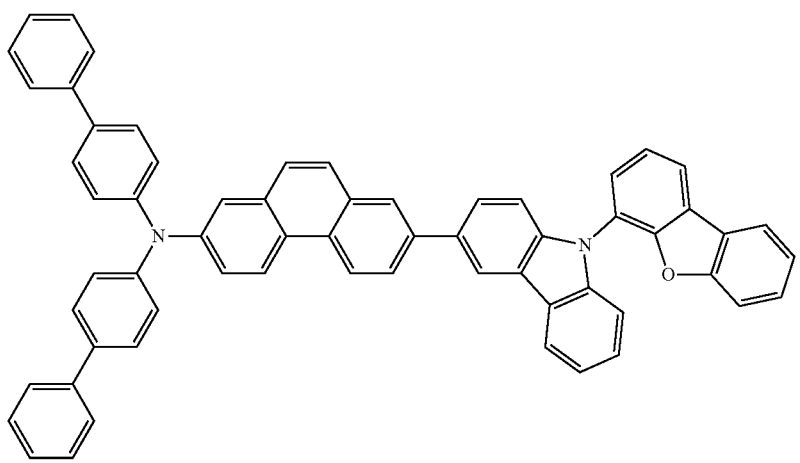
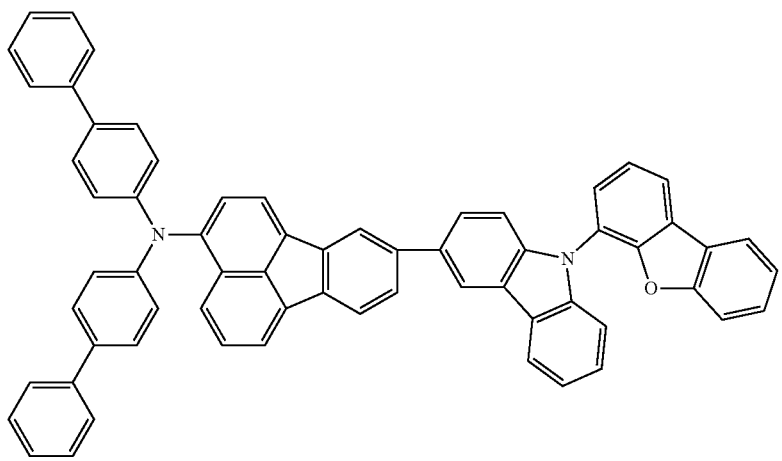

-continued
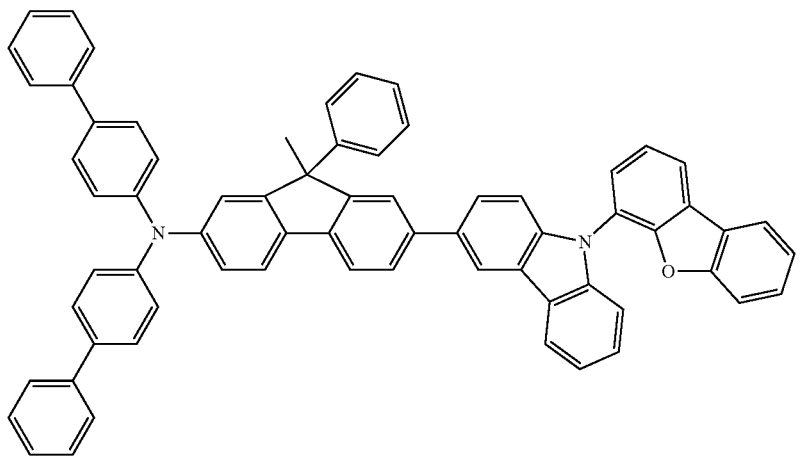
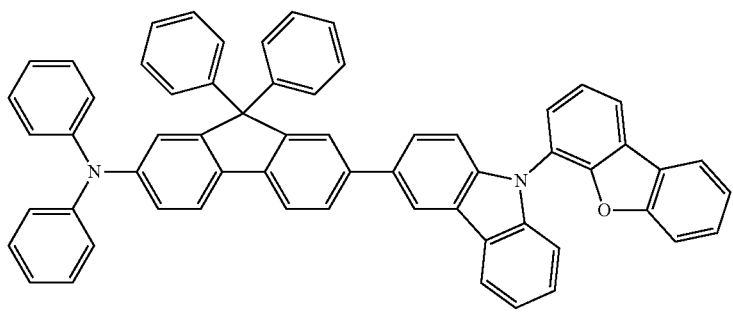
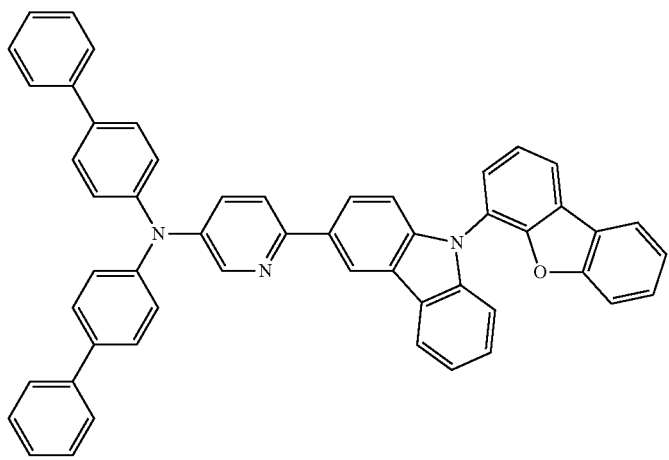
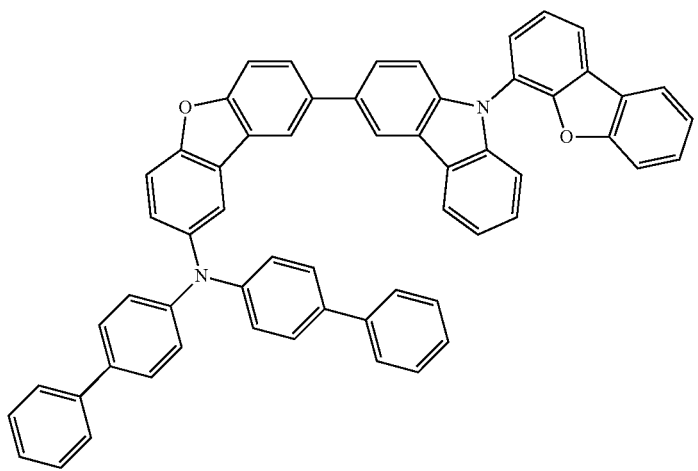

-continued
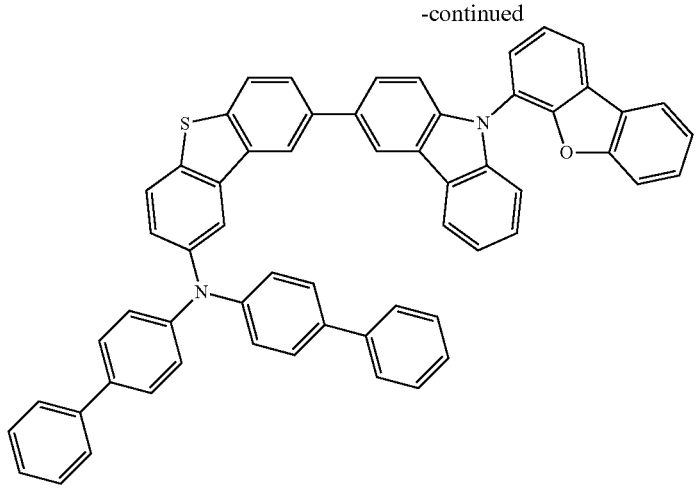
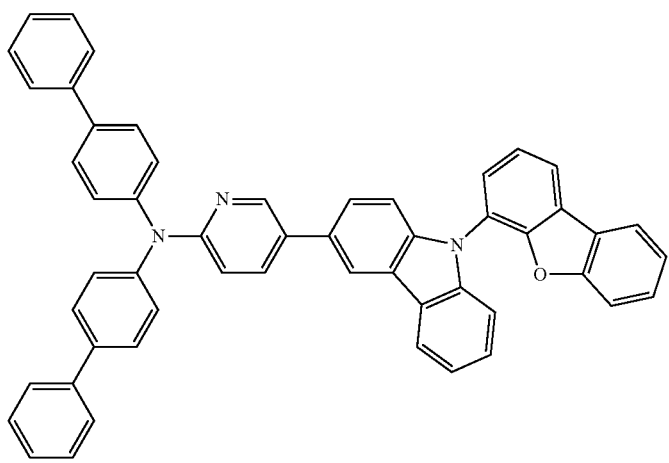
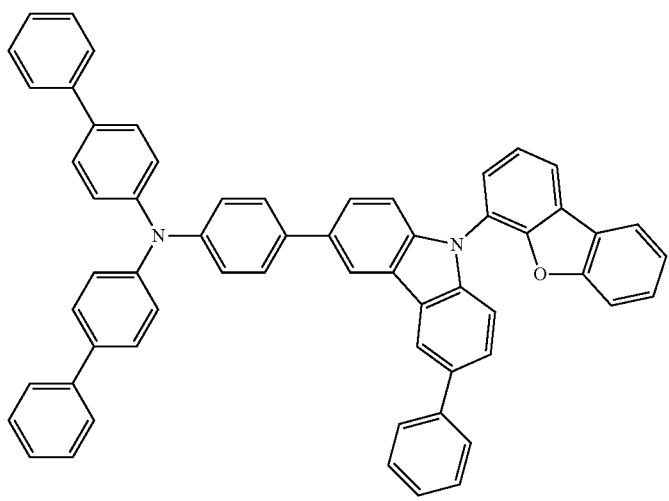

-continued
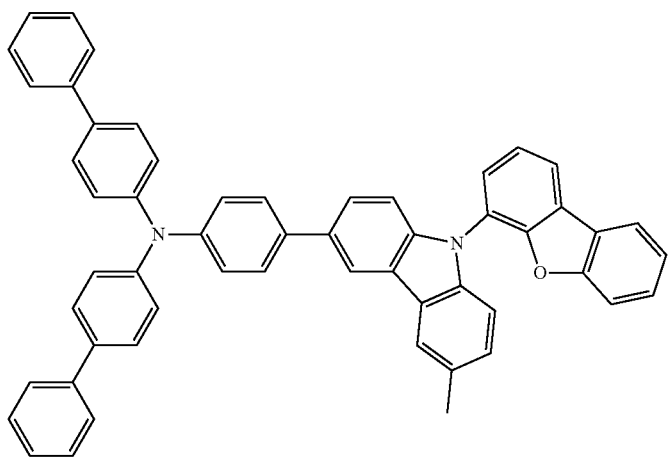
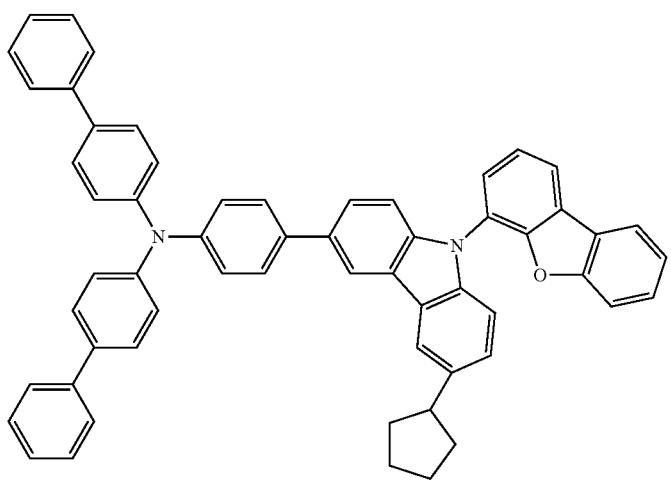
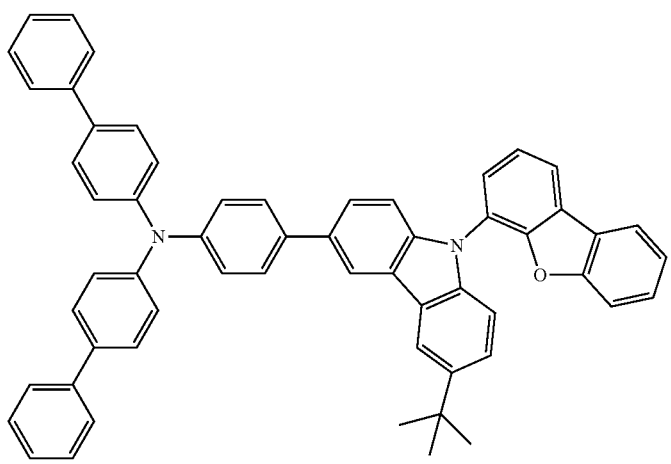

-continued
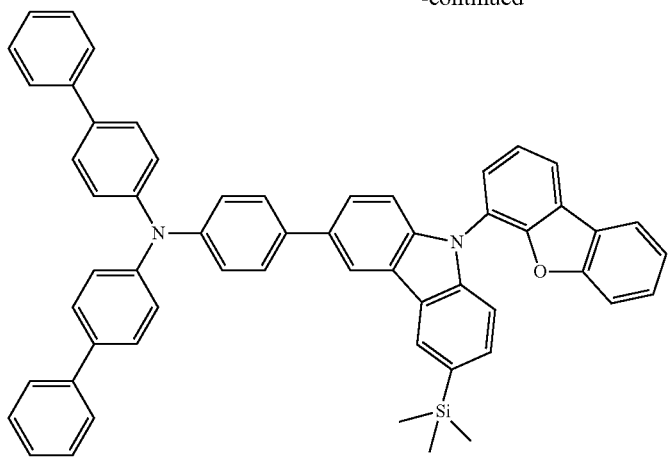
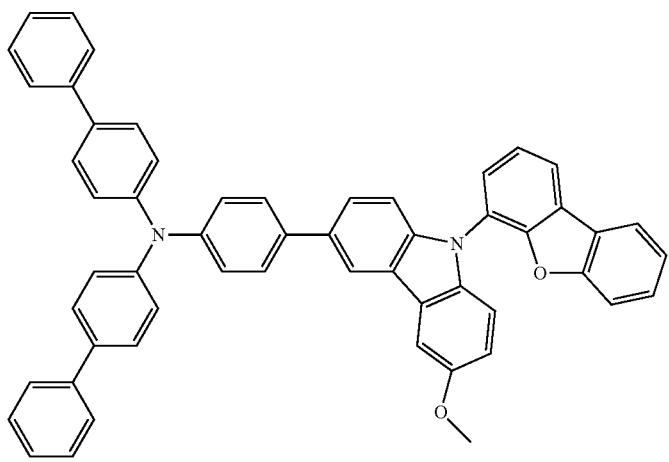
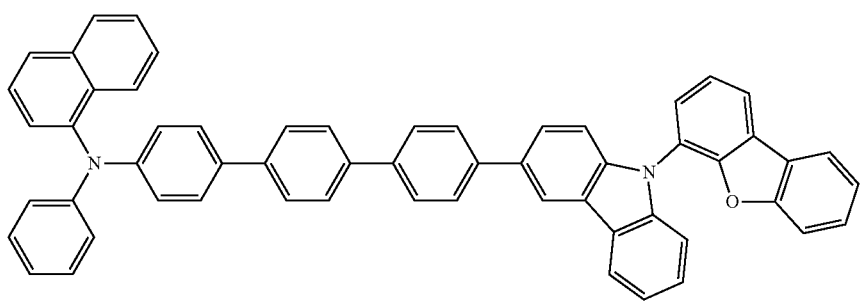
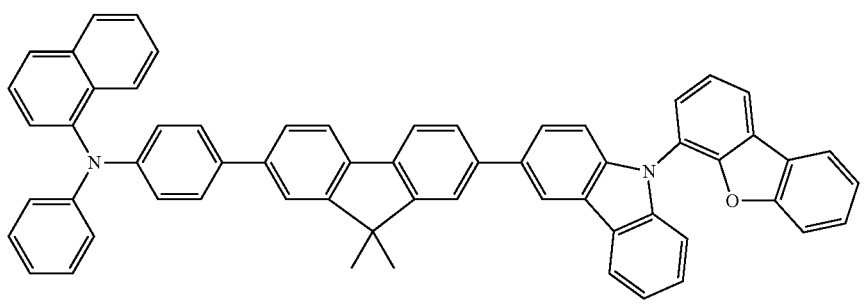

-continued
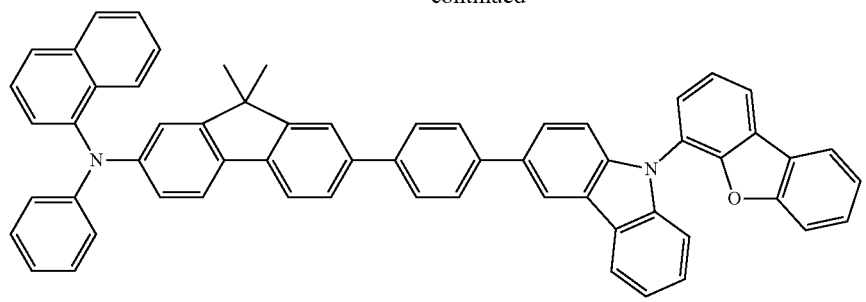
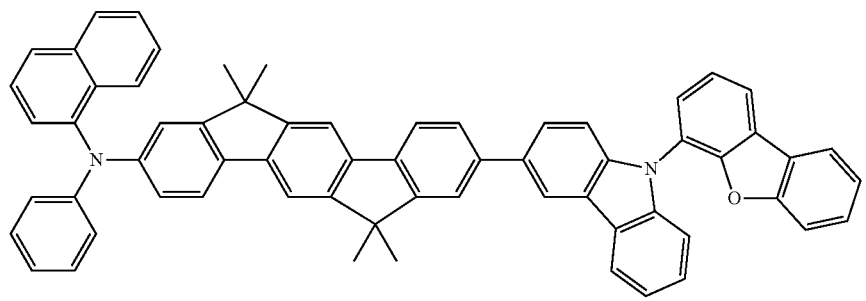
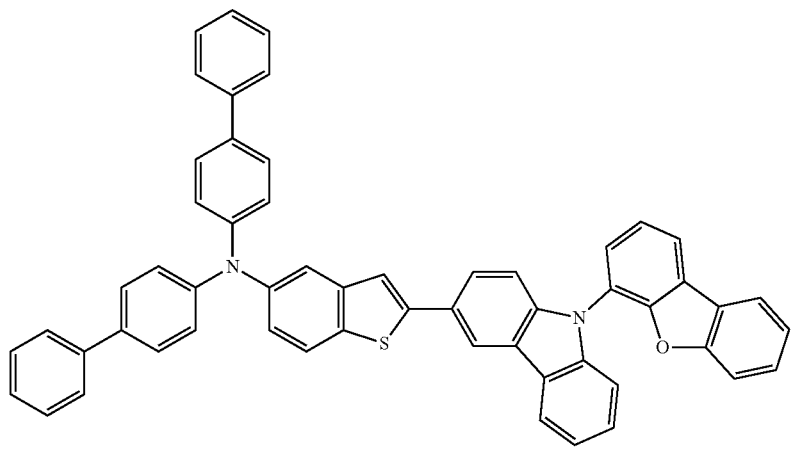
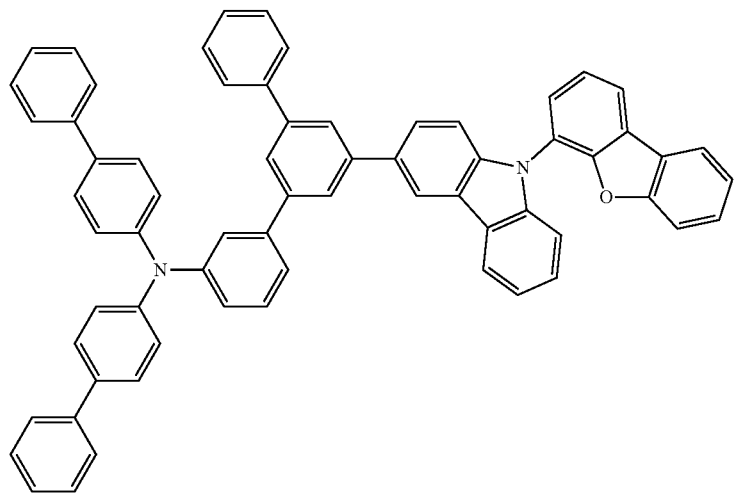

-continued
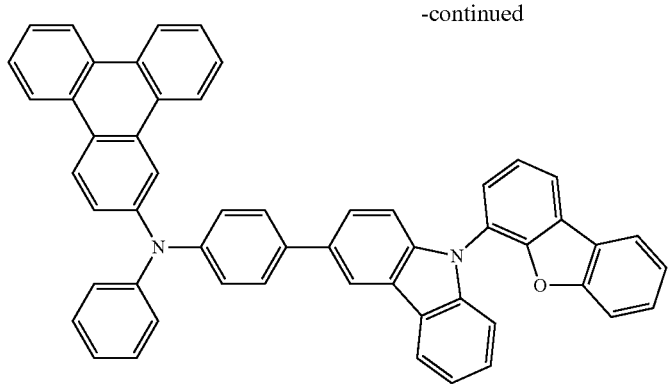
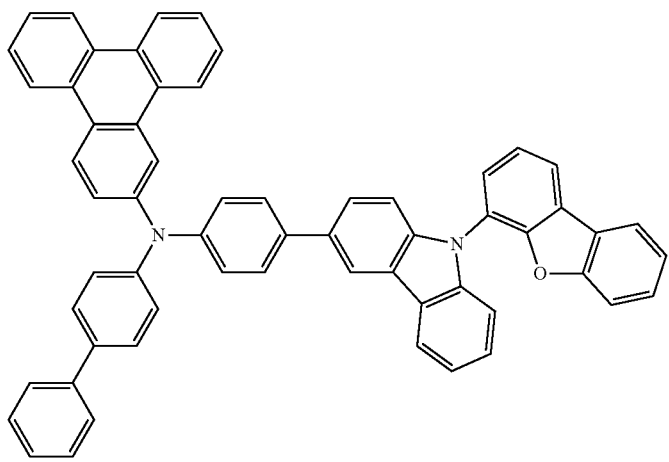
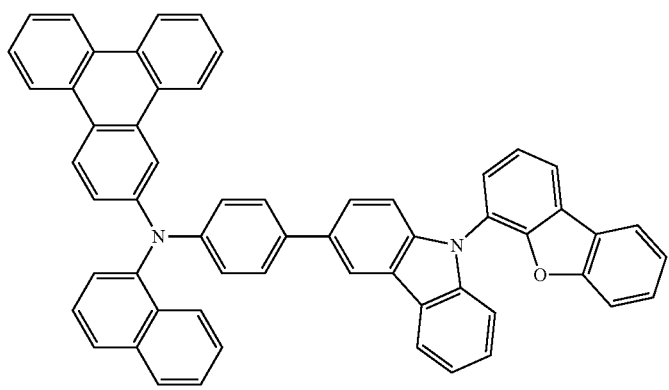
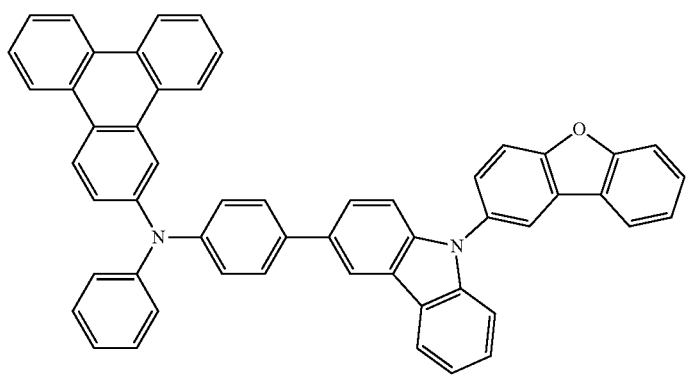

-continued
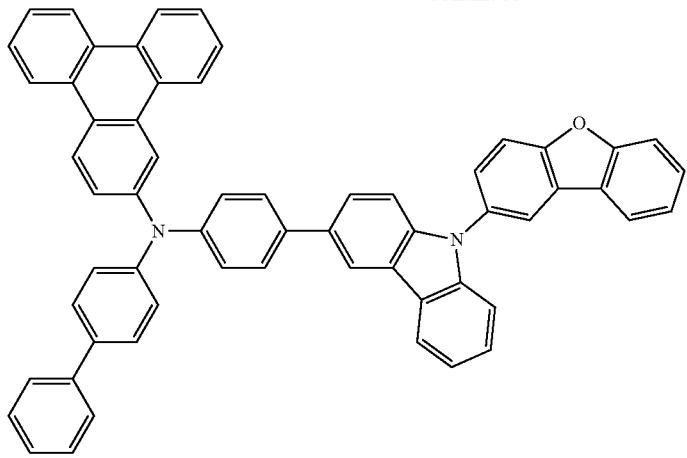
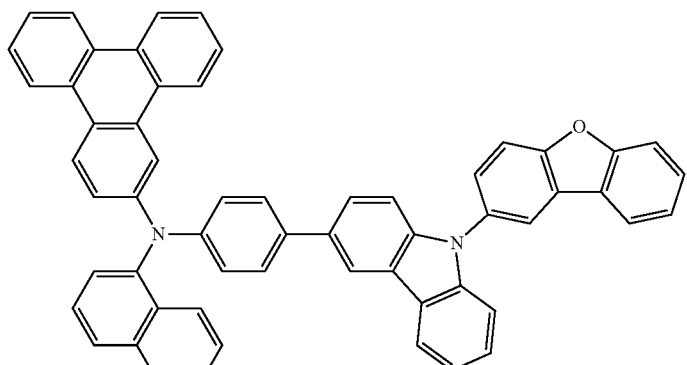
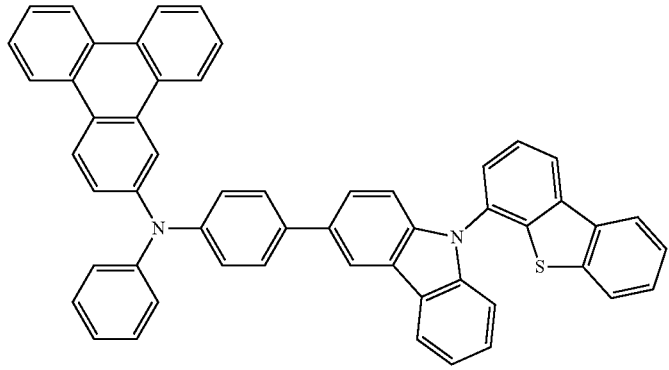
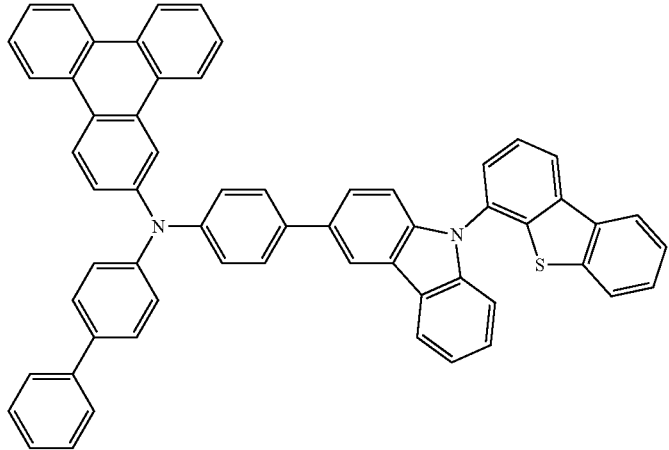

-continued
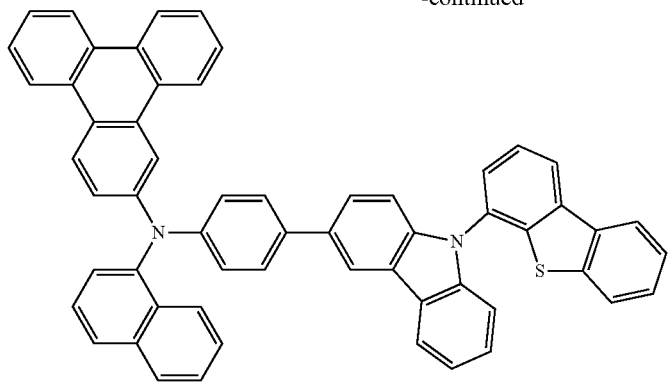
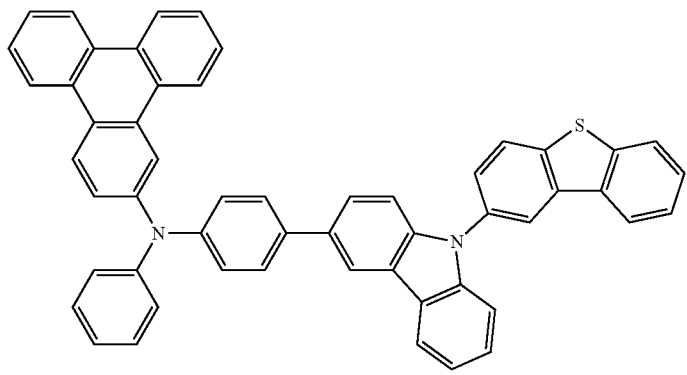
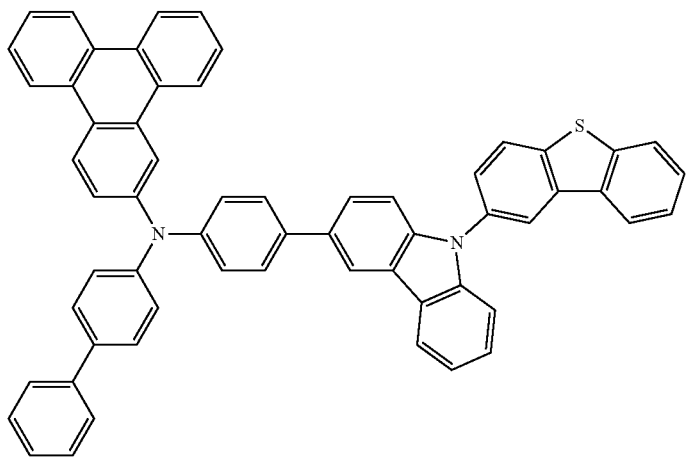
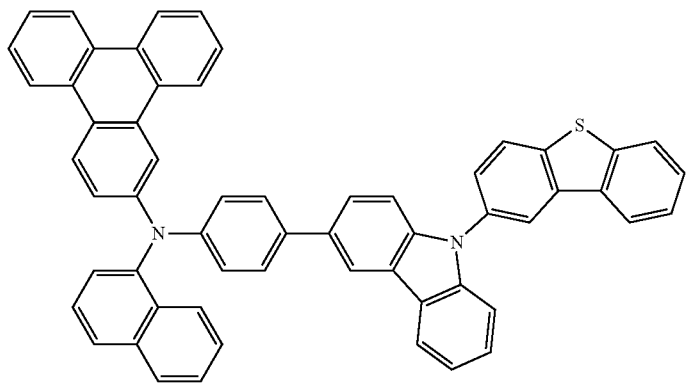

Organic EL Device

The organic EL device of the invention will be described below.

The organic EL device comprises one or more organic thin film layers between a cathode and an anode. The organic thin film layers comprise a light emitting layer and at least one layer of the organic thin film layers comprises the aromatic amine derivative of the invention. By using the aromatic amine derivative of the invention in at least one layer of the organic thin film layers, the emission efficiency and the lifetime of an organic EL device can be expected to be improved.

Examples of the organic thin film layer in which the aromatic amine derivative of the invention is usable include a hole transporting layer, a light emitting layer, a space layer, and a blocking layer, although not limited thereto. The aromatic amine derivative of the invention is preferably used in a hole transporting layer. The light emitting layer preferably comprises a fluorescent emitting material or a phosphorescent emitting material, more preferably comprises a phosphorescent emitting material.

The organic EL device of the invention may be any of a single color emitting device of fluorescent or phosphorescent type, a white-emitting device of fluorescent-phosphorescent hybrid type, an emitting device of a simple type having a single emission unit, and an emitting device of a tandem type having two or more emission units. The "emission unit" referred to herein is the smallest unit for emitting light by the recombination of injected holes and injected electrons, which comprises one or more organic layers wherein at least one layer is a light emitting layer.

Representative device structures of the simple-type organic EL device are shown below.

(1) Anode/Emission Unit/Cathode

The emission unit may be a laminate comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the emission unit are shown below.
(a) hole transporting layer/light emitting layer (/electron transporting layer);
(b) hole transporting layer/first phosphorescent light emitting layer/second phosphorescent light emitting layer (/electron transporting layer);
(c) hole transporting layer/phosphorescent light emitting layer/space layer/fluorescent light emitting layer (/electron transporting layer);
(d) hole transporting layer/first phosphorescent light emitting layer/second phosphorescent light emitting layer/space layer/fluorescent light emitting layer (/electron transporting layer);
(e) hole transporting layer/first phosphorescent light emitting layer/space layer/second phosphorescent light emitting layer/space layer/fluorescent light emitting layer (/electron transporting layer); and
(f) hole transporting layer/phosphorescent light emitting layer/space layer/first fluorescent light emitting layer/second fluorescent light emitting layer (/electron transporting layer)

The emission color of the phosphorescent light emitting layer and that of the fluorescent light emitting layer may be different. For example, the layered structure of the laminated light emitting layer (d) may be hole transporting layer/first phosphorescent light emitting layer (red emission)/second phosphorescent light emitting layer (green emission)/space layer/fluorescent light emitting layer (blue emission)/electron transporting layer.

An electron blocking layer may be disposed between the light emitting layer and the hole transporting layer or between the light emitting layer and the space layer, if necessary. Also, a hole blocking layer may be disposed between the light emitting layer and the electron transporting layer, if necessary. With such a electron blocking layer or a hole blocking layer, electrons and holes are confined in the light emitting layer to increase the degree of charge recombination in the light emitting layer, thereby improving the emission efficiency.

Representative device structure of the tandem-type organic EL device is shown below.
(2) anode/first emission unit/intermediate layer/second emission unit/cathode The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer may be formed by known materials so as to supply electrons to the first emission unit and holes to the second emission unit.

A schematic structure of an example of the organic EL device of the invention is shown in FIG. 1 wherein the organic EL device 1 is constructed by a substrate 2, an anode 3, a cathode 4, and an emission unit 10 disposed between the anode 3 and the cathode 4. The emission unit 10 includes a light emitting layer 5 which comprises at least one layer containing a phosphorescent host material a phosphorescent dopant material. A hole transporting layer 6, etc. may be disposed between the light emitting layer 5 and the anode 3, and an electron transporting layer 7, etc. may be disposed between the light emitting layer 5 and the cathode 4. An electron blocking layer may be disposed on the anode 3 side of the light emitting layer 5, and a hole blocking layer may be disposed on the cathode 4 side of the light emitting layer 5. With these blocking layers, electrons and holes are confined in the light emitting layer 5 to increase the degree of exciton generation in the light emitting layer 5.

In the present invention, the host is referred to as a fluorescent host when combinedly used with a fluorescent dopant and as a phosphorescent host when combinedly used with a phosphorescent dopant. Therefore, the fluorescent host and the phosphorescent host are not distinguished from each other merely by the difference in their molecular structures. Namely, the term "phosphorescent host" means a material for constituting a phosphorescent emitting layer containing a phosphorescent dopant and does not mean that the material is not usable as a material for constituting a fluorescent emitting layer. The same also applies to the fluorescent host.

Substrate

The organic EL device of the invention is formed on a light-transmissive substrate. The light-transmissive substrate serves as a support for the organic EL device and preferably a flat substrate having a transmittance of 50% or more to 400 to 700 nm visible light. Examples of the substrate include a glass plate and a polymer plate. The glass plate may include a plate made of soda-lime glass, barium-strontium-containing glass, lead glass, aluminosilicate glass, borosilicate glass, barium borosilicate glass, or quartz. The polymer plate may include a plate made of polycarbonate, acryl, polyethylene terephthalate, polyether sulfide, or polysulfone.

Anode

The anode of the organic EL device injects holes to the hole transporting layer or the light emitting layer, and an anode having a work function of 4.5 eV or more is effective. Examples of material for anode include indium tin oxide alloy (ITO), tin oxide (NESA), indium zinc oxide alloy, gold, silver, platinum, and cupper. The anode is formed by making the electrode material into a thin film by a method, such as a vapor deposition method or a sputtering method. When getting the light emitted from the light emitting layer through the anode, the transmittance of anode to visible light is preferably 10% or more. The sheet resistance of anode is preferably several hundreds Ω/□ or less. The film thickness of anode depends upon the kind of material and generally 10 nm to 1 μm, preferably 10 to 200 nm.

Cathode

The cathode injects electrons to the electron injecting layer, the electron transporting layer or the light emitting layer, and preferably formed from a material having a small work function. Examples of the material for cathode include, but not limited to, indium, aluminum, magnesium, magnesium-indium alloy, magnesium-aluminum alloy, aluminum-lithium alloy, aluminum-scandium-lithium alloy, and magnesium-silver alloy. Like the anode, the cathode is formed by making the material into a thin film by a method, such as the vapor deposition method and the sputtering method. The emitted light may be taken from the cathode, if appropriate.

Light Emitting Layer

The light emitting layer is an organic layer having a light emitting function and contains a host material and a dopant material when a doping system is employed. The major function of the host material is to promote the recombination of electrons and holes and confine excitons in the light emitting layer. The dopant material causes the excitons generated by recombination to emit light efficiently.

In case of a phosphorescent device, the major function of the host material is to confine the excitons generated on the dopant in the light emitting layer.

To control the carrier balance in the light emitting layer, a double host (host and co-host) system may be used for the light emitting layer, for example, by combinedly using an electron transporting host and a hole transporting host.

In addition, the light emitting layer may be made into a double dopant layer, in which two or more kinds of dopant materials having high quantum yield are combinedly used and each dopant material emits light with its own color. For example, to obtain a yellow emission, a light emitting layer formed by co-depositing a host, a red-emitting dopant and a green-emitting dopant is used.

In a laminate of two or more light emitting layers, electrons and holes are accumulated in the interface between the light emitting layers, and therefore, the recombination region is localized in the interface between the light emitting layers, to improve the quantum efficiency.

The hole injection ability and the electron injection ability, each into the light emitting layer, may be different. In addition, the hole transporting ability and the electron transporting ability each being expressed by mobility in the light emitting layer may be different.

The light emitting layer is formed, for example, by a known method, such as a vapor deposition method, a spin coating method, and LB method. Alternatively, the light emitting layer may be formed by making a solution of a binder, such as resin, and the material for the light emitting layer in a solvent into a thin film by a method such as spin coating.

The light emitting layer is preferably a molecular deposit film. The molecular deposit film is a thin film formed by depositing a vaporized material or a film formed by solidifying a material in the state of solution or liquid. The molecular deposit film can be distinguished from a thin film formed by LB method (molecular build-up film) by the differences in the assembly structures and higher order structures and the functional difference due to the structural differences.

The phosphorescent dopant (phosphorescent emitting material) is a compound which emits light by releasing the energy of excited triplet state and preferably a organometallic complex comprising at least one metal selected from Ir, Pt, Os, Au, Cu, Re, and Ru and a ligand, although not particularly limited thereto as long as emitting light by releasing the energy of excited triplet state. A ligand having an ortho metal bond is preferred. In view of obtaining a high phosphorescent quantum yield and further improving the external quantum efficiency of electroluminescence device, a metal complex comprising a metal selected from Ir, Os, and Pt is preferred, with iridium complex, osmium complex, and platinum being more preferred, iridium complex and platinum complex being still more preferred, and an ortho metallated iridium complex being particularly preferred.

The content of the phosphorescent dopant in the light emitting layer is not particularly limited and selected according to the use of the device, and preferably 0.1 to 70% by mass, and more preferably 1 to 30% by mass. If being 0.1% by mass or more, the amount of light emission is sufficient. If being 70% by mass or less, the concentration quenching can be avoided.

Preferred examples of the organometallic complex are shown below.

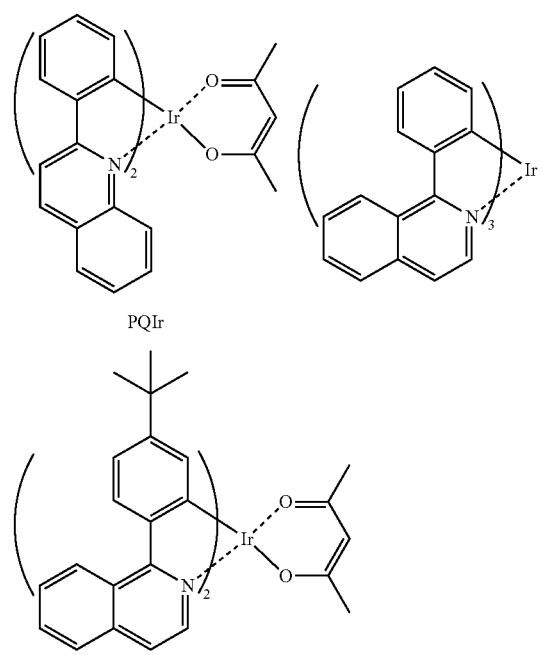

PQIr

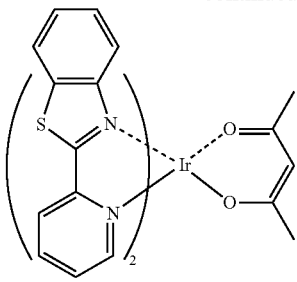
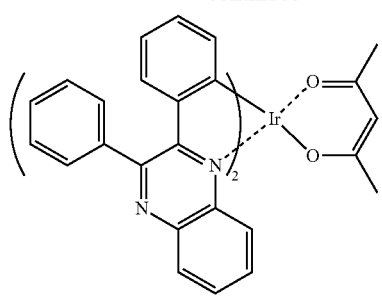
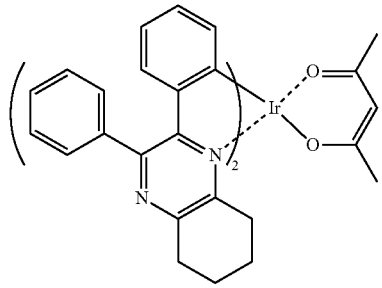
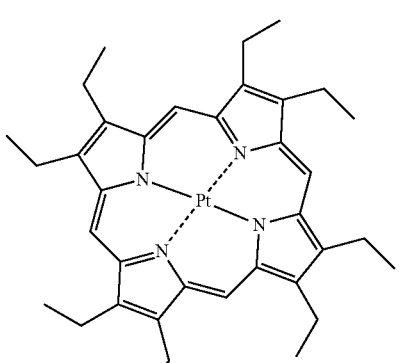
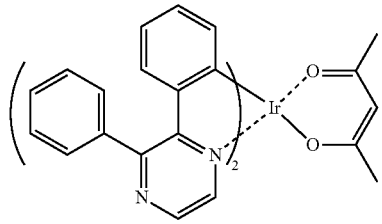
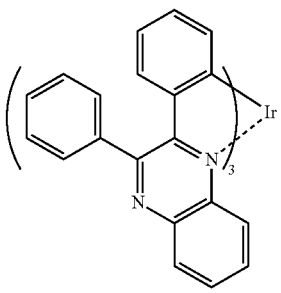
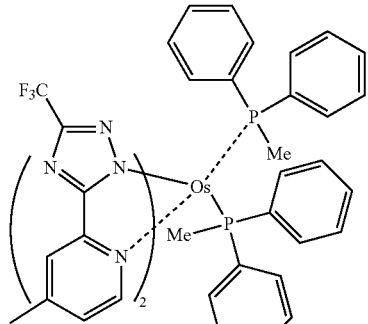
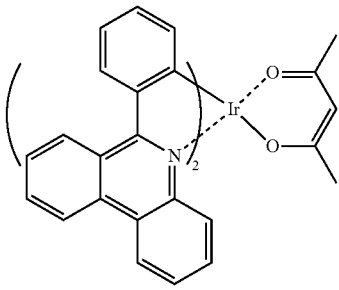
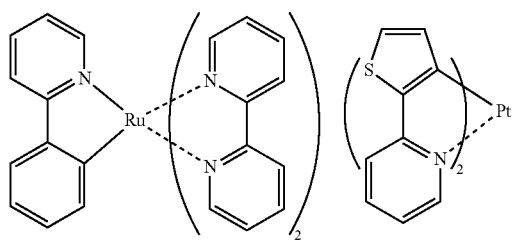
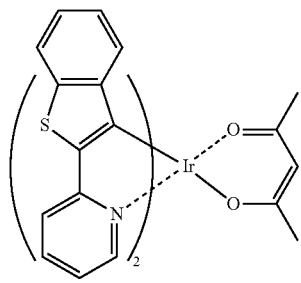
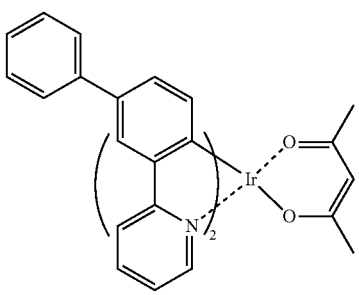

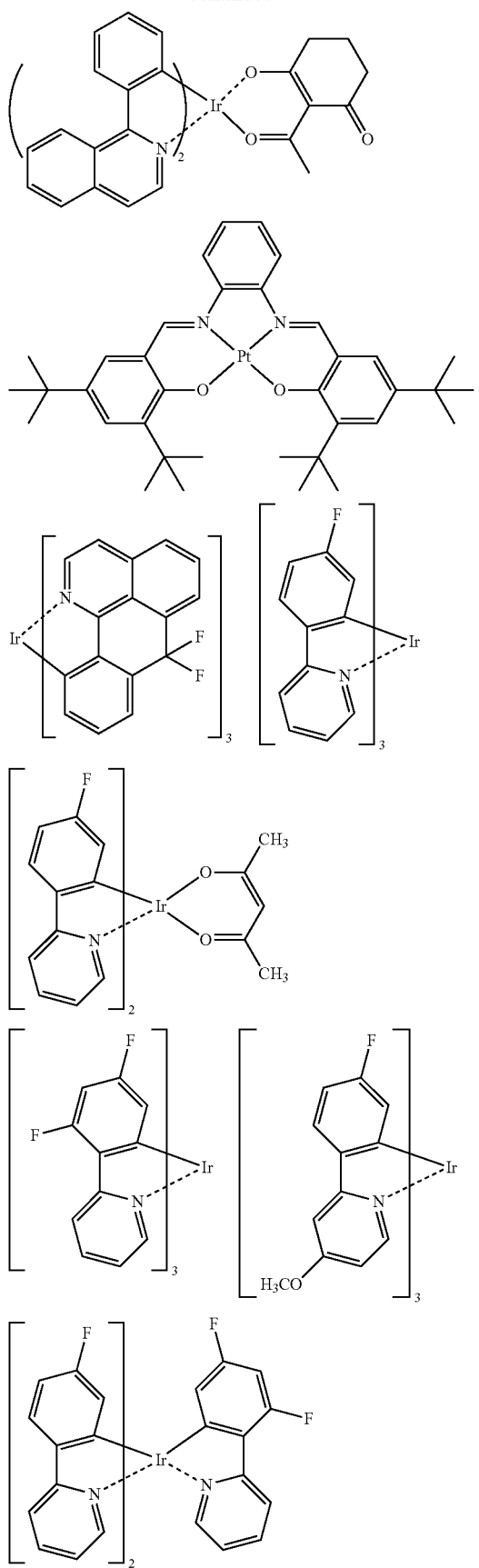
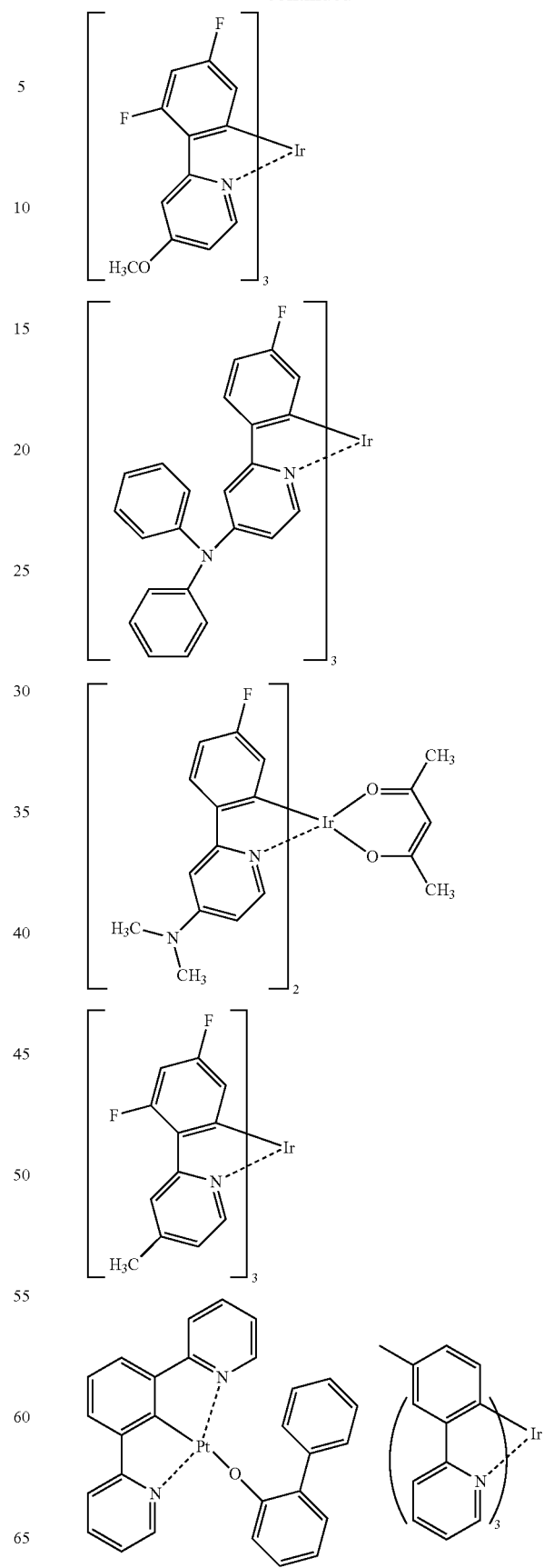

-continued
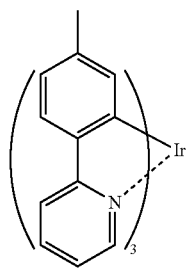
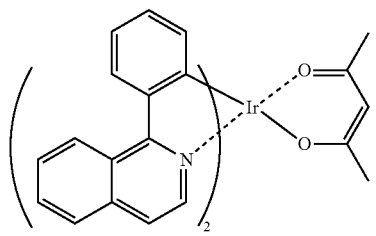
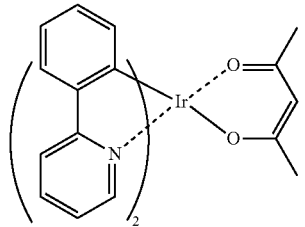
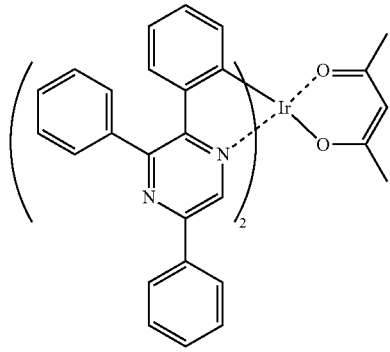
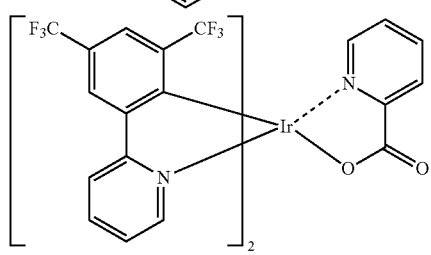
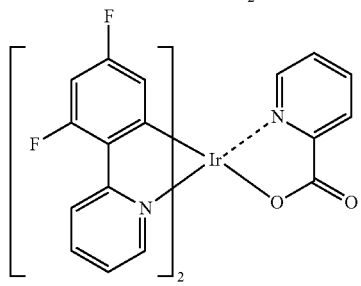
-continued
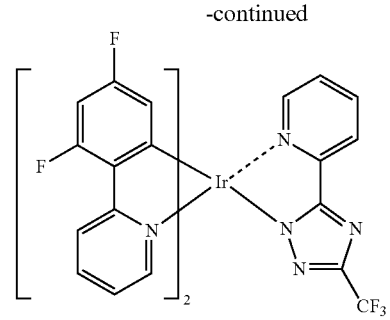
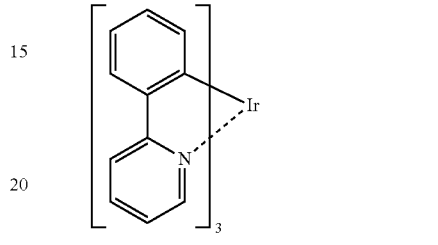
Ir(ppy)₃
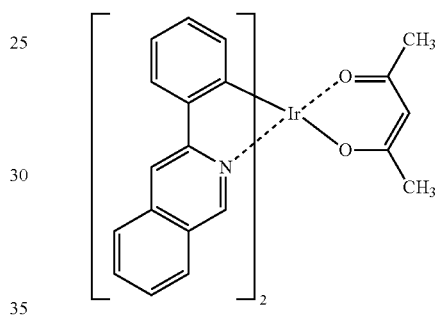
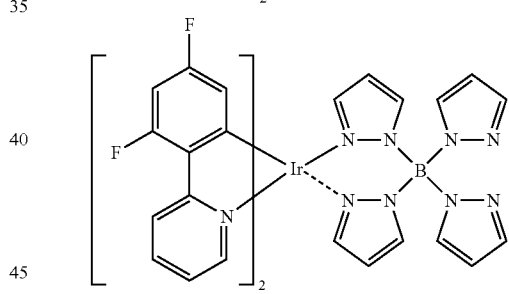
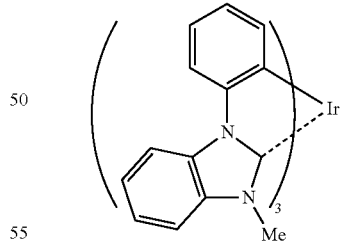
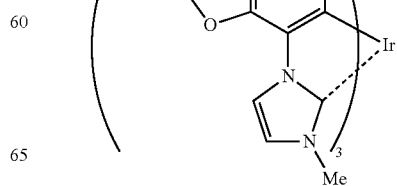

123
-continued
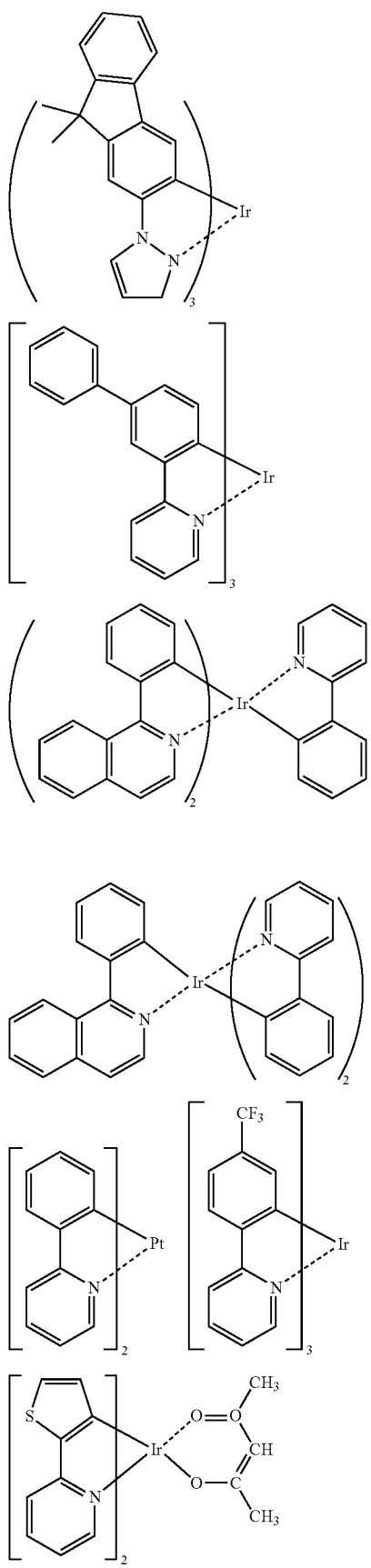
124
-continued
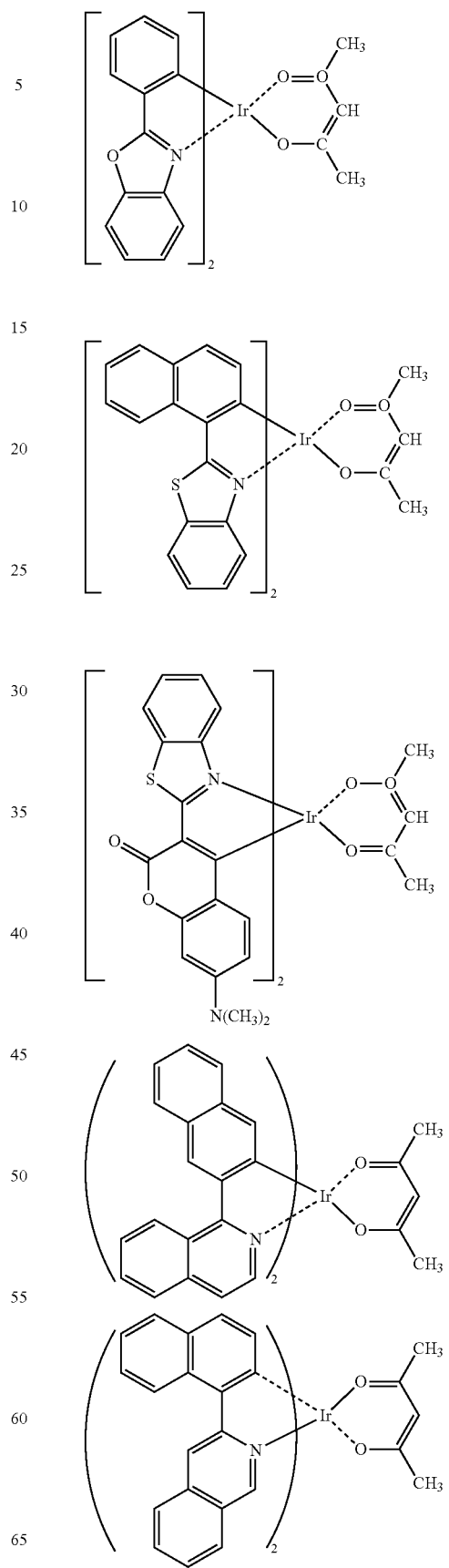

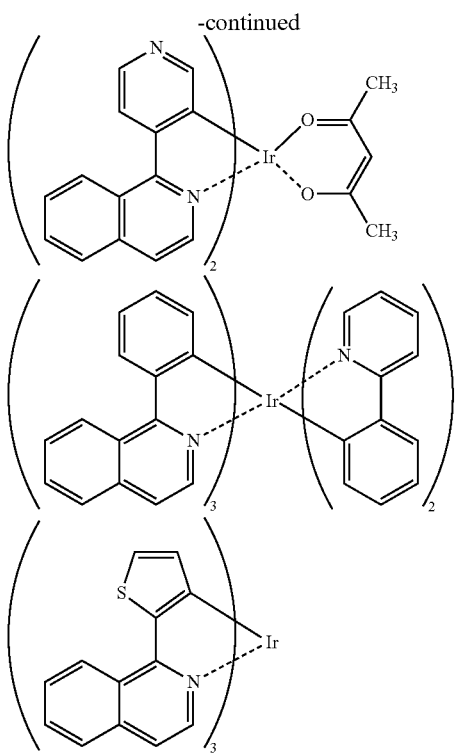

The phosphorescent host is a compound which confines the triplet energy of the phosphorescent dopant efficiently in the light emitting layer to cause the phosphorescent dopant to emit light efficiently. The aromatic amine derivative of the invention is useful as the phosphorescent host. A compound other than the aromatic amine derivative of the invention can be used as the phosphorescent host according to the use of the device.

The aromatic amine derivative of the invention and a compound other than it may be combinedly used in the same light emitting layer as the phosphorescent host material. If two or more light emitting layers are formed, the aromatic amine derivative of the invention can be used in one light emitting layer as the phosphorescent host material and a compound other than the aromatic amine derivative of the invention can be used in another light emitting layer as the phosphorescent host material. The aromatic amine derivative of the invention may be used in an organic layer other than the light emitting layer. In this case, a compound other than the aromatic amine derivative of the invention may be used as the phosphorescent host of the light emitting layer.

Examples of the compounds other than the aromatic amine derivative of the invention, which are suitable as the phosphorescent host, include a carbazole derivative, a triazole derivative, a oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic methylidene compound, a porphyrin compound, an anthraquinodimethane derivative, an anthrone derivative, a diphenylquinone derivative, a thiopyran dioxide derivative, a carbodiimide derivative, a fluorenylidenemethane derivative, a distyrylpyrazine derivative, a tetracarboxylic anhydride of fused ring such as naphthalene and perylene, a phthalocyanine derivative, a metal complex of 8-quinolinol derivative, metal phthalocyanine, metal complexes having a ligand such as benzoxazole and benzothiazole, an electroconductive oligomer, such as a polysilane compound, a poly(N-vinylcarbazole) derivative, an aniline copolymer, thiophene oligomer, and a polythiophene, and a polymer such as a polythiophene derivative, a polyphenylene derivative, a polyphenylenevinylene derivative, and a polyfluorene derivative. These phosphorescent hosts may be used alone or in combination of two or more. Specific examples thereof are shown below.

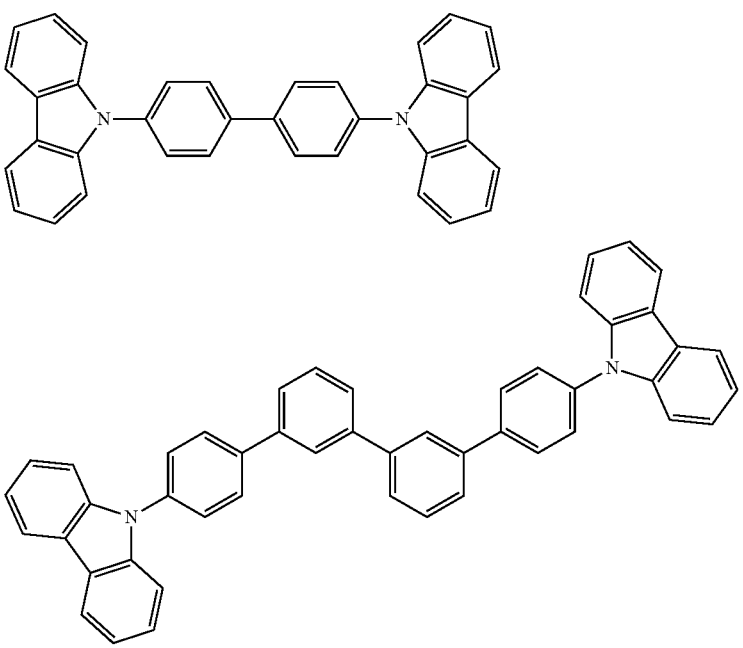

-continued
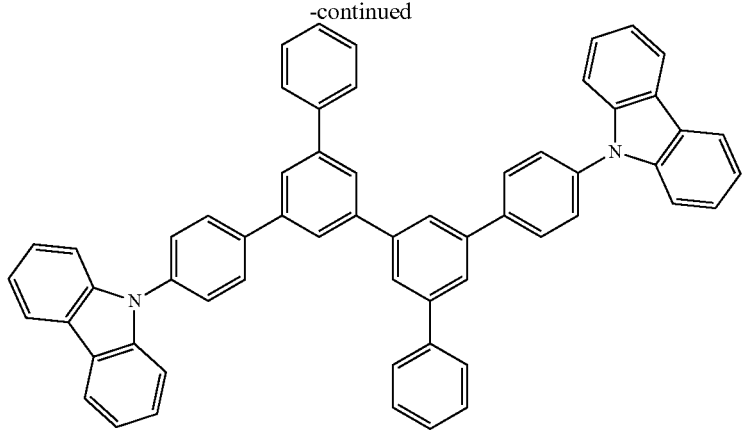
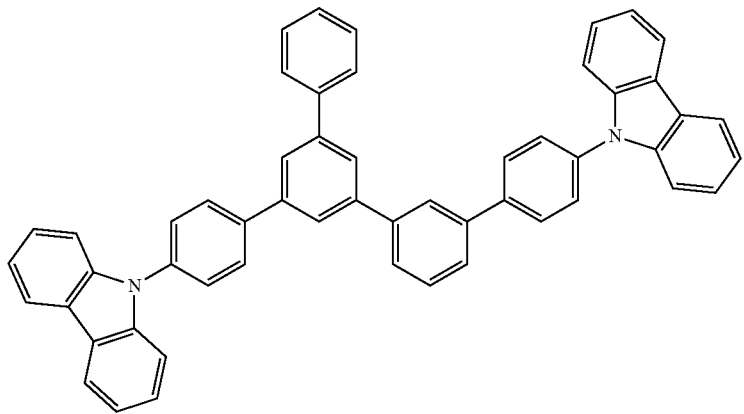
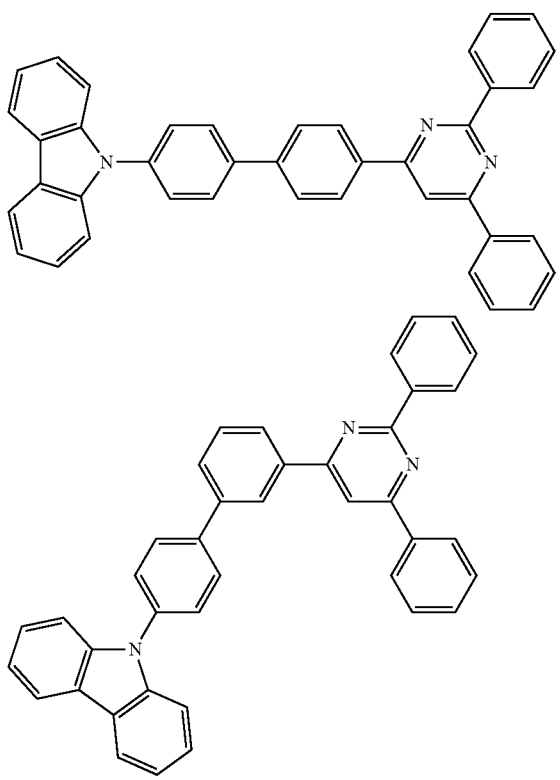

The thickness of the light emitting layer is preferably 5 to 50 nm, more preferably 7 to 50 nm, and still more preferably 10 to 50 nm. If being 5 nm or more, the light emitting layer is easily formed. If being 50 nm or less, the increase in driving voltage is avoided.

Electron-Donating Dopant

It is preferred for the organic EL device of the invention to contain an electron-donating dopant in the interfacial region between the cathode and the light emitting unit. With such a construction, the organic EL device has an improved luminance and an elongated lifetime. The electron-donating dopant is a metal having a work function of 3.8 eV or less or a compound containing such metal. Examples thereof include at least one compound selected from alkali metal, alkali metal complex, alkali metal compound, alkaline earth metal, alkaline earth metal complex, alkaline earth metal compound, rare earth metal, rare earth metal complex, and rare earth metal compound.

Examples of the alkali metal include Na (work function: 2.36 eV), K (work function: 2.28 eV), Rb (work function: 2.16 eV), and Cs (work function: 1.95 eV), with those having a work function of 2.9 eV or less being particularly preferred. Of the above, preferred are K, Rb, and Cs, more preferred are Rb and Cs, and most preferred is Cs. Examples of the alkaline earth metal include Ca (work function: 2.9 eV), Sr (work function: 2.0 to 2.5 eV), and Ba (work function: 2.52 eV), with those having a work function of 2.9 eV or less being particularly preferred. Examples of the rare earth metal include Sc, Y, Ce, Tb, and Yb, with those having a work function of 2.9 eV or less being particularly preferred.

Examples of the alkali metal compound include alkali oxide, such as $Li_2O$, $Cs_2O$, $K_2O$, and alkali halide, such as LiF, NaF, CsF, and KF, with LiF, $Li_2O$, and NaF being preferred. Examples of the alkaline earth metal compound include BaO, SrO, CaO, and mixture thereof, such as $Ba_xSr_{1-x}O$ (0<x<1) and $Ba_xCA_{1-x}O$ (0<x<1), with BaO, SrO, and CaO being preferred. Examples of the rare earth metal compound include $YbF_3$, $ScF_3$, $ScO_3$, $Y_2O_3$, $Ce_2O_3$, $GdF_3$, and $TbF_3$, with $YbF_3$, $ScF_3$, and $TbF_3$ being preferred.

Examples of the alkali metal complex, alkaline earth metal complex, and rare earth metal are not particularly limited as long as containing at least one metal ion selected from alkali metal ions, alkaline earth metal ions, and rare earth metal ions, respectively. The ligand is preferably, but not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bipyridyl, phenanthroline, phthalocyanine, porphyrin, cyclopentadiene, β-diketones, azomethines, and derivative thereof.

The electron-donating dopant is added to the interfacial region preferably into a form of layer or island. The electron-donating dopant is added preferably by co-depositing the electron-donating dopant with the organic compound (light emitting material, electron injecting material, etc.) for forming the interfacial region by a resistance heating deposition method, thereby dispersing the electron-donating dopant into the organic material. The disperse concentration expressed by the molar ratio of the organic material and the electron-donating dopant is 100:1 to 1:100 and preferably 5:1 to 1:5.

When the electron-donating dopant is formed into a form of layer, a light emitting material or an electron injecting material is made into a layer which serves as an organic layer in the interface, and then, the electron-donating dopant alone is deposited by a resistance heating deposition method into a layer having a thickness preferably 0.1 to 15 nm. When the electron-donating dopant is formed into a form of island, a light emitting material or an electron injecting material is made into a form of island which serves as an organic layer in the interface, and then, the electron-donating dopant alone is deposited by a resistance heating deposition method into a form of island having a thickness preferably 0.05 to 1 nm.

The molar ratio of the main component and the electron-donating dopant in the organic electroluminescence device of the invention is preferably 5:1 to 1:5 and more preferably 2:1 to 1:2.

Electron Transporting Layer

The electron transporting layer is an organic layer disposed between the light emitting layer and the cathode and transports electrons from the cathode to the light emitting layer. If two or more electron transporting layers are provided, the organic layer closer to the cathode may be called an electron injecting layer in some cases. The electron injecting layer injects electrons from the cathode to the organic layer unit efficiently.

An aromatic heterocyclic compound having one or more heteroatoms in its molecule is preferably used as the electron transporting material for the electron transporting layer, with a nitrogen-containing ring derivative being particularly preferred. The nitrogen-containing ring derivative is preferably an aromatic ring compound having a nitrogen-containing 6- or 5-membered ring or a condensed aromatic ring compound having a nitrogen-containing 6- or 5-membered ring.

The nitrogen-containing ring derivative is preferably, for example, a chelate metal complex having a nitrogen-containing ring represented by formula (A).

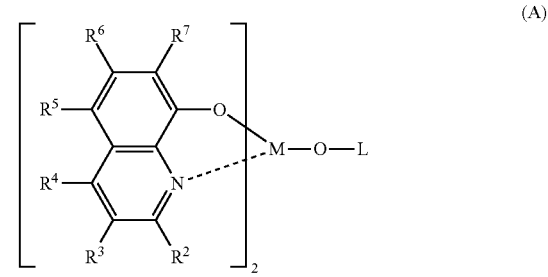

$R^2$ to $R^7$ of formula (A) each independently represent a hydrogen atom, a deuterium atom, a halogen atom, a hydroxyl group, a substituted or unsubstituted amino group, a hydrocarbon group having 1 to 40 carbon atoms, an alkoxy group having 1 to 40 carbon atoms, an aryloxy group having 6 to 50 ring carbon atoms, an alkoxycarbonyl group, or a heterocyclic group having 5 to 50 ring carbon atoms, each being optionally substituted.

The halogen atom may include fluorine, chlorine, bromine, and iodine.

The substituted amino group may include an alkylamino group, an arylamino group, and an aralkylamino group.

The alkylamino group and the aralkylamino group are represented by $-NQ^1Q^2$, wherein $Q^1$ and $Q^2$ each independently represent an alkyl group having 1 to 20 carbon atoms or an aralkyl group having 7 to 30 carbon atoms. One of $Q^1$ and $Q^2$ may be a hydrogen atom or a deuterium atom.

The arylamino group is represented by $-NAr^1Ar^2$, wherein $Ar^1$ and $Ar^2$ each independently represent a non-condensed aromatic hydrocarbon group or a condensed aromatic hydrocarbon group each having 6 to 50 ring carbon atoms. One of Ar$^1$ and Ar$^2$ may be a hydrogen atom or a deuterium atom.

The hydrocarbon group having 1 to 40 carbon atoms may include an alkyl group, an alkenyl group, a cycloalkyl group, an aryl group, and an aralkyl group.

The alkoxycarbonyl group is represented by —COMP, wherein Y' is an alkyl group having 1 to 20 carbon atoms.

M is aluminum (Al), gallium (Ga), or indium (In), with In being preferred.

L is a group represented by formula (A') or (A"):

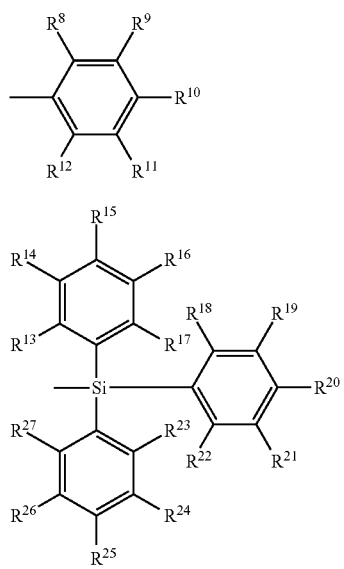

R$^8$ to R$^{12}$ in formula (A') each independently represent a hydrogen atom, a deuterium atom, or a substituted or unsubstituted hydrocarbon group having 1 to 40 carbon atoms. The adjacent two groups may form a ring structure. R$^{13}$ to R$^{27}$ in formula (A") each independently represent a hydrogen atom, a deuterium atom, or a substituted or unsubstituted hydrocarbon group having 1 to 40 carbon atoms. The adjacent two groups may form a ring structure.

Examples of the hydrocarbon group having 1 to 40 carbon atoms for R$^8$ to R$^{12}$ and R$^{13}$ to R$^{27}$ in formulae (A') and (A") are the same as those described above with respect to R$^2$ to R$^7$ of formula (A). Examples of the divalent group formed by the adjacent two groups of R$^8$ to R$^{12}$ and R$^{13}$ to R$^{27}$ which completes the ring structure include tetramethylene group, pentamethylene group, hexamethylene group, diphenyl-methane-2,2'-diyl group, diphenylethane-3,3'-diyl group, and diphenylpropane-4,4'-diyl group.

The electron transporting compound for the electron transporting layer is preferably a metal complex including 8-hydroxyquinoline or its derivative, an oxadiazole derivative, and a nitrogen-containing heterocyclic derivative. Examples of the metal complex including 8-hydroxyquinoline or its derivative include a metal chelate oxinoid including a chelated oxine (generally, 8-quinolinol or 8-hydroxyquinoline), for example, tris(8-quinolinol)aluminum. Examples of the oxadiazole derivative are shown below.

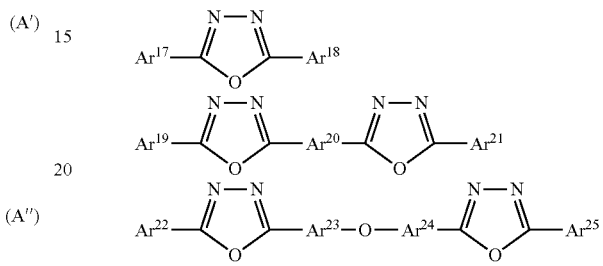

In the above formulae, each of Ar$^{17}$, Ar$^{18}$, Ar$^{19}$, Ar$^{21}$, Ar$^{22}$, and Ar$^{25}$ is a substituted or unsubstituted non-fused aromatic hydrocarbon group or a substituted or unsubstituted fused aromatic hydrocarbon group each having 6 to 50 ring carbon atoms, and Ar$^{17}$ and Ar$^{18}$, Ar$^{19}$ and Ar$^{21}$, and Ar$^{22}$ and Ar$^{25}$ may be the same or different. Examples of the non-fused aromatic hydrocarbon group and the fused aromatic hydrocarbon group include phenyl group, naphthyl group, biphenyl group, anthranyl group, perylenyl group, and pyrenyl group. The optional substituent may be an alkyl group having 1 to 10 carbon atoms, an alkoxyl group having 1 to 10 carbon atoms or a cyano group.

Each of Ar$^{20}$, Ar$^{23}$, and Ar$^{24}$ is a substituted or unsubstituted bivalent non-fused aromatic hydrocarbon group or a substituted or unsubstituted bivalent fused aromatic hydrocarbon group each having 6 to 50 ring carbon atoms, and Ar$^{23}$ and Ar$^{24}$ may be the same or different. Examples of the bivalent non-fused aromatic hydrocarbon group or the bivalent fused aromatic hydrocarbon group include phenylene group, naphthylene group, biphenylene group, anthranylene group, perylenylene group, and pyrenylene group. The optional substituent may be an alkyl group having 1 to 10 carbon atoms, an alkoxyl group having 1 to 10 carbon atoms or a cyano group.

Electron transporting compounds which have a good thin film-forming property are preferably used. Examples of the electron transporting compound are shown below.

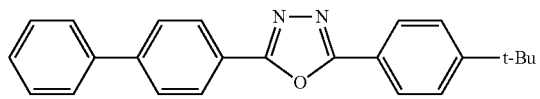

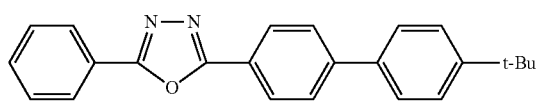

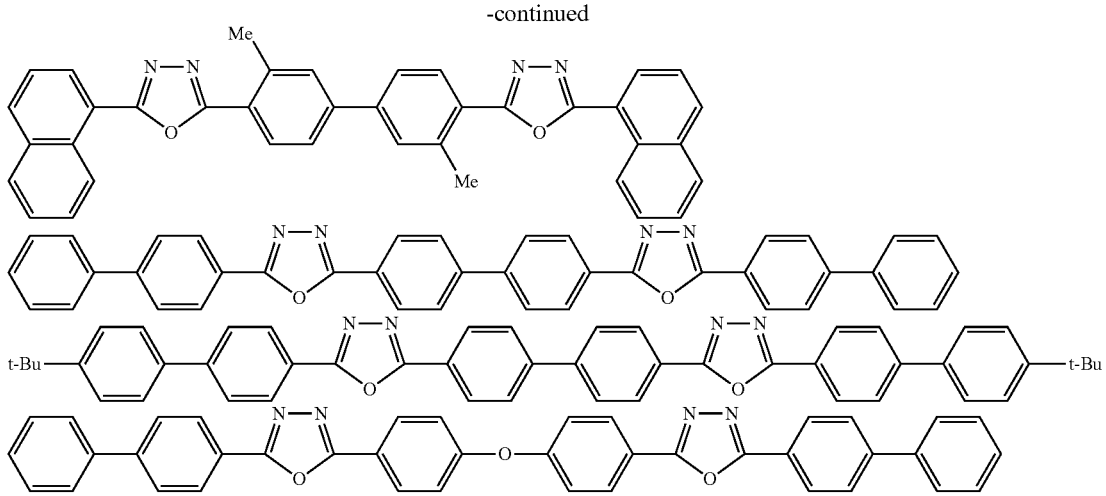

Examples of the nitrogen-containing heterocyclic derivative for use as the electron transporting compound include a nitrogen-containing heterocyclic derivative having the following formulae but exclusive of metal complex, for example, a compound having a 5- or 6-membered ring which has the skeleton represented by formula (B) or having the structure represented by formula (C).

(B)

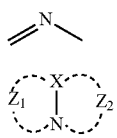

(C)

In formula (C), X is a carbon atom or a nitrogen atom. $Z_1$ and $Z_2$ each independently represent a group of atoms for completing the nitrogen-containing heteroring.

The nitrogen-containing heterocyclic derivative is more preferably an organic compound which has a nitrogen-containing aromatic polycyclic ring comprising a 5-membered ring or a 6-membered ring. If two or more nitrogen atoms are included, the nitrogen-containing aromatic polycyclic compound preferably has a skeleton of a combination of (B) and (C) or a combination of (B) and (D).

(D)

The nitrogen-containing group of the nitrogen-containing aromatic polycyclic compound is selected, for example, from the nitrogen-containing heterocyclic groups shown below.

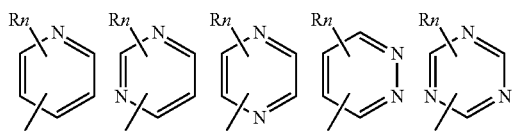

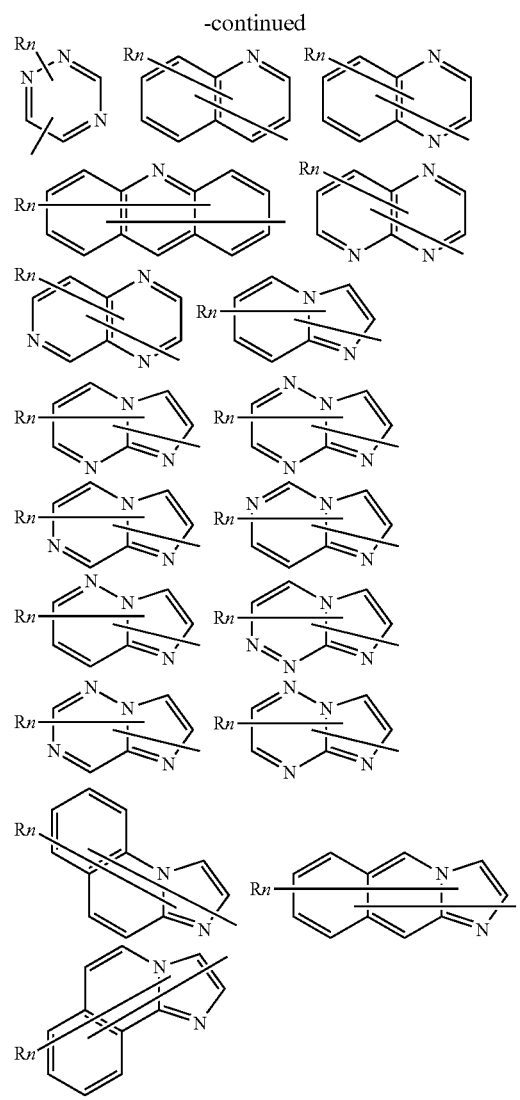

In the above formulae, R is a non-fused aromatic hydrocarbon group or a fused aromatic hydrocarbon group each having 6 to 40 ring carbon atoms, a non-fused aromatic heterocyclic group or a fused aromatic heterocyclic group each having 3 to 40 ring carbon atoms, an alkyl group having 1 to 20 carbon atoms, or an alkoxy group having 1 to 20 carbon atoms; and n is an integer of 0 to 5. If n is an integer of 2 or more, R groups may be the same or different.

More preferred is a nitrogen-containing heterocyclic derivative represented by the following formula:

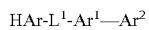

wherein HAr is a substitute or unsubstituted nitrogen-containing heterocyclic group having 3 to 40 ring carbon atoms; L¹ is a single bond, a substituted or unsubstituted, non-fused or fused aromatic hydrocarbon group having 6 to 40 ring carbon atoms, or a substituted or unsubstituted, non-fused or fused aromatic heterocyclic group having 3 to 40 ring carbon atoms; Ar¹ is a substitute or unsubstituted divalent aromatic hydrocarbon group having 6 to 40 ring carbon atoms; and Ar² is a substitute or unsubstituted, non-fused or fused aromatic hydrocarbon group having 6 to 40 ring carbon atoms or a substituted or unsubstituted, non-fused or fused aromatic heterocyclic group having 3 to 40 ring carbon atoms.

HAr is selected, for example, from the following groups:

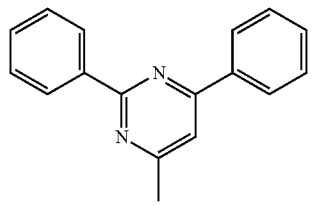

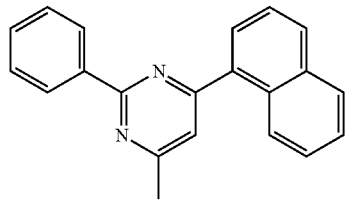

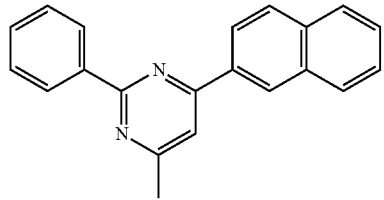

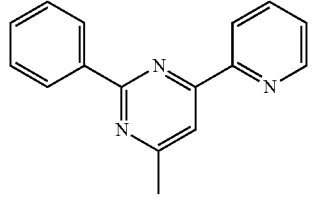

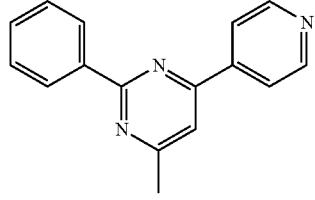

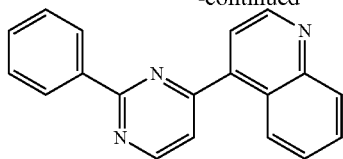

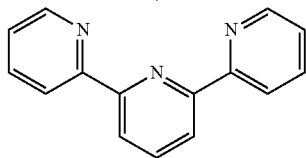

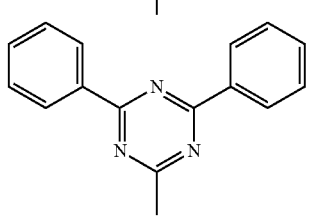

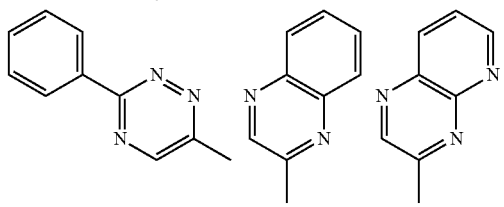

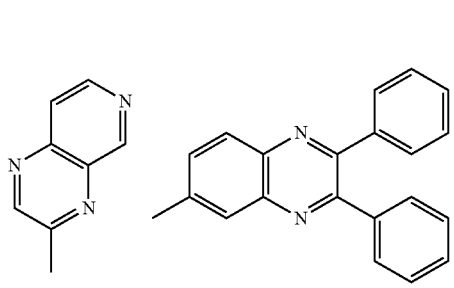

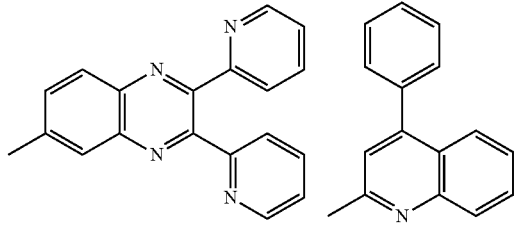

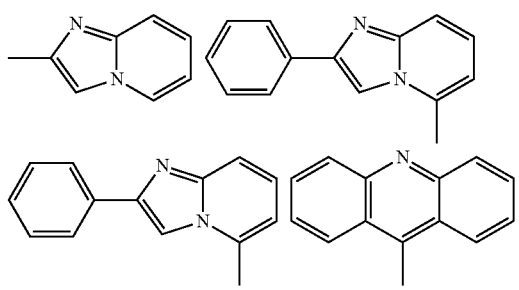

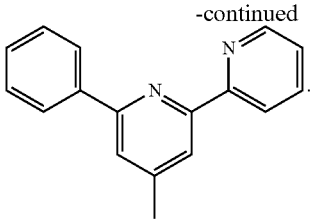

$L^1$ is selected, for example, from the following groups:

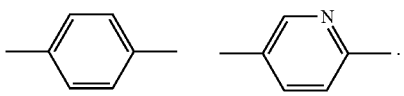

$Ar^1$ is selected, for example, from the following anthracenediyl groups:

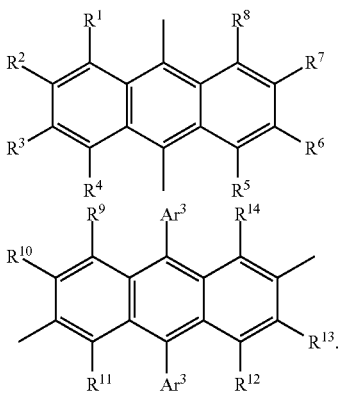

In the above formulae, $R^1$ to $R^{14}$ are each independently a hydrogen atom, a deuterium atom, a halogen atom, an alkyl group having 1 to 20 carbon atoms, an alkoxy group having 1 to 20 carbon atoms, an aryloxy group having 6 to 40 ring carbon atoms, a substituted or unsubstituted, non-fused or fused aromatic hydrocarbon group having 6 to 40 ring carbon atoms, or a substituted or unsubstituted, non-fused or fused aromatic heterocyclic group having 3 to 40 ring carbon atoms; and Ara is a substituted or unsubstituted, non-fused or fused aromatic hydrocarbon group having 6 to 40 ring carbon atoms, or a substituted or unsubstituted, non-fused or fused aromatic heterocyclic group having 3 to 40 ring carbon atoms. $R^1$ to $R^8$ may be all selected from a hydrogen atom and a deuterium atom.

$Ar^2$ is selected, for example, from the following groups:

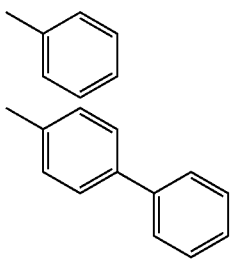

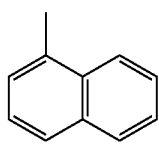

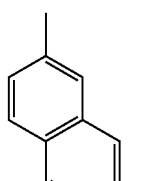

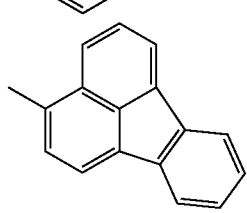

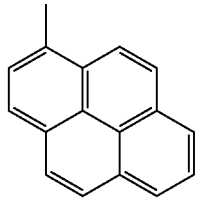

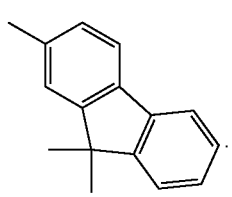

In addition, the following compound is preferably used as the nitrogen-containing aromatic polycyclic compound for use as the electron transporting compound.

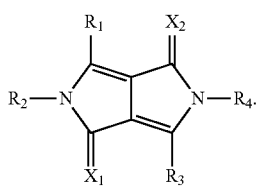

In the above formula, $R_1$ to $R_4$ each independently represent a hydrogen atom, a deuterium atom, a substituted or unsubstituted aliphatic group having 1 to 20 carbon atoms, a substituted or unsubstituted alicyclic group having 3 to 20 ring carbon atoms, a substituted or unsubstituted aromatic group having 6 to 50 ring carbon atoms, or a substituted or unsubstituted heterocyclic group having 3 to 50 ring carbon atoms; and $X_1$ and $X_2$ each independently represent an oxygen atom, a sulfur atom, or dicyanomethylene group.

Further, the following compound is also suitable as the electron transporting compound.

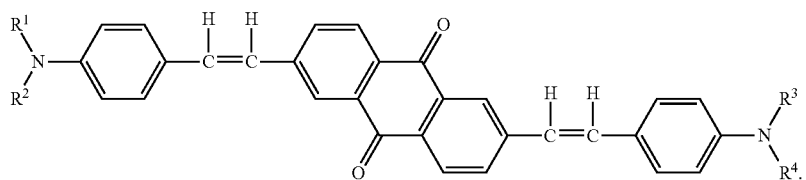

In the above formula, $R^1$, $R^2$, $R^3$, and $R^4$ may be the same or different and each represents an aromatic hydrocarbon group represented by the following formula:

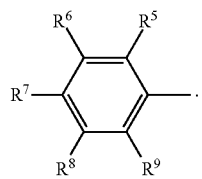

In the above formula, $R^5$, $R^6$, $R^7$, $R^8$, and $R^9$ may be the same or different and each represents a hydrogen atom, a deuterium atom, a saturated or unsaturated alkoxyl group having 1 to 20 carbon atoms, a saturated or unsaturated alkyl group having 1 to 20 carbon atoms, an amino group, or an alkylamino group having 1 to 20 carbon atoms. At least one of $R^5$, $R^6$, $R^7$, $R^8$, and $R^9$ is a group other than hydrogen atom and deuterium atom.

Further, a polymer having the nitrogen-containing heterocyclic group or the nitrogen-containing heterocyclic derivative is also usable as the electron transporting compound.

It is particularly preferred for the electron transporting layer of the organic EL of the invention to contain at least one of the nitrogen-containing heterocyclic derivatives represented by formulae (60) to (62):

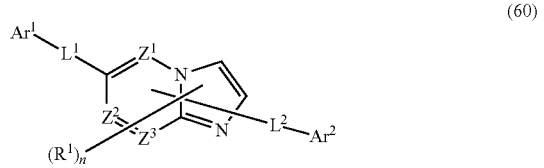

(60)

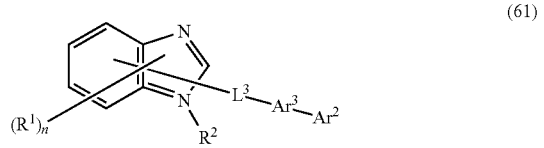

(61)

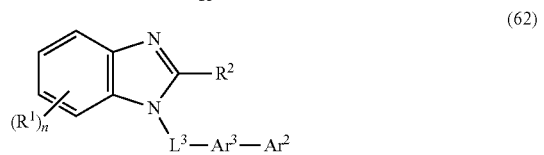

(62)

In formulae (60) to (62), $Z^1$, $Z^2$, and $Z^3$ each independently represent a nitrogen atom or a carbon atom.

$R^1$ and $R^2$ each independently represent a substituted or unsubstituted aryl group having 6 to 50 ring carbon atoms, a substituted or unsubstituted heteroaryl group having 5 to 50 ring atoms, a substituted or unsubstituted alkyl group having 1 to 20 carbon atoms, a substituted or unsubstituted haloalkyl group having 1 to 20 carbon atoms, or a substituted or unsubstituted alkoxyl group having 1 to 20 carbon atoms.

The subscript n is an integer of 0 to 5. When n is an integer of 2 or more, $R^1$ groups may be the same or different from each other. The adjacent two $R^1$ groups may bond to each other to form a substituted or unsubstituted hydrocarbon ring.

$Ar^1$ represents a substituted or unsubstituted aryl group having 6 to 50 ring carbon atoms or a substituted or unsubstituted heteroaryl group having 5 to 50 ring atoms.

$Ar^2$ represents a hydrogen atom, a substituted or unsubstituted alkyl group having 1 to 20 carbon atoms, a substituted or unsubstituted haloalkyl group having 1 to 20 carbon atoms, a substituted or unsubstituted alkoxyl group having 1 to 20 carbon atoms, a substituted or unsubstituted aryl group having 6 to 50 ring carbon atoms, or a substituted or unsubstituted heteroaryl group having 5 to 50 ring atoms.

However, one of $Ar^1$ and $Ar^2$ is a substituted or unsubstituted condensed aromatic hydrocarbon group having 10 to 50 ring carbon atoms or a substituted or unsubstituted condensed aromatic heterocyclic group having 9 to 50 ring atoms.

$Ar^3$ represents a substituted or unsubstituted arylene group having 6 to 50 ring carbon atoms or a substituted or unsubstituted heteroarylene group having 5 to 50 ring atoms.

$L^1$, $L^2$, and $L^3$ each independently represent a single bond, a substituted or unsubstituted arylene group having 6 to 50 ring carbon atoms or a substituted or unsubstituted divalent condensed aromatic heterocyclic group having 9 to 50 ring atoms.

Examples of the aryl group having 6 to 50 ring carbon atoms include phenyl group, naphthyl group, anthryl group, phenanthryl group, naphthacenyl group, chrysenyl group, pyrenyl group, biphenyl group, terphenyl group, tolyl group, fluoranthenyl group, and fluorenyl group.

Examples of the heteroaryl group having 5 to 50 ring atoms include pyrrolyl group, furyl group, thienyl group, silolyl group, pyridyl group, quinolyl group, isoquinolyl group, benzofuryl group, imidazolyl group, pyrimidyl group, carbazolyl group, selenophenyl group, oxadiazolyl group, triazolyl group, pyrazinyl group, pyridazinyl group, triazinyl group, quinoxalinyl group, acridinyl group, imidazo[1,2-a]pyridinyl group, and imidazo[1,2-a]pyrimidinyl.

Examples of the alkyl group having 1 to 20 carbon atoms include methyl group, ethyl group, propyl group, butyl group, pentyl group, and hexyl group.

Examples of the haloalkyl group having 1 to 20 carbon atoms include the groups obtained by replacing one or more hydrogen atoms of the alkyl group mentioned above with at least one halogen atom selected from fluorine, chlorine, iodine, and bromine.

Examples of the alkyl moiety of the alkoxyl group having 1 to 20 carbon atoms include the alkyl group mentioned above.

Examples of the arylene groups include the groups obtained by removing one hydrogen atom from the aryl group mentioned above.

Examples of the divalent condensed aromatic heterocyclic group having 9 to 50 ring atoms include the groups obtained by removing one hydrogen atom from the heteroaryl group mentioned above.

The thickness of the electron transporting layer is preferably 1 to 100 nm, although not particularly limited thereto.

The electron injecting layer which may be formed adjacent to the electron transporting layer preferably includes an inorganic compound, such as an insulating material and a semiconductor in addition to the nitrogen-containing ring derivative. The insulating material or semiconductor incorporated into the electron injecting layer effectively prevents the leak of electric current to enhance the electron injecting properties.

The insulating material is preferably at least one metal compound selected from the group consisting of alkali metal chalcogenides, alkaline earth metal chalcogenides, alkali metal halides and alkaline earth metal halides. The alkali metal chalcogenide, etc. incorporated into the electron injecting layer further enhances the electron injecting properties. Preferred examples of the alkali metal chalcogenides include $Li_2O$, $K_2O$, $Na_2S$, $Na_2Se$ and $Na_2O$, and preferred examples of the alkaline earth metal chalcogenides include CaO, BaO, SrO, BeO, BaS and CaSe. Preferred examples of the alkali metal halides include LiF, NaF, KF, LiCl, KCl and NaCl. Examples of the alkaline earth metal halides include fluorides such as $CaF_2$, $BaF_2$, $SrF_2$, $MgF_2$ and $BeF_2$ and halides other than fluorides.

Examples of the semiconductor may include oxide, nitride or oxynitride each containing at least one element selected from the group consisting of Ba, Ca, Sr, Yb, Al, Ga, In, Li, Na, Cd, Mg, Si, Ta, Sb and Zn. The semiconductor may be used singly or in combination of two or more. The inorganic compound forming the electron injecting layer preferably forms a microcrystalline or amorphous insulating thin film. When the electron injecting layer is formed from such an insulating thin film, the thin film is made more uniform to decrease the pixel defects such as dark spots. Examples of such inorganic compound include alkali metal chalcogenides, alkaline earth metal chalcogenides, alkali metal halides and alkaline earth metal halide, each being described above.

The thickness of the layer including the insulating material or the semiconductor is preferably about 0.1 to 15 nm. The electron injecting layer may be included with the electron-donating dopant described above.

Hole Transporting Layer

The hole transporting layer is an organic layer formed between the light emitting layer and the anode and has a function of transporting holes from the anode to the light emitting layer. When the hole transporting layer is formed by two or more layers, the layer closer to the anode may be defined as the hole injecting layer in some cases. The hole injecting layer has a function of efficiently injecting holes from the anode to the organic layer unit.

An aromatic amine compound, for example, the aromatic amine derivative represented by formula (I), is also preferably used as the material for forming the hole transporting layer.

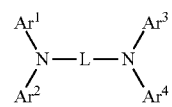

(I)

In formula (I), each of $Ar^1$ to $Ar^4$ represents a substituted or unsubstituted, non-fused or fused aromatic hydrocarbon group having 6 to 50 ring carbon atoms, a substituted or unsubstituted, non-fused or fused aromatic heterocyclic group having 5 to 50 ring atoms, or a group wherein the non-fused or fused aromatic hydrocarbon group and the non-fused or fused aromatic heterocyclic group are boned to each other.

L represents a substituted or unsubstituted, non-fused or fused aromatic hydrocarbon group having 6 to 50 ring carbon atoms or a substituted or unsubstituted, non-fused or fused aromatic heterocyclic group having 5 to 50 ring atoms.

Examples of the compound represented by formula (I) are shown below.

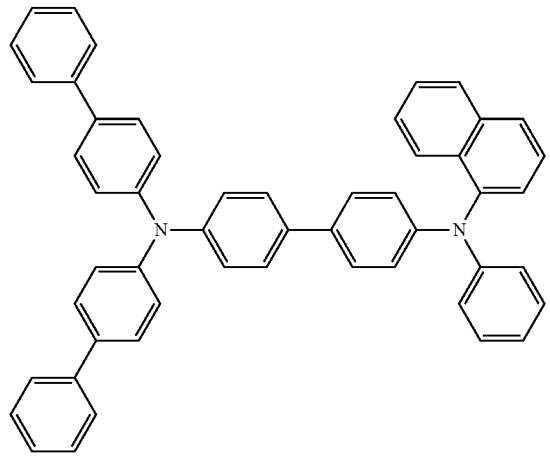

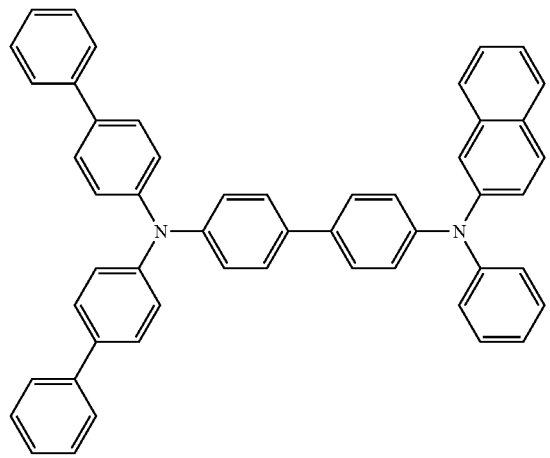

143
-continued
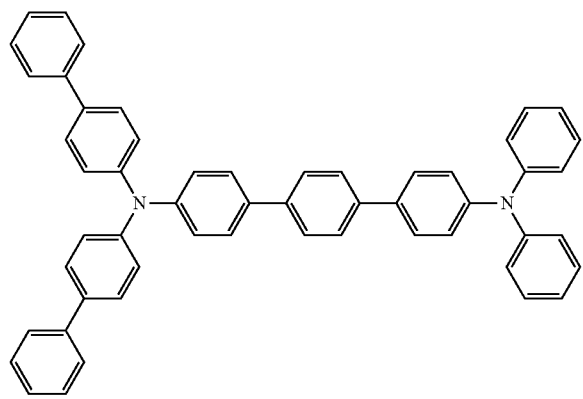
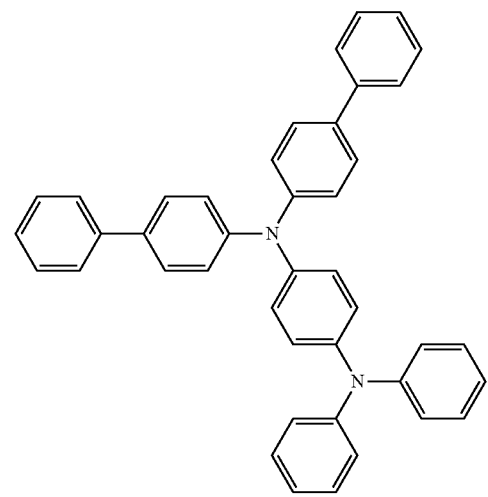
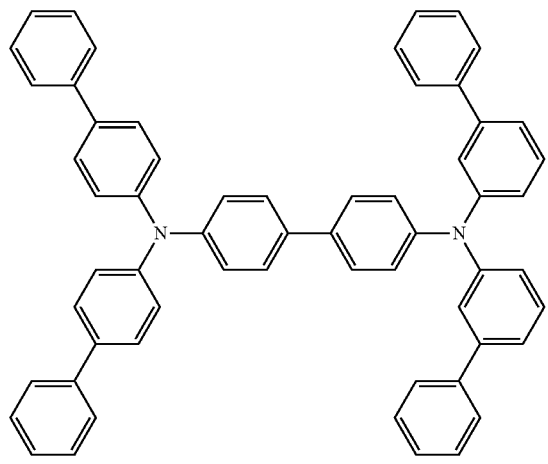
144
-continued
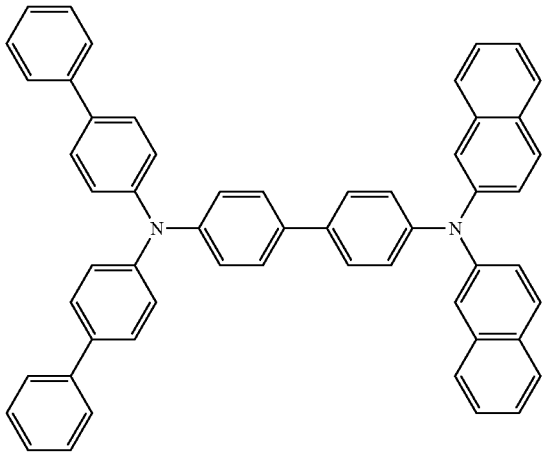
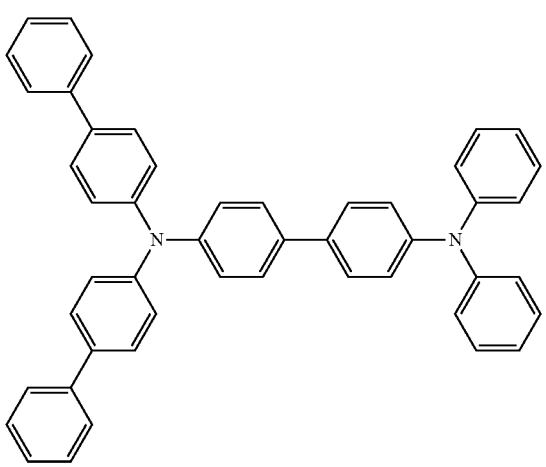
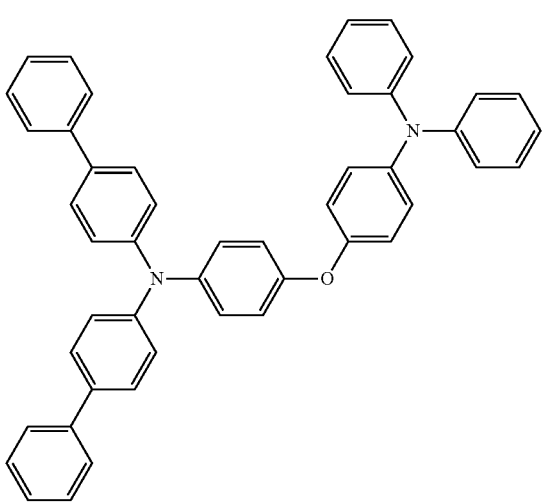

145
-continued
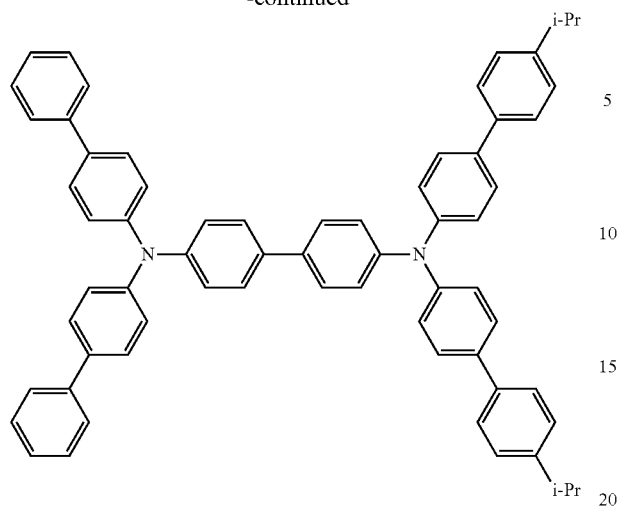
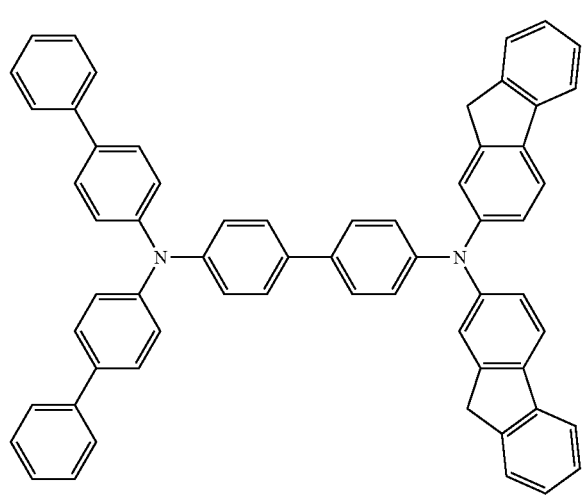
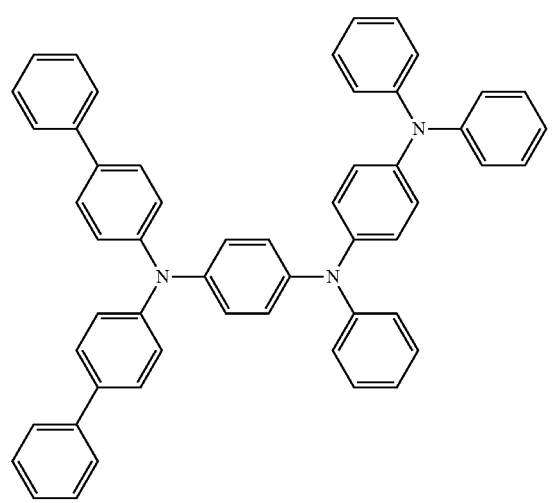
146
-continued
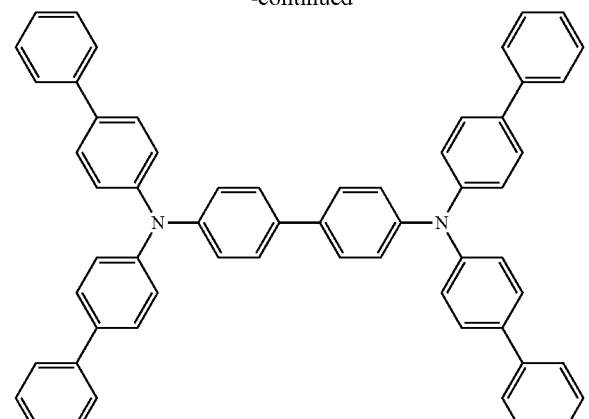
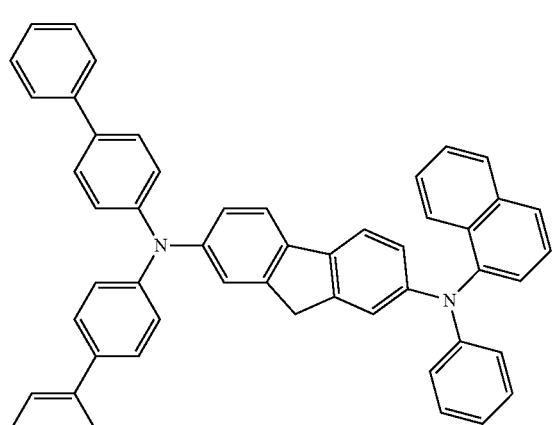
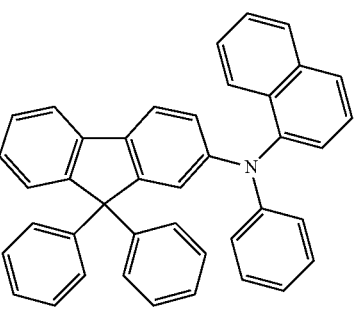

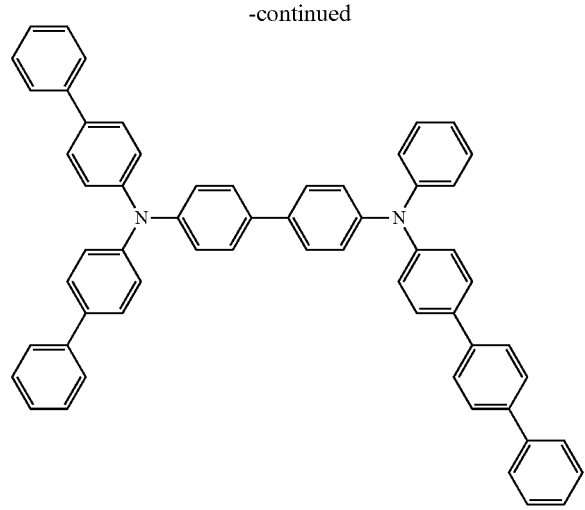
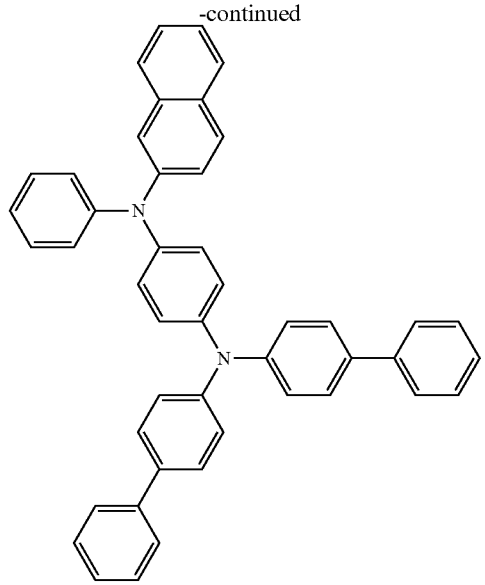
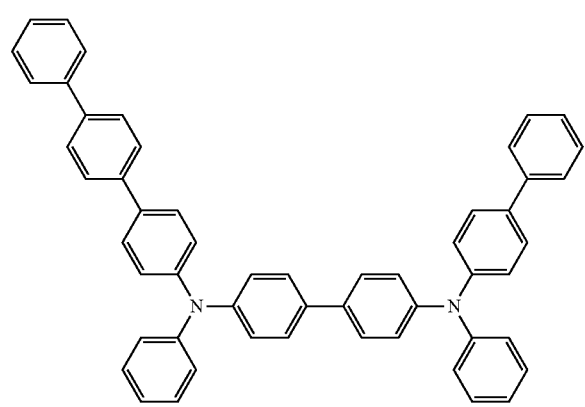
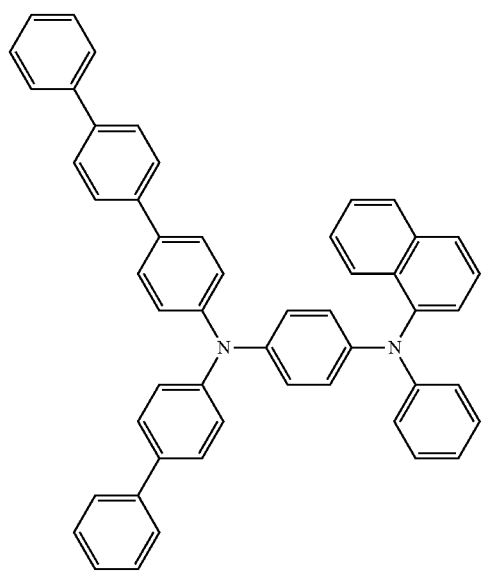
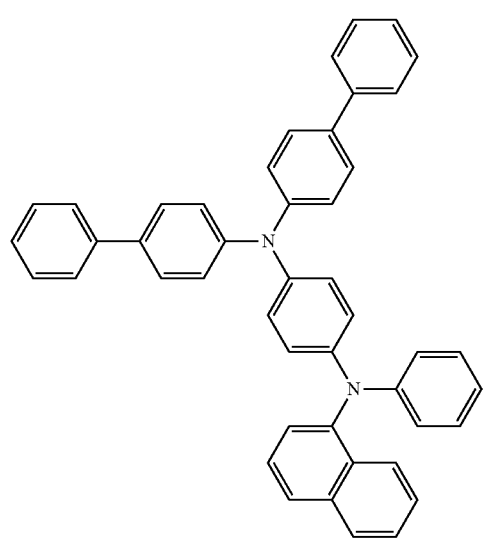
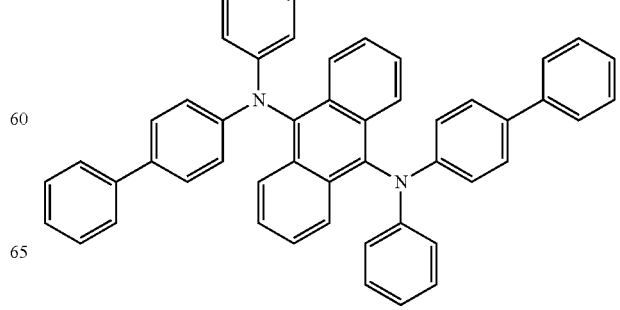

149
-continued
150
-continued
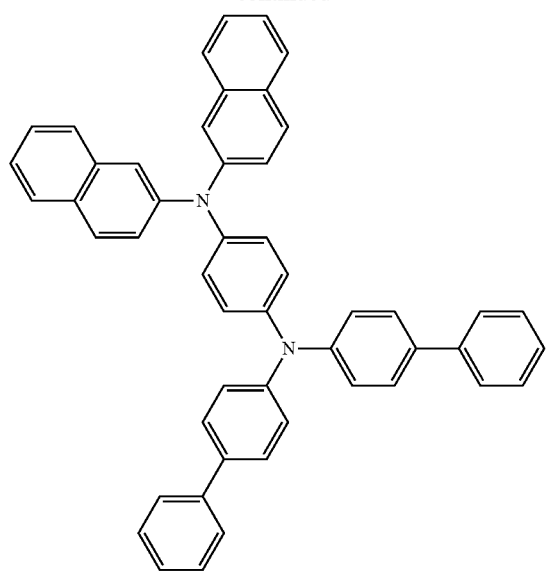
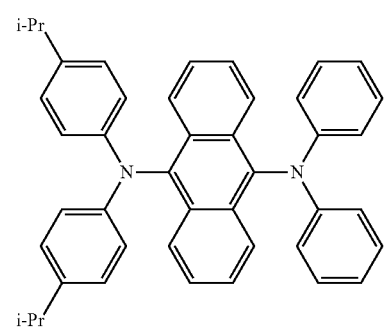
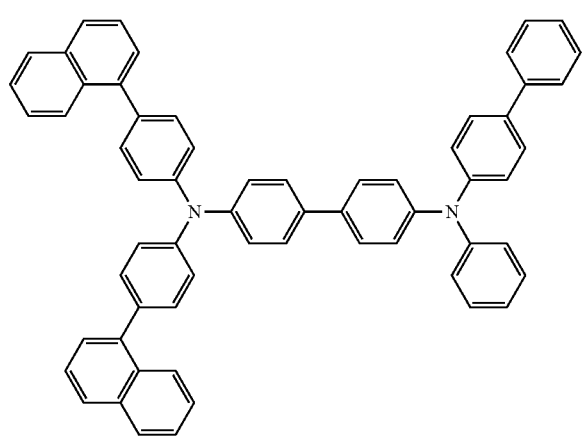
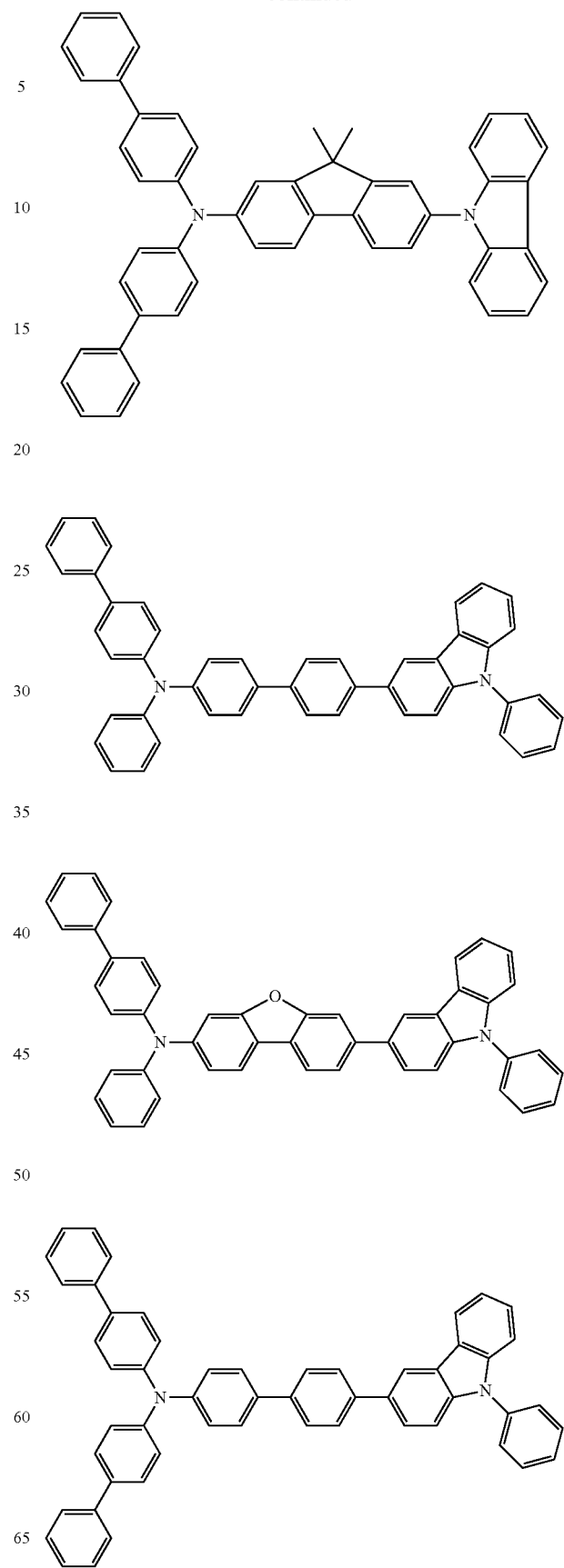

-continued
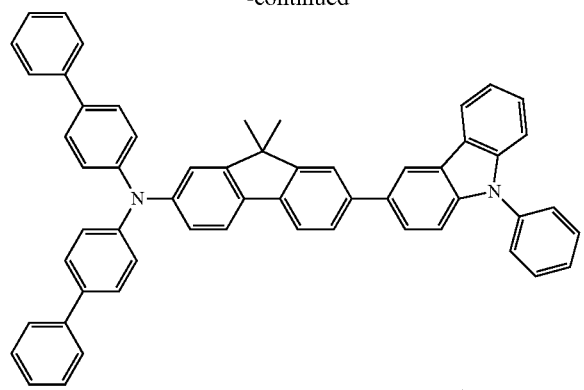
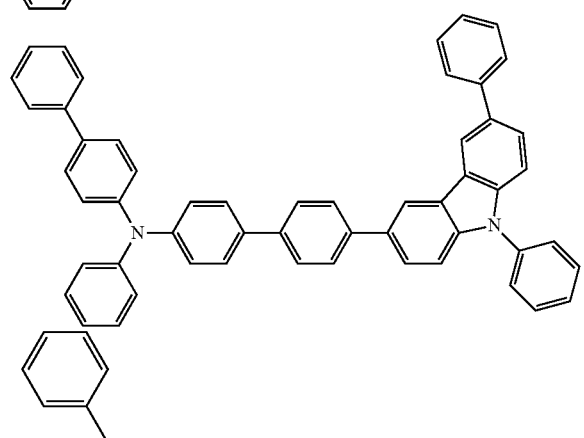
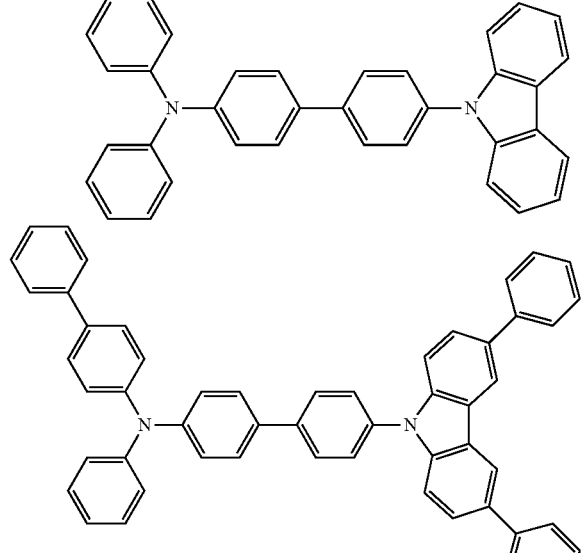
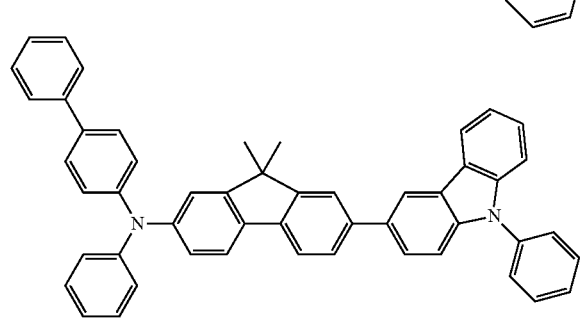
The aromatic amine represented by formula (II) is also preferably used as the material for forming the hole transporting layer.
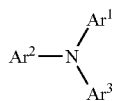
(II)
In formula (II), each of $Ar^1$ to $Ar^3$ is defined in the same manner as in the definition of $Ar^1$ to $Ar^4$ of formula (I). Examples of the compounds represented by formula (II) are shown below, although not limited thereto.
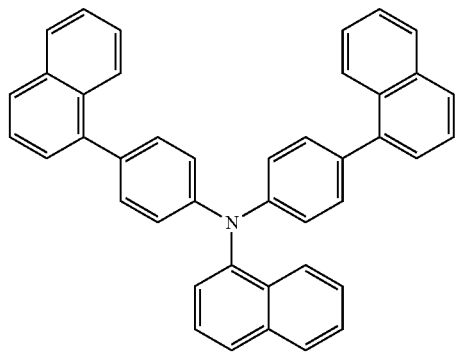
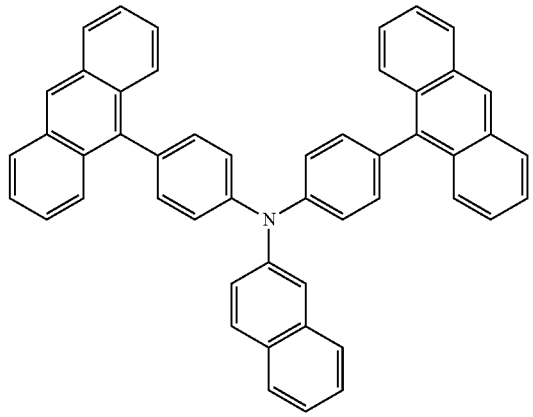
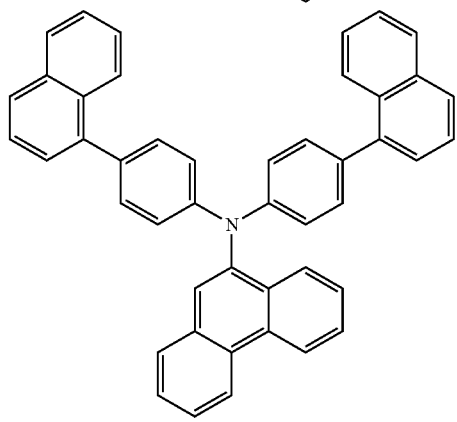

153
-continued
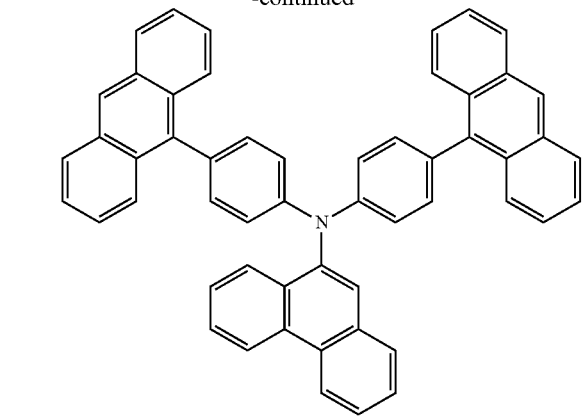
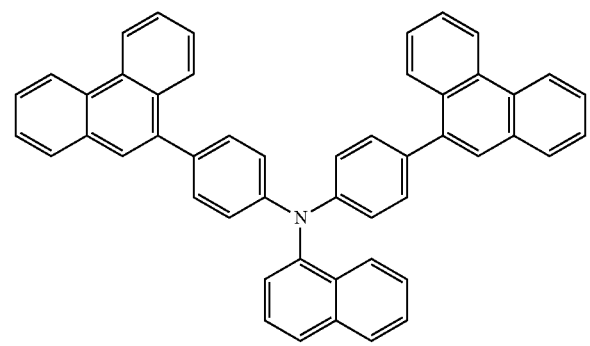
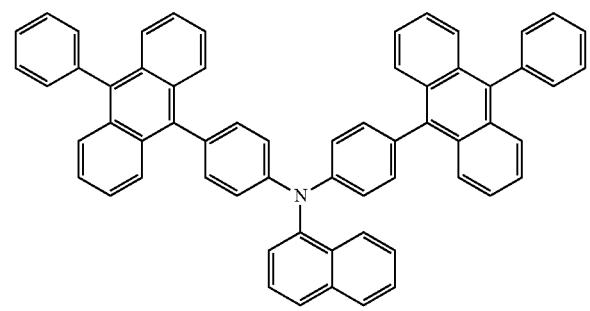
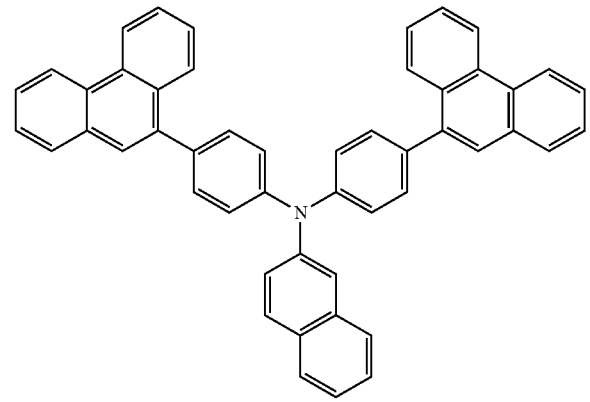
154
-continued
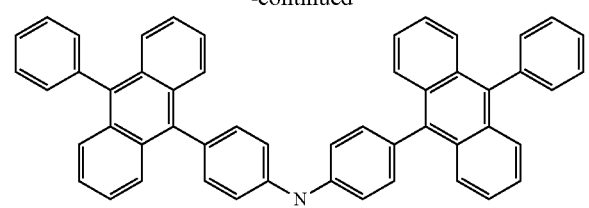
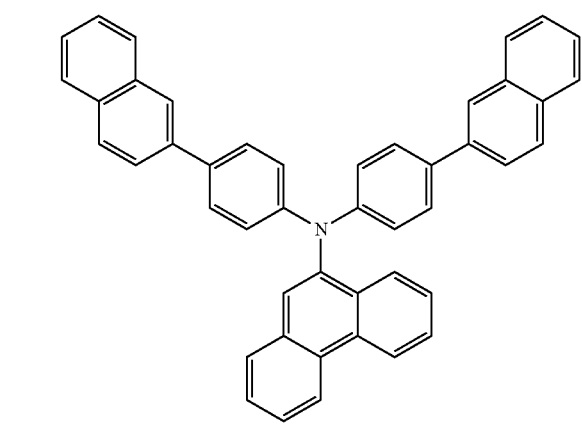
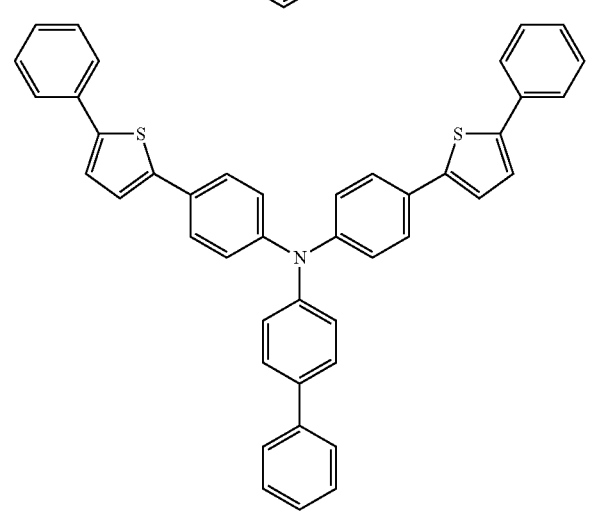
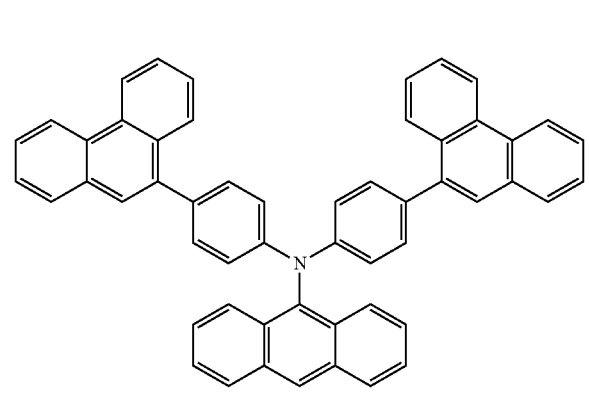

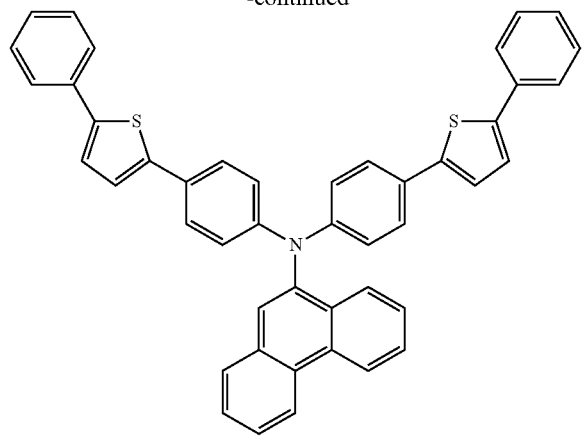

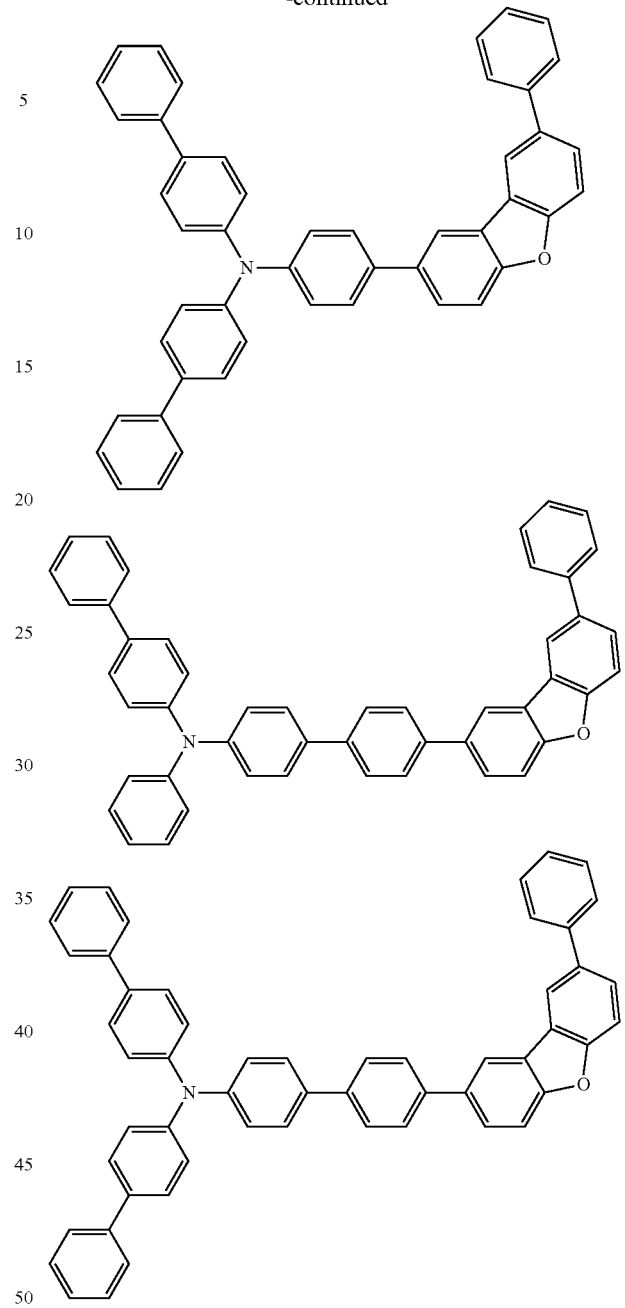

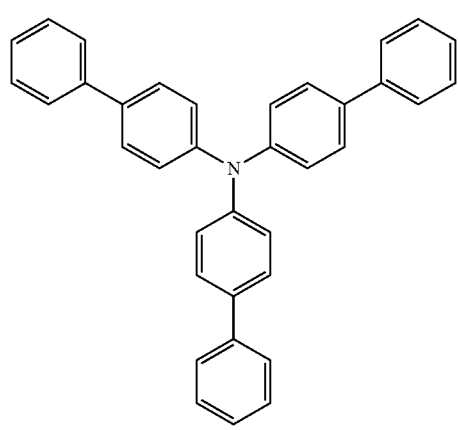

The hole transporting layer of the organic EL device of the invention may be made into two-layered structure of a first hole transporting layer (anode side) and a second hole transporting layer (cathode side).

The thickness of the hole transporting layer is preferably 10 to 200 nm, although not particularly limited thereto.

The organic EL device of the invention may have a layer comprising an acceptor material which is attached to the anode side of each of the hole transporting layer and the first hole transporting layer. With such a layer, it is expected that the driving voltage is lowered and the production cost is reduced.

The acceptor material is preferably a compound represented by formula (10):

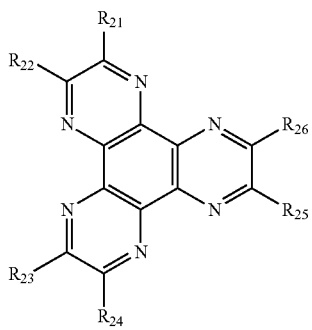

(10)

wherein $R_{21}$ to $R_{26}$ may be the same or different and each independently represent a cyano group, —$CONH_2$, a carboxyl group, or —$COOR_{27}$ wherein $R_{27}$ represents an alkyl group having 1 to 20 carbon atoms or a cycloalkyl group having 3 to 20 ring carbon atoms. One or more pairs of $R_{21}$ and $R_{22}$, $R_{23}$ and $R_{24}$, and $R_{25}$ and $R_{26}$ may bond to each other to form a group represented by —CO—O—CO—.

Examples of $R_{27}$ include methyl group, ethyl group, n-propyl group, isopropyl group, n-butyl group, isobutyl group, t-butyl group, cyclopentyl group, and cyclohexyl group.

The thickness of the layer comprising the acceptor material is preferably 5 to 20 nm, although not particularly limited thereto.

N/P Doping

The carrier injecting properties of the hole transporting layer and the electron transporting layer can be controlled by, as described in JP 3695714B, the doping (n) with a donor material or the doping (p) with an acceptor material.

A typical example of the n-doping is an electron transporting material doped with a metal, such as Li and Cs, and a typical example of the p-doping is a hole transporting material doped with an acceptor material such as, $F_4TCNQ$.

Space Layer

For example, in an organic EL device wherein a fluorescent light emitting layer and a phosphorescent light emitting layer are laminated, a space layer is disposed between the fluorescent light emitting layer and the phosphorescent light emitting layer to prevent the diffusion of excitons generated in the phosphorescent light emitting layer to the fluorescent light emitting layer or to control the carrier balance. The space layer may be disposed between two or more phosphorescent light emitting layers.

Since the space layer is disposed between the light emitting layers, a material combining the electron transporting ability and the hole transporting ability is preferably used for forming the space layer. To prevent the diffusion of triplet energy in the adjacent phosphorescent light emitting layer, the triplet energy of the material for the space layer is preferably 2.6 eV or more. The materials described with respect to the hole transporting layer are usable as the material for the space layer.

Blocking Layer

The organic EL device of the invention preferably has a blocking layer, such as an electron blocking layer, a hole blocking layer, and a triplet blocking layer, which is disposed adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer. The material for organic EL device of the invention is also usable as the material for the hole blocking layer.

The triplet blocking layer prevents, as described below, the diffusion of triplet excitons generated in the light emitting layer to adjacent layers and has a function of confining the triplet excitons in the light emitting layer, thereby preventing the deactivation of energy on molecules other than the emitting dopant of triplet excitons, for example, on molecules in the electron transporting layer.

If a phosphorescent device having a triplet blocking layer satisfies the following energy relationship:

$$E^T_d < E^T_{TB}$$

wherein $E^T_d$ is the triplet energy of the phosphorescent dopant in the light emitting layer and $E^T_{TB}$ is the triplet energy of the compound forming the triplet blocking layer, the triplet excitons of phosphorescent dopant are confined (not diffuse to other molecules). Therefore, the energy deactivation process other than the emission on the phosphorescent dopant may be prevented to cause the emission with high efficiency. However, even in case of satisfying the relationship of $E^T_d < E^T_{TB}$, the triplet excitons may move into other molecules if the energy difference ($\Delta E^T = E^T_{TB} - E^T_d$) is small, because the energy difference $\Delta E^T$ may be overcome by the absorption of ambient heat energy when driving a device at around room temperature as generally employed in practical drive of device. As compared with the fluorescent emission, the phosphorescent emission is relatively likely to be affected by the diffusion of excitons due to the heat absorption because the lifetime of triplet excitons is longer. Therefore, as for the energy difference $\Delta E^T$, the larger as compared with the heat energy of room temperature, the better. The energy difference $\Delta E^T$ is more preferably 0.1 eV or more and particularly preferably 0.2 eV or more.

The triplet energy referred to herein was determined as follows.

A sample was dissolved in EPA solvent (diethyl ether:isopentane:ethanol=5:5:2 (by volume)) in a concentration of 10 μmol/L to prepare a specimen for phosphorescence measurement. The specimen for phosphorescence measurement was placed in a quartz cell and irradiated with excitation ray at 77 K, and the emitted phosphorescence was measured. Using the measured result, the triplet energy was determined as the value calculated from the following conversion formula:

$$E^T(eV) = 1239.85/\lambda_{edge}$$

wherein $\lambda_{edge}$ is determined as follows.

On the phosphorescence spectrum with a vertical axis of phosphorescent intensity and a horizontal axis of wavelength, a line tangent to the rising portion at the short-wavelength side of the phosphorescent spectrum was drawn, and the wavelength (nm) at the intersection of the tangent line and the horizontal axis was expressed by "$\lambda_{edge}$."

A material satisfying the following relationship:

$$A_b - A_h \leq 0.1\ eV$$

wherein $A_b$ is the electron affinity of the blocking layer material and $A_h$ is the electron affinity of the host material in the light emitting layer, is preferably used as the host material in the light emitting layer.

The electron affinity is defined as the amount of energy released or absorbed when one electron is added to a molecule. The electron affinity is expressed by a positive sign when the energy is released and a negative sign when the energy is absorbed. Using the ionization potential Ip and the optical energy gap Eg(S), the electron affinity Af is expressed by:

$Af=Ip-Eg(S)$.

The ionization potential Ip is the amount of energy required to remove an electron from a compound to ionize the compound. In the present invention, Ip is a positive value measured by a photoelectronic spectrophotometer (AC-3, manufactured by Riken Keiki Co., Ltd.) in the atmosphere. The optical energy gap Eg(S) is the difference between the conduction level and the valence level. In the present invention, Eg(S) is a positive value which is determined by measuring an ultraviolet/visible absorption spectrum of a diluted dichloromethane solution of a material, drawing a line tangent to the spectrum at the long-wavelength side, and converting the wavelength of the intersection between the tangent line and the base line (zero absorption) to the unit of energy.

The electron mobility of the material for the triplet blocking layer is preferably $10^{-6}$ cm$^2$/Vs or more at an electric field strength in a range of 0.04 to 0.5 MV/cm. There are several methods for measuring the electron mobility of organic material, for example, Time of Flight method. In the present invention, the electron mobility is determined by impedance spectroscopy.

The electron mobility of the electron injecting layer is preferably $10^{-6}$ cm$^2$/Vs or more at an electric field strength in a range of 0.04 to 0.5 MV/cm. Within the above range, the injection of electrons from the cathode to the electron transporting layer is promoted and the injection of electrons to the adjacent blocking layer and light emitting layer is also promoted, thereby enabling to drive a device at lower voltage.

EXAMPLES

The present invention will be described in more detail with reference to the examples. However, it should be noted that the scope of the invention is not limited to the following examples.

Intermediate Synthesis 1-1

Synthesis of Intermediate 1-1

In an argon atmosphere, 55 g (201.3 mmol) of 2-bromo-9,9-dimethylfluorene was added with 23 g (90.6 mmol) of iodine, 9.4 g (41.2 mmol) of periodic acid dihydrate, 42 ml of water, 360 ml of acetic acid, and 11 ml of sulfuric acid. The resultant mixture was stirred at 65° C. for 30 min and further stirred at 90° C. for 6 h.

After the reaction, the reaction product was poured into iced water. The precipitated crystals were collected by filtration and washed with water and then methanol to obtain 61 g of white solid, which was identified as the following intermediate 1-1 by FD-MS (Field Desorption Mass Spectrometry) (yield: 76%).

Intermediate 1-1

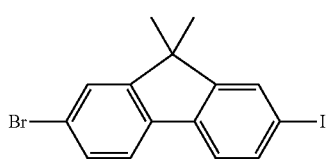

Intermediate Synthesis 1-2

Synthesis of Intermediate 1-2

The reaction of Intermediate Synthesis 1-1 was repeated except for using 46.9 g of 4-bromobiphenyl in place of 2-bromo-9,9-dimethylfluorene to obtain 50.6 g of white solid, which was identified as the following intermediate 1-2 by FD-MS (yield: 70%).

Intermediate 1-2

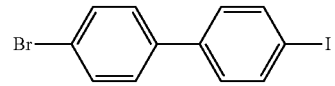

Intermediate Synthesis 1-3

Synthesis of Intermediate 1-3

In an argon atmosphere, 78.0 g (0.46 mol) of dibenzofuran was added with 600 ml of dehydrated tetrahydrofuran. The resultant mixture was cooled to −30° C. and added dropwise with 300 ml (0.50 mol) of a 1.65 M hexane solution of n-butyllithium. The temperature was raised to room temperature over one hour under stirring. The mixture was stirred at room temperature for 5 h, cooled to −60° C., and then added dropwise with 60 ml (0.70 mol) of 1,2-dibromoethane over one hour.

After stirring at room temperature for 15 h, the mixture was poured into 1000 ml of iced water and extracted with dichloromethane. The organic layer was washed with brine, dried over MgSO$_4$, filtered, and then concentrated. The concentrate was purified by silica gel column chromatography and washed with tetrahydrofuran/methanol to obtain 70 g of solid, which was identified as the following intermediate 1-3 by FD-MS (yield: 62%).

Intermediate 1-3

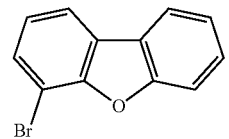

Intermediate Synthesis 1-4

Synthesis of Intermediate 1-4

In an argon atmosphere, 28.3 g (100.0 mmol) of 4-iodo-bromobenzene, 22.3 g (105.0 mmol) of dibenzofuran-4-boronic acid and 2.31 g (2.00 mmol) of Pd[PPh$_3$]$_4$ were added with 150 ml of toluene, 150 ml of dimethoxyethane and 150 ml (300.0 mmol) of a 2 M aqueous solution of Na$_2$CO$_3$. The resultant mixture was stirred for 10 h while refluxing under heating.

After the reaction, the mixture was extracted with dichloromethane in a separatory funnel. The organic layer was dried over MgSO$_4$, filtered, and then concentrated. The concentrate was purified by silica gel column chromatography to obtain 26.2 g of white solid, which was identified as the following intermediate 1-4 by FD-MS (yield: 81%).

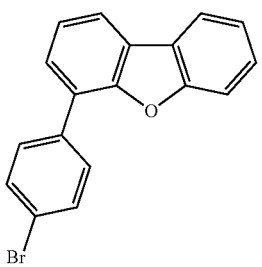

Intermediate 1-4

Intermediate Synthesis 1-5

Synthesis of Intermediate 1-5

In a nitrogen atmosphere, 150 g (0.89 mol) of dibenzofuran was dissolved in 1000 ml of acetic acid under heating. After adding 188 g (1.18 mol) of bromine dropwise, the resultant mixture was stirred at room temperature for 20 h. The precipitated crystals were collected by filtration and successively washed with acetic acid and water. The crude product was recrystallized from methanol several times to obtain 66.8 g of white crystal, which was identified as the following intermediate 1-5 by FD-MS (yield: 30%).

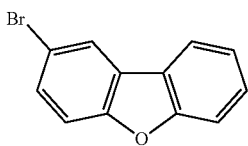

Intermediate 1-5

Intermediate Synthesis 1-6

Synthesis of Intermediate 1-6

In an argon atmosphere, 48.2 g (261.6 mmol) of dibenzothiophene was added with 480 ml of dehydrated tetrahydrofuran. The resultant mixture was cooled to −30° C. and added with 164 ml (262.0 mol) a 1.60 M hexane solution of n-butyllithium dropwise. The temperature was raised to room temperature over one hour under stirring. After stirring at room temperature for 3 h, the mixture was cooled to −60° C. and added with a solution of 73.7 g (393 mmol) of 1,2-dibromoethane in 50 ml dehydrated tetrahydrofuran dropwise over one hour.

After stirring for 15 h at room temperature, the mixture was poured into 400 ml of iced water and extracted with toluene. The organic layer was washed with brine, dried over MgSO$_4$, filtered, and then concentrated. The concentrate was purified by silica gel column chromatography. The crude product was recrystallized from heptane several times to obtain 33.1 g of white crystal, which was identified as the following intermediate 1-6 by FD-MS (yield: 48%).

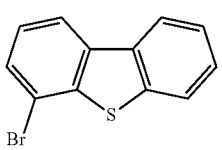

Intermediate 1-6

Intermediate Synthesis 2-1

Synthesis of Intermediate 2-1

In an argon atmosphere, 21.9 g (100.0 mmol) of N-phenyl-1-naphthylamine, 31.1 g (110.0 mmol) of 4-iodobromobenzene, 3.8 g (20.0 mmol) of copper iodide (I), 4.0 g (45.0 mmol) of N,N'-dimethylethylenediamine, and 19.2 g (200.0 mmol) of sodium t-butoxide were added with 200 ml of dehydrated toluene. The resultant mixture was allowed to react at 110° C. for 8 h. After the reaction, the reaction mixture was extracted with toluene, and the organic layer was dried over MgSO$_4$ and then concentrated. The concentrate was purified by silica gel column chromatography. The crude product was recrystallized from toluene, collected by filtration, and dried to obtain 33.6 g of white solid, which was identified as N-(4-bromophenyl)-1-naphthylphenylamine by FD-MS (yield: 90%).

In an argon atmosphere, 33.6 g (89.8 mmol) of N-(4-bromophenyl)-1-naphthylphenylamine was added with 200 ml of dehydrated xylene, and the resultant mixture was cooled to −30° C. After adding 60 ml (96.0 mmol) of a 1.6 M hexane solution of n-butyllithium, the reaction was allowed to proceed for one hour. After cooling to −70° C., the reaction solution was added with 45.9 g (244.0 mmol) of triisopropyl borate, gradually heated, and then stirred at room temperature for one hour. After adding 64 ml of a 10% hydrochloric acid, the stirring was further continued. After the reaction, the reaction solution was extracted with ethyl acetate. The organic layer was washed with water, dried over Na$_2$SO$_4$, and then concentrated. The concentrate was washed with hexane to obtain 15.2 g of 4-[N-(1-naphthyl)-N-phenylamino]phenylboronic acid as white solid (yield: 50%).

In an argon atmosphere, 9.8 g (40.0 mmol) of 3-bromocarbazole and 14.9 g (44.0 mmol) of 4-[N-(1-naphthyl)-N-phenylamino]phenylboronic acid were added with 40 ml (80.0 mmol) of a 2 M aqueous solution of Na$_2$CO$_3$, 200 ml of dioxane, and 0.33 g (0.4 mmol) of PdCl$_2$ (dppf), and the resultant mixture was stirred for 12 h while refluxing under heating.

After the reaction, the mixture was cooled to room temperature, added with water (100 ml), and extracted with dichloromethane in a separatory funnel. The extract was dried over MgSO$_4$, filtered, and then concentrated. The concentrate was purified by silica gel column chromatography to obtain 9.2 g of white solid, which was identified as the following intermediate 2-1 by FD-MS (yield: 50%).

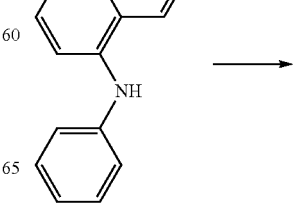

-continued

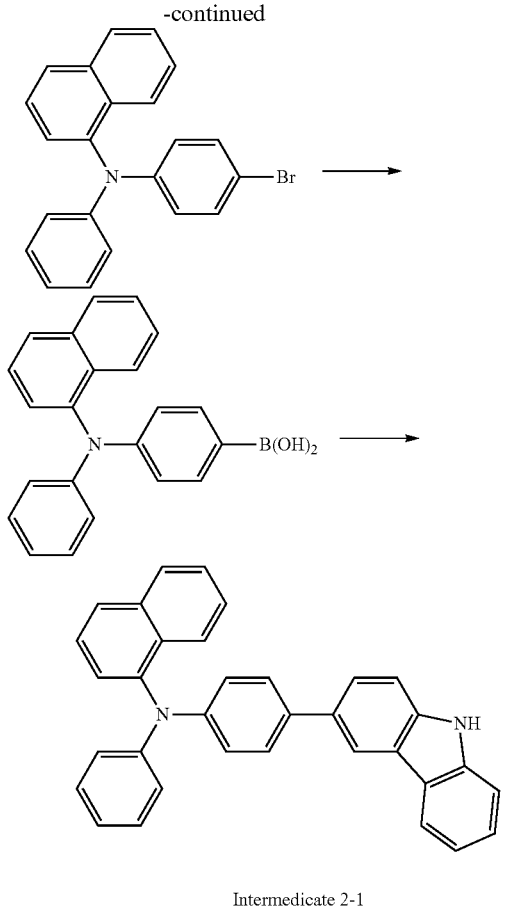

Intermedicate 2-1

Intermediate Synthesis 2-2

Synthesis of Intermediate 2-2

The reaction of Intermediate Synthesis 2-1 was repeated except for using 24.5 g of N-phenyl-4-biphenylamine in place of N-phenyl-1-naphthylamine to obtain 9.7 g of white solid, which was identified as the following intermediate 2-2 by FD-MS (yield: 20%).

Intermediate 2-2

Intermediate Synthesis 2-3

Synthesis of Intermediate 2-3

The reaction of Intermediate Synthesis 2-1 was repeated except for using 32.1 g of bis(4-biphenylyl)amine in place of N-phenyl-1-naphthylamine to obtain 14.1 g of white solid, which was identified as the following intermediate 2-3 by FD-MS (yield: 25%).

Intermediate 2-3

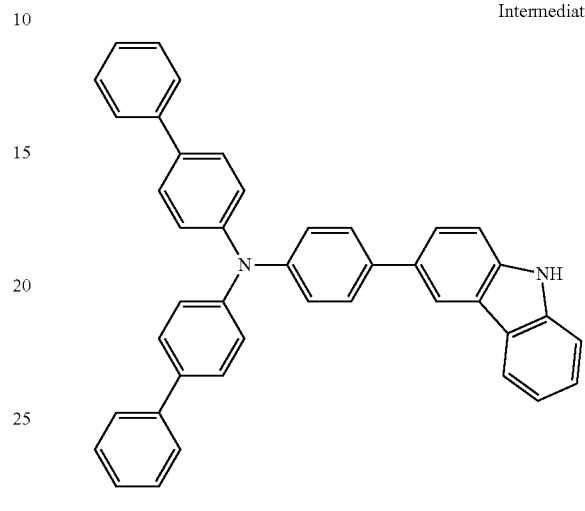

Intermediate Synthesis 2-4

Synthesis of Intermediate 2-4

In an argon atmosphere, 30.9 g (100.0 mmol) of 4-bromo-p-terphenyl, 9.3 g (100.0 mmol) of aniline, 13.0 g (135.3 mmol) of sodium t-butoxide, 460 mg (0.5 mmol) of tris(dibenzylideneacetone)dipalladium(0), and 210 mg (1.04 mmol) of tri-t-butylphosphine were added with 500 ml of dehydrated toluene, and the reaction was allowed to proceed at 80° C. for 8 h.

After cooling, the reaction mixture was added with 2.5l of water and then filtered through celite. The filtrate was extracted with toluene. The extract was dried over anhydrous magnesium sulfate and concentrated under reduced pressure. The obtained residue was purified by silica gel column chromatography, recrystallized from toluene, collected by filtration, and then dried to obtain 15.7 g of pale yellow solid, which was identified as the following intermediate 2-4 by FD-MS (yield: 49%).

Intermediate 2-4

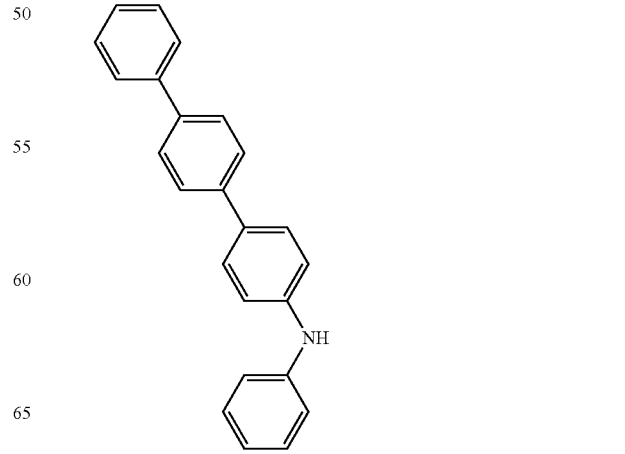

Intermediate Synthesis 2-5

Synthesis of Intermediate 2-5

The reaction of Intermediate Synthesis 2-1 was repeated except for using 32.1 g of the intermediate 2-4 in place of N-phenyl-1-naphthylamine to obtain 12.4 g of white solid, which was identified as the following intermediate 2-5 by FD-MS (yield: 22%).

Intermediate 2-5

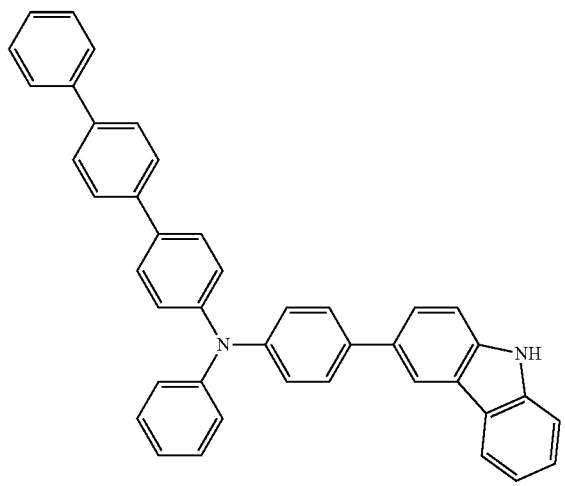

Intermediate Synthesis 2-6

Synthesis of Intermediate 2-6

The reaction of Intermediate Synthesis 2-4 was repeated except for using 23.3 g of 4-bromobiphenyl in place of 4-bromo-p-terphenyl and 20.9 g of 9,9-dimethyl-2-aminofluorene in place of aniline to obtain 20.6 g of pale yellow solid, which was identified as the following intermediate 2-6 by FD-MS (yield: 57%).

Intermediate 2-6

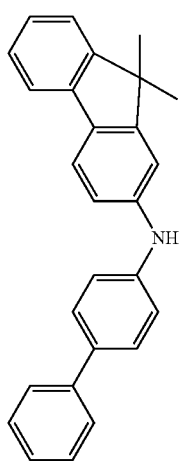

Intermediate Synthesis 2-7

Synthesis of Intermediate 2-7

The reaction of Intermediate Synthesis 2-1 was repeated except for using 36.1 g of the intermediate 2-6 in place of N-phenyl-1-naphthylamine to obtain 15.1 g of white solid, which was identified as the following intermediate 2-7 by FD-MS (yield: 25%).

Intermediate 2-7

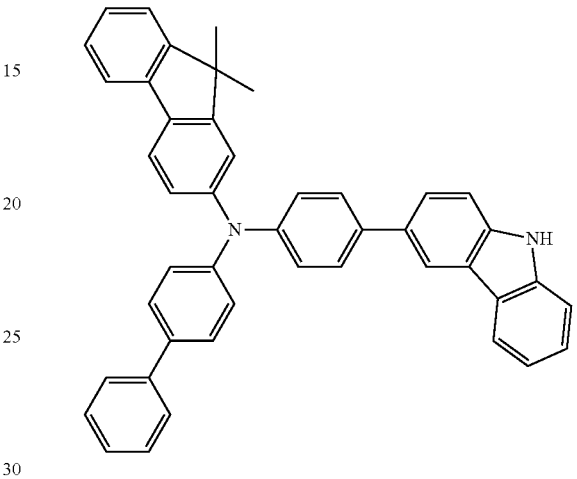

Intermediate Synthesis 2-8

Synthesis of Intermediate 2-8

The reaction of Intermediate Synthesis 2-1 was repeated except for using 39.5 g of the intermediate 1-2 in place of 4-bromoiodobenzene to obtain 16.1 g of white solid, which was identified as the following intermediate 2-8 by FD-MS (yield: 30%).

Intermediate 2-8

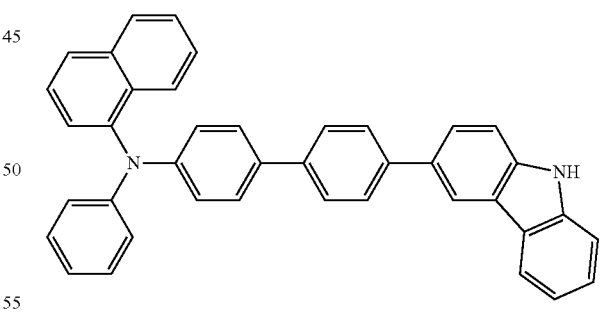

Intermediate Synthesis 2-9

Synthesis of Intermediate 2-9

The reaction of Intermediate Synthesis 2-1 was repeated except for using 24.5 g of N-phenyl-4-biphenylamine in place of N-phenyl-1-naphthylamine and 39.5 g of the intermediate 1-2 in place of 4-bromoiodobenzene to obtain 15.8 g of white solid, which was identified as the following intermediate 2-9 by FD-MS (yield: 28%).

Intermediate 2-9

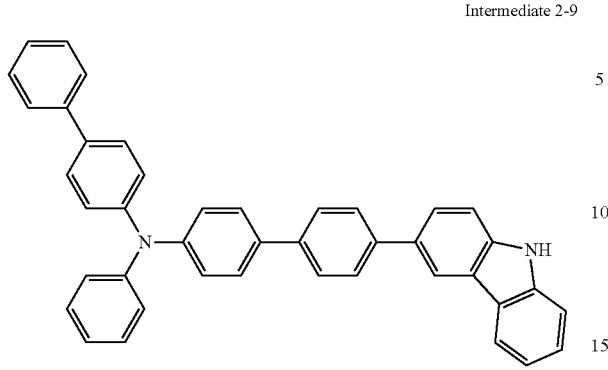

Intermediate Synthesis 2-10

Synthesis of Intermediate 2-10

The reaction of Intermediate Synthesis 2-1 was repeated except for using 32.1 g of bis(4-biphenylyl)amine in place of N-phenyl-1-naphthylamine and 39.5 g of the intermediate 1-2 in place of 4-bromoiodobenzene to obtain 12.8 g of white solid, which was identified as the following intermediate 2-10 by FD-MS (yield: 20%).

Intermediate 2-10

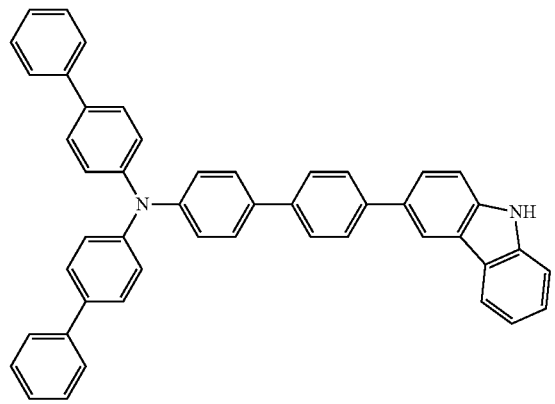

Intermediate Synthesis 2-11

Synthesis of Intermediate 2-11

The reaction of Intermediate Synthesis 2-1 was repeated except for using 43.9 g of the intermediate 1-1 in place of 4-bromoiodobenzene to obtain 13.3 g of white solid, which was identified as the following intermediate 2-11 by FD-MS (yield: 23%).

Intermediate 2-11

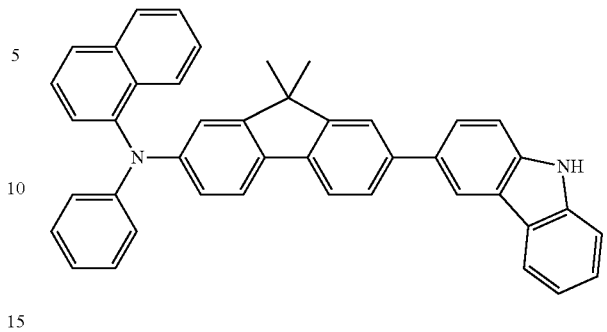

Intermediate Synthesis 2-12

Synthesis of Intermediate 2-12

The reaction of Intermediate Synthesis 2-1 was repeated except for using 32.1 g of bis(4-biphenylyl)amine in place of N-phenyl-1-naphthylamine and 43.9 g of the intermediate 1-1 in place of 4-bromoiodobenzene to obtain 12.2 g of white solid, which was identified as the following intermediate 2-12 by FD-MS (yield: 18%).

Intermediate 2-12

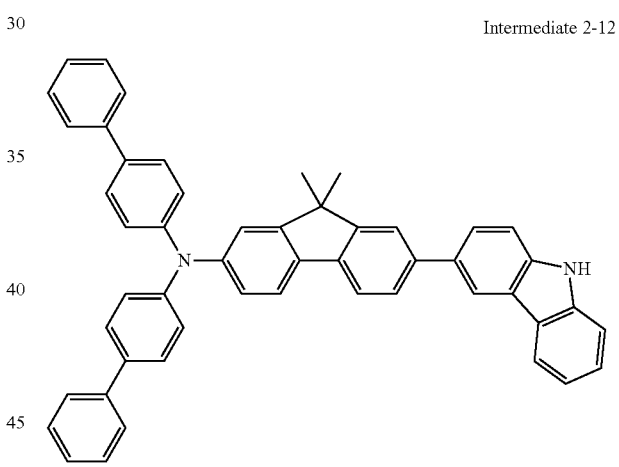

Synthesis Example 1

Production of Aromatic Amine Derivative (H1)

In an argon atmosphere, 2.5 g (10.0 mmol) of the intermediate 1-3, 4.6 g (10.0 mmol) of the intermediate 2-1, 0.14 g (0.15 mmol) of $Pd_2(dba)_3$, 0.087 g (0.3 mmol) of $P(tBu)_3HBF_4$, and 1.9 g (20.0 mmol) of sodium t-butoxide were added with 50 ml of dehydrated xylene, and the resultant mixture was refluxed for 8 h under heating.

After the reaction, the reaction solution was cooled to 50° C. and filtered through celite and silica gel, and the filtrate was concentrated. The obtained concentrate was purified by silica gel column chromatography to obtain white solid. The crude product was recrystallized from toluene to obtain 3.1 g of white crystal, which was identified as the following aromatic amine derivative (H1) by FD-MS (yield: 50%).

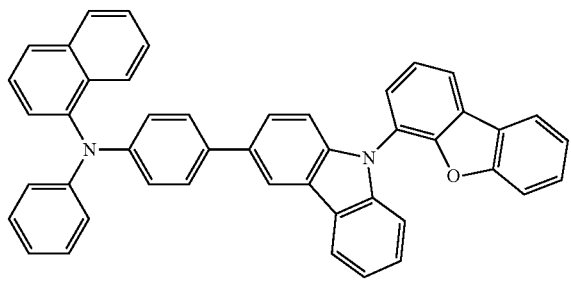

H1

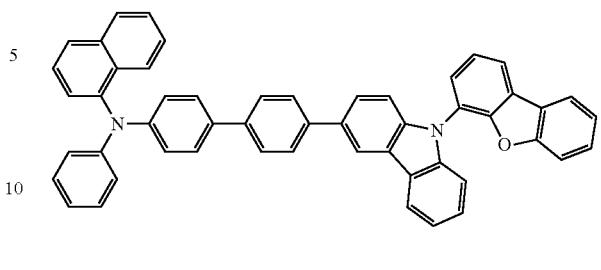

H3

Synthesis Example 2

Production of Aromatic Amine Derivative (H2)

The reaction of Synthesis Example 1 was repeated except for using 3.2 g of the intermediate 1-4 in place of the intermediate 1-3 to obtain 4.2 g of white crystal, which was identified as the following aromatic amine derivative (H2) by FD-MS (yield: 60%).

Synthesis Example 4

Production of Aromatic Amine Derivative (H4)

The reaction of Synthesis Example 1 was repeated except for using 5.8 g of the intermediate 2-11 in place of the intermediate 2-1 to obtain 3.5 g of white crystal, which was identified as the following aromatic amine derivative (H4) by FD-MS (yield: 47%).

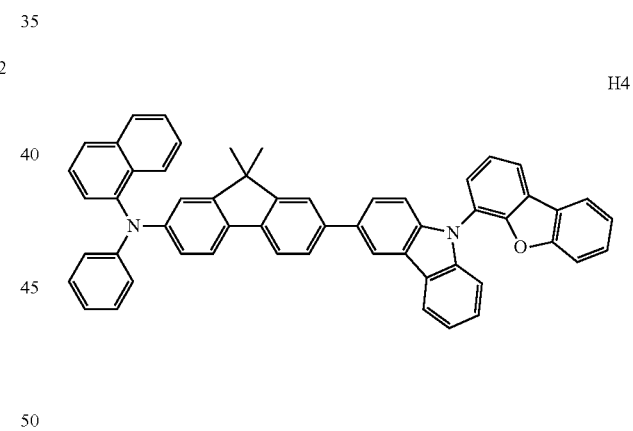

H2

H4

Synthesis Example 3

Production of Aromatic Amine Derivative (H3)

The reaction of Synthesis Example 1 was repeated except for using 5.4 g of the intermediate 2-8 in place of the intermediate 2-1 to obtain 3.5 g of white crystal, which was identified as the following aromatic amine derivative (H3) by FD-MS (yield: 50%).

Synthesis Example 5

Production of Aromatic Amine Derivative (H5)

The reaction of Synthesis Example 1 was repeated except for using 2.5 g of the intermediate 1-5 in place of the intermediate 1-3 to obtain 3.4 g of white crystal, which was identified as the following aromatic amine derivative (H5) by FD-MS (yield: 55%).

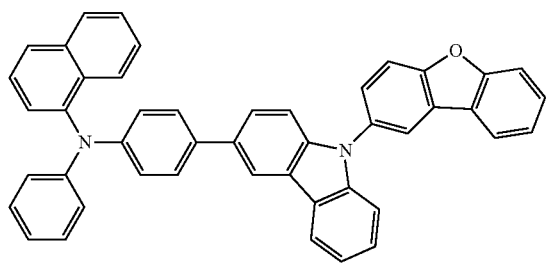

Synthesis Example 6

Production of Aromatic Amine Derivative (H6)

The reaction of Synthesis Example 1 was repeated except for using 4.9 g of the intermediate 2-2 in place of the intermediate 2-1 to obtain 3.3 g of white crystal, which was identified as the following aromatic amine derivative (H6) by FD-MS (yield: 50%).

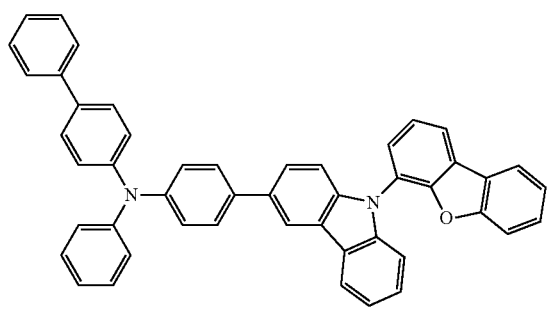

Synthesis Example 7

Production of Aromatic Amine Derivative (H7)

The reaction of Synthesis Example 1 was repeated except for using 3.2 g of the intermediate 1-4 in place of the intermediate 1-3 and 4.9 g of the intermediate 2-2 in place of the intermediate 2-1 to obtain 4.5 g of white crystal, which was identified as the following aromatic amine derivative (H7) by FD-MS (yield: 62%).

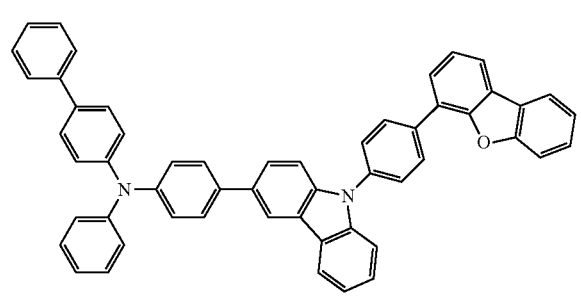

Synthesis Example 8

Production of Aromatic Amine Derivative (H8)

The reaction of Synthesis Example 1 was repeated except for using 5.6 g of the intermediate 2-9 in place of the intermediate 2-1 to obtain 3.5 g of white crystal, which was identified as the following aromatic amine derivative (H8) by FD-MS (yield: 48%).

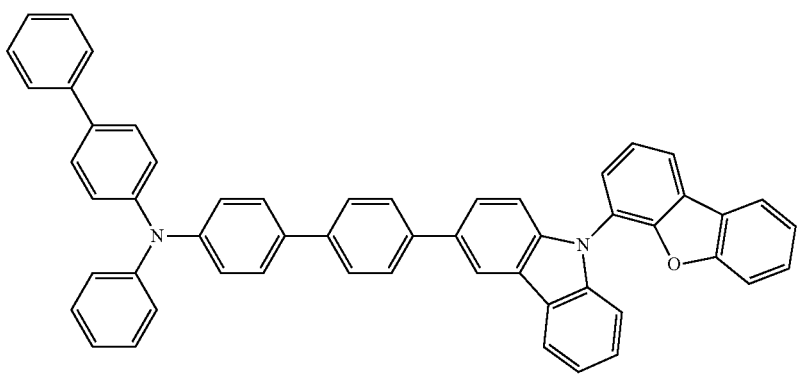

Synthesis Example 9

Production of Aromatic Amine Derivative (H9)

The reaction of Synthesis Example 1 was repeated except for using 5.6 g of the intermediate 2-3 in place of the intermediate 2-1 to obtain 3.4 g of white crystal, which was identified as the following aromatic amine derivative (H9) by FD-MS (yield: 47%).

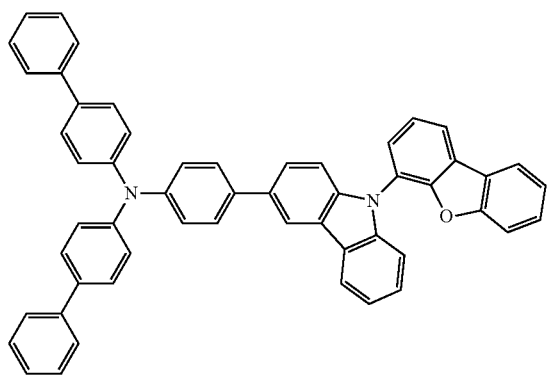

H9

Synthesis Example 10

Production of Aromatic Amine Derivative (H10)

The reaction of Synthesis Example 1 was repeated except for using 3.2 g of the intermediate 1-4 in place of the intermediate 1-3 and 5.6 g of the intermediate 2-3 in place of the intermediate 2-1 to obtain 4.4 g of white crystal, which was identified as the following aromatic amine derivative (H10) by FD-MS (yield: 55%).

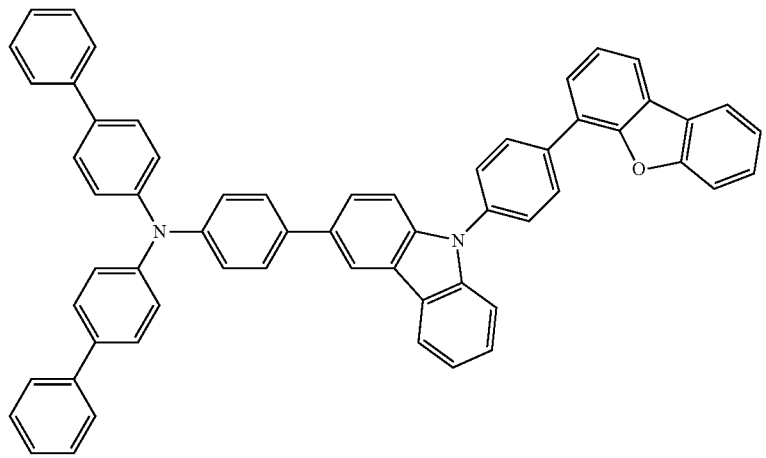

H10

Synthesis Example 11

Production of Aromatic Amine Derivative (H11)

The reaction of Synthesis Example 1 was repeated except for using 6.4 g of the intermediate 2-10 in place of the intermediate 2-1 to obtain 3.8 g of white crystal, which was identified as the following aromatic amine derivative (H11) by FD-MS (yield: 47%).

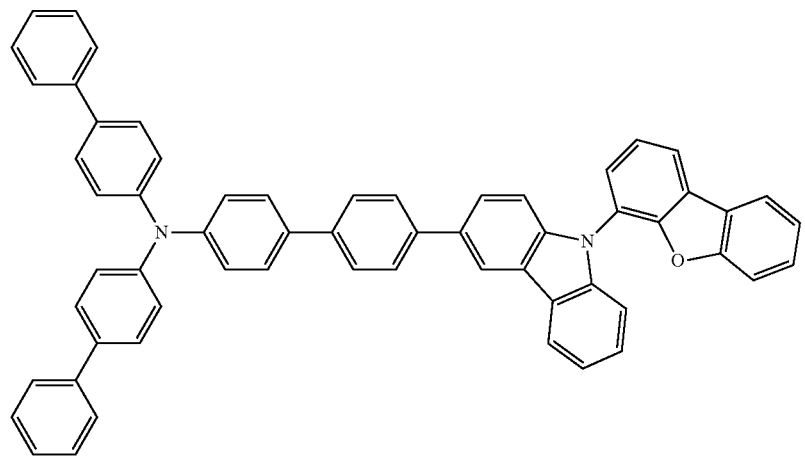

H11

Synthesis Example 12

Production of Aromatic Amine Derivative (H12)

The reaction of Synthesis Example 1 was repeated except for using 6.8 g of the intermediate 2-12 in place of the intermediate 2-1 to obtain 3.4 g of white crystal, which was identified as the following aromatic amine derivative (H12) by FD-MS (yield: 40%).

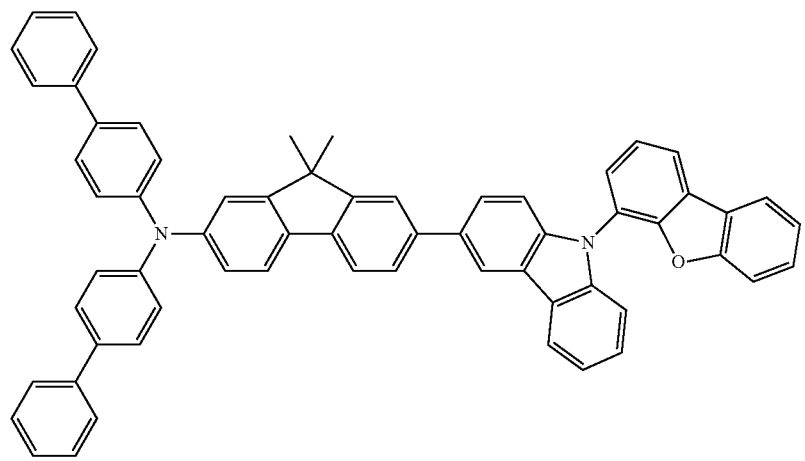

H12

Synthesis Example 13

Production of Aromatic Amine Derivative (H13)

The reaction of Synthesis Example 1 was repeated except for using 2.5 g of the intermediate 1-5 in place of the intermediate 1-3 and 5.6 g of the intermediate 2-3 in place of the intermediate 2-1 to obtain 3.6 g of white crystal, which was identified as the following aromatic amine derivative (H13) by FD-MS (yield: 50%).

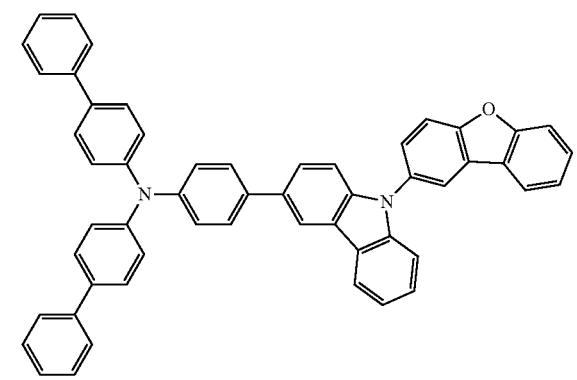

H13

Synthesis Example 14

Production of Aromatic Amine Derivative (H14)

The reaction of Synthesis Example 1 was repeated except for using 5.6 g of the intermediate 2-5 in place of the intermediate 2-1 to obtain 2.9 g of white crystal, which was identified as the following aromatic amine derivative (H14) by FD-MS (yield: 40%).

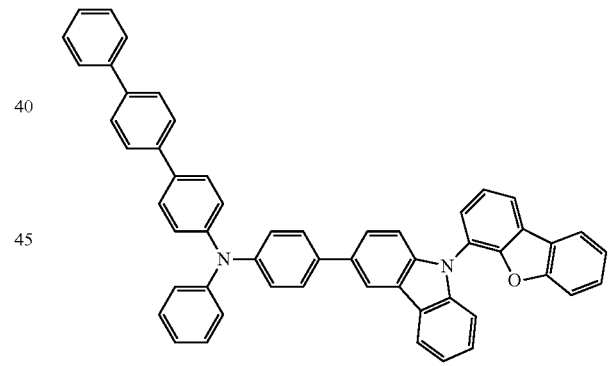

H14

Synthesis Example 15

Production of Aromatic Amine Derivative (H15)

The reaction of Synthesis Example 1 was repeated except for using 3.2 g of the intermediate 1-4 in place of the intermediate 1-3 and 5.6 g of the intermediate 2-5 in place of the intermediate 2-1 to obtain 3.6 g of white crystal, which was identified as the following aromatic amine derivative (H15) by FD-MS (yield: 45%).

H15

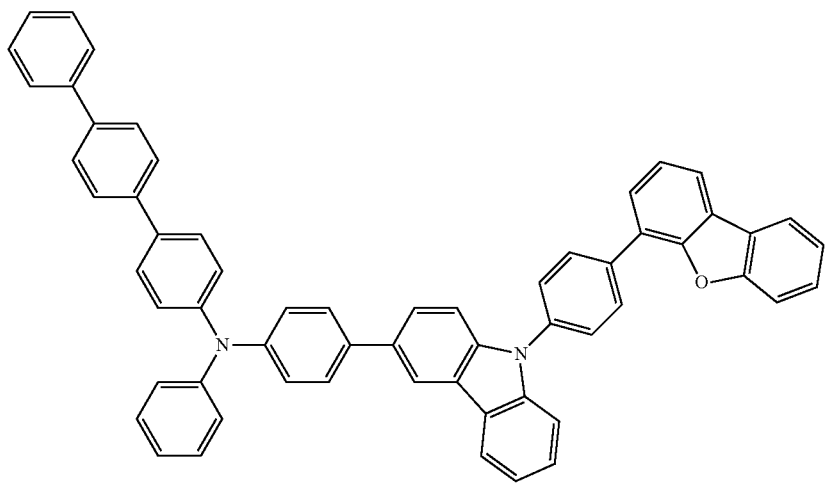

Synthesis Example 16

Production of Aromatic Amine Derivative (H16)

The reaction of Synthesis Example 1 was repeated except for using 6.0 g of the intermediate 2-7 in place of the intermediate 2-1 to obtain 3.8 g of white crystal, which was identified as the following aromatic amine derivative (H16) by FD-MS (yield: 50%).

H16

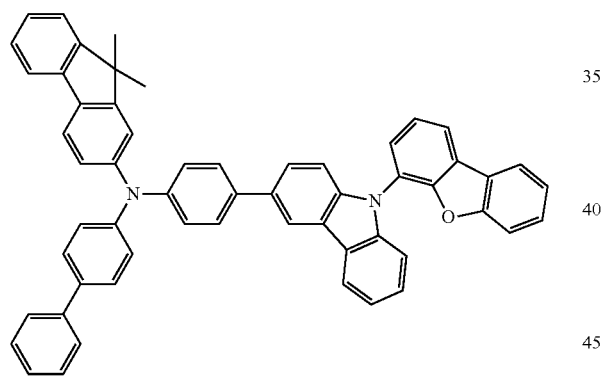

Synthesis Example 17

Production of Aromatic Amine Derivative (H17)

The reaction of Synthesis Example 1 was repeated except for using 3.2 g of the intermediate 1-4 in place of the intermediate 1-3 and 6.0 g of the intermediate 2-7 in place of the intermediate 2-1 to obtain 5.1 g of white crystal, which was identified as the following aromatic amine derivative (H17) by FD-MS (yield: 60%).

H17

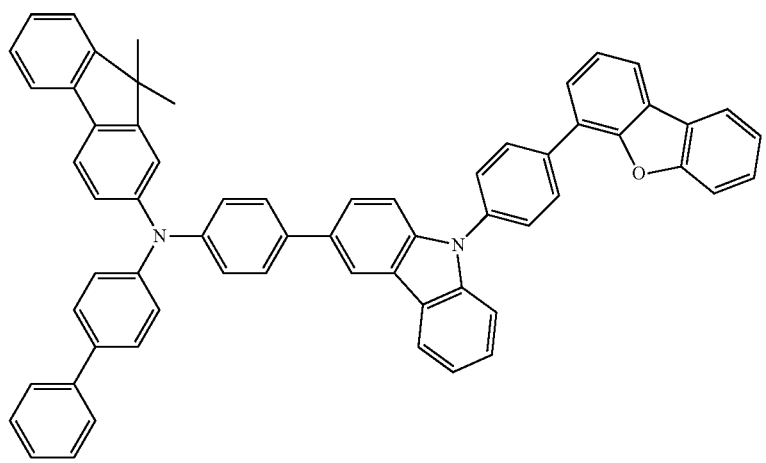

Synthesis Example 18

Production of Aromatic Amine Derivative (H18)

The reaction of Synthesis Example 1 was repeated except for using 2.6 g of the intermediate 1-6 in place of the intermediate 1-3 and 5.6 g of the intermediate 2-3 in place of the intermediate 2-1 to obtain 2.8 g of white crystal, which was identified as the following aromatic amine derivative (H18) by FD-MS (yield: 38%).

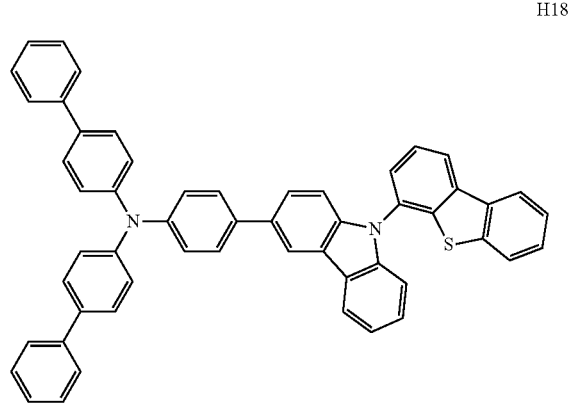 [SMILES: c1ccc(-c2ccc(N(c3ccc(-c4ccccc4)cc3)c3ccc(-c4ccc5c(c4)c4ccccc4n5-c4cccc5c4oc4ccccc45)cc3)cc2)cc1]

H18

Synthesis Example 19

Production of Aromatic Amine Derivative (H19)

The reaction of Synthesis Example 1 was repeated except for using 2.6 g of 2-bromodibenzothiophene in place of the intermediate 1-3 and 5.6 g of the intermediate 2-3 in place of the intermediate 2-1 to obtain 3.8 g of white crystal, which was identified as the following aromatic amine derivative (H19) by FD-MS (yield: 50%).

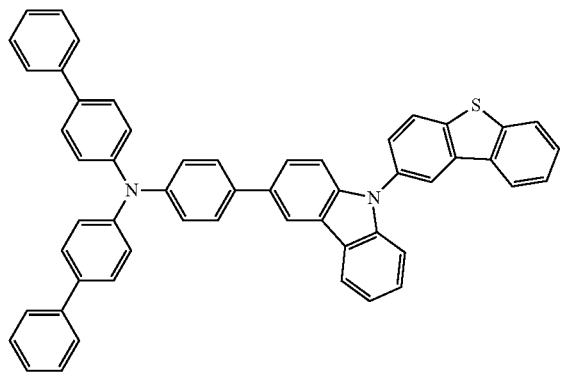

H19

Example 1

Production of Organic EL Device

A glass substrate with an ITO transparent electrode having a size of 25 mm×75 mm×1.1 mm (manufactured by GEOMATEC Co., Ltd.) was ultrasonically cleaned in isopropyl alcohol for 5 min and then UV (ultraviolet)/ozone cleaned for 30 min.

The cleaned glass substrate with the transparent electrode line was mounted on the substrate holder of a vacuum deposition apparatus. First, the following acceptor compound (A) was vapor-deposited onto the surface on the side where the transparent electrode line was formed so as to cover the transparent electrode, thereby forming an acceptor film having a thickness of 5 nm. On the acceptor film, the following aromatic amine derivative (X1) as a first hole transporting material was vapor-deposited to form a first hole transporting layer having a thickness of 120 nm. Successively after forming the first hole transporting layer, the aromatic amine derivative (H6) obtained in Synthesis Example 6 as a second hole transporting material was vapor-deposited to form a second hole transporting layer having a thickness of 47 nm.

On the hole transporting layer, the compound (B) (host for phosphorescence) and $Ir(ppy)_3$ (dopant for phosphorescence) were vapor co-deposited into a film having a thickness of 40 nm, to form a phosphorescent emitting layer. The concentration of $Ir(ppy)_3$ was 10% by mass.

Then, a film of the compound (C) having a thickness of 20 nm, a film of LiF having a thickness of 1 nm, and a film of metallic Al having a thickness of 80 nm were successively deposited to form a cathode. The LiF film as the electron injecting electrode was formed at a film-forming speed of 1 Å/min.

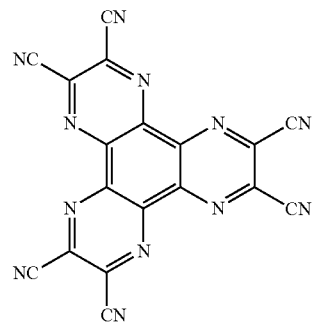

(A)

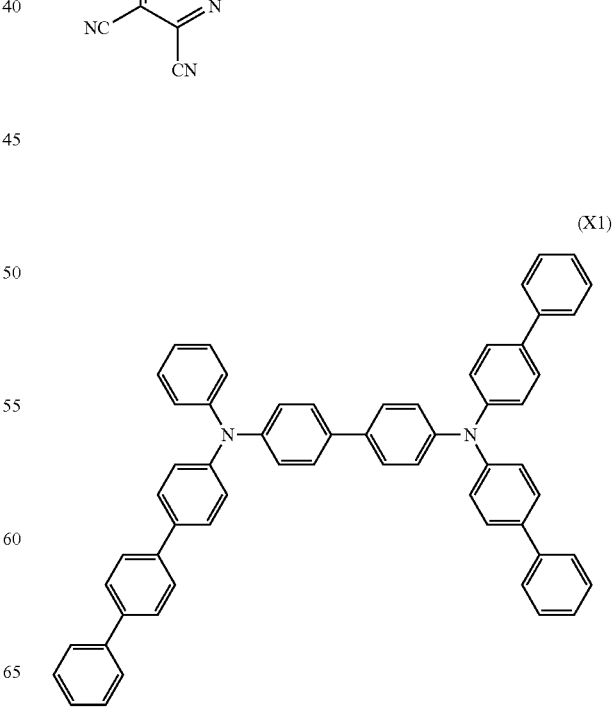

(X1)

-continued (B) 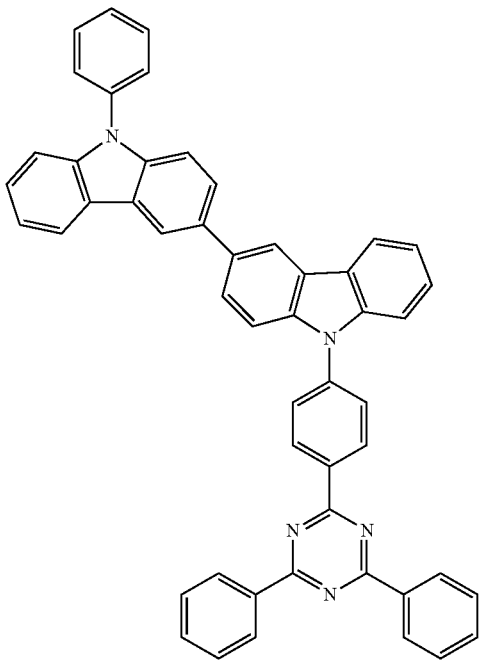

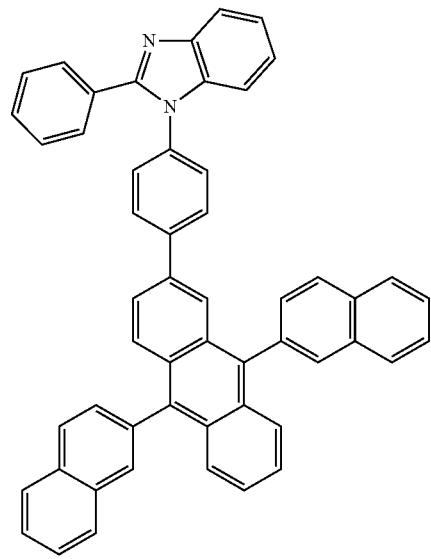
Ir(ppy)₃

Evaluation of Emission Performance of Organic EL Device

The organic EL device thus produced was measured for the luminance (L) and the current density by allowing the device to emit light under a direct current drive, thereby determining the current efficiency (L/J) and the driving voltage (V) at a current density of 10 mA/cm². In addition, the organic EL device was measured for the lifetime at an initial luminance of 20000 cd/m². The 80% lifetime is the time taken until the luminance is reduced to 80% of the initial luminance when driving at a constant current, i.e., the time taken until the luminance is reduced from the initial luminance of 20000 cd/m² to 16000 cd/m². The results are shown in Table 1.

Examples 2 to 14

Each organic EL device was produced in the same manner as in Example 1 except for using each aromatic amine derivative listed in Table 1 as the second hole transporting material in place of the aromatic amine derivative (H6). Each of the obtained organic EL devices was measured for the luminance (L) and the current density by allowing the device to emit light under a direct current drive, thereby determining the current efficiency (L/J) and the driving voltage (V) at a current density of 10 mA/cm². In addition, each organic EL device was measured for the lifetime at an initial luminance of 20000 cd/m². The results are shown in Table 1.

Comparative Examples 1 to 4

Each organic EL device was produced in the same manner as in Example 1 except for using each of the following comparative compounds 1 to 4 as the second hole transporting material in place of the aromatic amine derivative (H6). Each of the obtained organic EL devices was measured for the luminance (L) and the current density by allowing the device to emit light under a direct current drive, thereby determining the current efficiency (L/J) and the driving voltage (V) at a current density of 10 mA/cm². In addition, each organic EL device was measured for the lifetime at an initial luminance of 20000 cd/m². The results are shown in Table 1.

(C)

Comparative compound 1

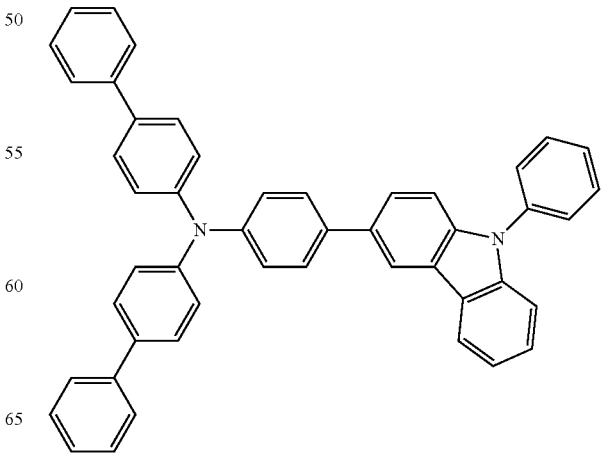

-continued

Comparative compound 2

Comparative compound 3

Comparative compound 4

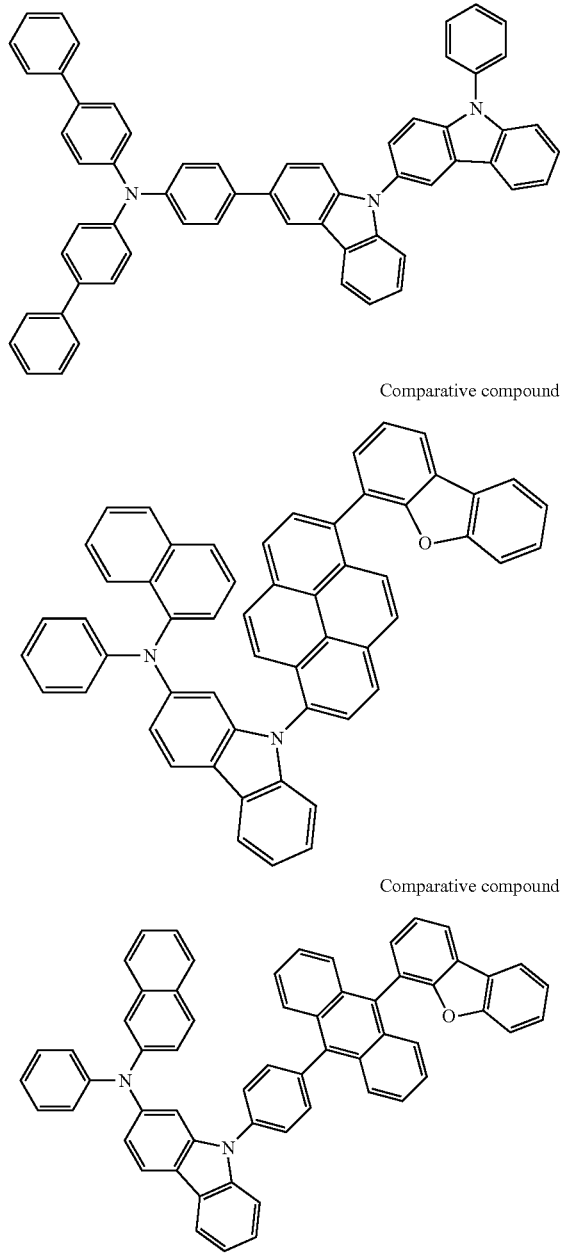

TABLE 1

|  | Second hole transporting material | Results | | |
|---|---|---|---|---|
|  |  | Emission efficiency (cd/A) @ 10 mA/cm² | Driving voltage (V) @ 10 mA/cm² | 80% Lifetime (h) |
| Examples | | | | |
| 1 | H6 | 62.7 | 4.3 | 120 |
| 2 | H7 | 61.2 | 4.2 | 105 |
| 3 | H8 | 62.0 | 4.2 | 110 |
| 4 | H9 | 62.5 | 4.3 | 140 |
| 5 | H10 | 60.5 | 4.2 | 120 |
| 6 | H11 | 62.0 | 4.2 | 130 |

TABLE 1-continued

|  | Second hole transporting material | Results | | |
|---|---|---|---|---|
|  |  | Emission efficiency (cd/A) @ 10 mA/cm² | Driving voltage (V) @ 10 mA/cm² | 80% Lifetime (h) |
| 7 | H12 | 62.2 | 4.1 | 110 |
| 8 | H13 | 61.0 | 4.0 | 120 |
| 9 | H14 | 60.0 | 4.2 | 145 |
| 10 | H15 | 58.4 | 4.1 | 130 |
| 11 | H16 | 62.3 | 4.1 | 110 |
| 12 | H17 | 60.3 | 4.0 | 105 |
| 13 | H18 | 62.3 | 4.3 | 135 |
| 14 | H19 | 61.3 | 4.0 | 130 |
| Comparative Examples | | | | |
| 1 | comparative compound 1 | 55.5 | 4.2 | 105 |
| 2 | comparative compound 2 | 60.3 | 4.0 | 30 |
| 3 | comparative compound 3 | 31.3 | 4.1 | 40 |
| 4 | comparative compound 4 | 33.7 | 4.1 | 40 |

Upon comparing Examples 2, 5, 10, and 12 with Comparative Examples 3 and 4, it can be found that the aromatic amine derivative represented by formula (1) is excellent in the emission efficiency, because the conjugated system at the linker represented by $L_2$ (for example, phenylene group) is narrow to make the difference between LUMO and HOMO large, i.e., make the energy gap large. Upon comparing Examples 1 and 2, Examples 5 and 9, and Examples 11 to 12, it can be further found that a single bond is preferable to a phenylene group as the linker represented by $L_2$.

Upon comparing Examples 4 and 8 with Examples 13 and 14, it can be found that the structure represented by formula (a) bonded via 4-position is preferred as compared with that bonded via 2-position.

INDUSTRIAL APPLICABILITY

As mentioned above in detail, the aromatic amine derivative of the invention is useful as the material for realizing an organic EL device which has a long lifetime and is capable of driving with high efficiency.

What is claimed is:
1. An aromatic amine derivative of formula (1):

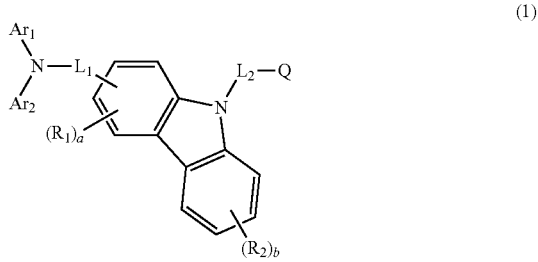

wherein:
$L_1$ is a single bond, a substituted or unsubstituted arylene group having 6 to 30 ring carbon atoms, or a substituted or unsubstituted heteroarylene group having 5 to 30 ring carbon atoms;
$L_2$ is a single bond, a substituted or unsubstituted heteroarylene group having 5 to 30 ring carbon atoms, or a substituted or unsubstituted arylene group, wherein the arylene group is selected from a phenylene group, a biphenylene group, a terphenylene group, a naphthylene group, a phenanthrylene group, a chrysenylene group, a perylenylene group, and a fluorenylene group;

each of $Ar_1$ and $Ar_2$ are independently a substituted or unsubstituted aryl group having 6 to 30 ring carbon atoms or a substituted or unsubstituted heteroaryl group having 5 to 30 ring carbon atoms;

each of $R_1$ and $R_2$ are independently a fluorine atom, a cyano group, a substituted or unsubstituted alkyl group having 1 to 20 carbon atoms, a substituted or unsubstituted cycloalkyl group having 3 to 20 carbon atoms, a substituted or unsubstituted alkoxy group having 1 to 20 carbon atoms, a substituted or unsubstituted haloalkyl group having 1 to 20 carbon atoms, a substituted or unsubstituted haloalkoxy group having 1 to 20 carbon atoms, a substituted or unsubstituted alkylsilyl group having 1 to 10 carbon atoms, a substituted or unsubstituted arylsilyl group having 6 to 30 carbon atoms, a substituted or unsubstituted aralkyl group having 7 to 30 carbon atoms, a substituted or unsubstituted aryl group having 6 to 30 ring carbon atoms, or a substituted or unsubstituted heteroaryl group having 5 to 30 ring carbon atoms, wherein adjacent $R_1$ groups and adjacent $R_2$ groups may be respectively bonded to each other to form a ring structure together with ring carbon atoms of the benzene ring;

the optional substituent of each substituted or unsubstituted group is selected from the group consisting of a fluorine atom, a cyano group, an alkyl group having 1 to 20 carbon atoms, a cycloalkyl group having 3 to 20 carbon atoms, an alkoxy group having 1 to 20 carbon atoms, a haloalkyl group having 1 to 20 carbon atoms, a haloalkoxy group having 1 to 20 carbon atoms, an alkylsilyl group having 1 to 10 carbon atoms, an aryl group having 6 to 30 ring carbon atoms, an aryloxy group having 6 to 30 ring carbon atoms, an arylsilyl group having 6 to 30 carbon atoms, an aralkyl group having 7 to 30 carbon atoms, and a heteroaryl group having 5 to 30 ring atoms;

a is an integer of 0 to 3;
b is an integer of 0 to 4; and
Q is a group of formula (a):

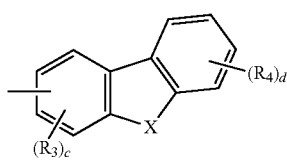

wherein:
X is an oxygen atom or a sulfur atom;
each of $R_3$ and $R_4$ are independently a fluorine atom, a cyano group, a substituted or unsubstituted alkyl group having 1 to 20 carbon atoms, a substituted or unsubstituted cycloalkyl group having 3 to 20 carbon atoms, a substituted or unsubstituted alkoxy group having 1 to 20 carbon atoms, a substituted or unsubstituted haloalkyl group having 1 to 20 carbon atoms, a substituted or unsubstituted haloalkoxy group having 1 to 20 carbon atoms, a substituted or unsubstituted alkylsilyl group having 1 to 10 carbon atoms, a substituted or unsubstituted arylsilyl group having 6 to 30 carbon atoms, a substituted or unsubstituted aralkyl group having 7 to 30 carbon atoms, a substituted or unsubstituted aryl group having 6 to 30 ring carbon atoms, or a substituted or unsubstituted heteroaryl group having 5 to 30 ring carbon atoms, wherein adjacent $R_3$ groups and adjacent $R_4$ groups may be respectively bonded to each other to form a ring structure together with ring carbon atoms of the benzene ring;

c is an integer of 0 to 3; and
d is an integer of 0 to 4.

2. The aromatic amine derivative according to claim 1, wherein the aromatic amine derivative is of formula (1-1):

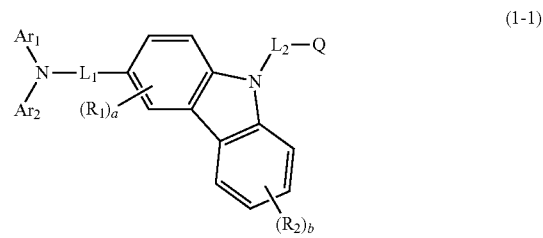

wherein $L_1$, $L_2$, $Ar_1$, $Ar_2$, $R_1$, $R_2$, a, b, and Q are as defined in formula (1).

3. The aromatic amine derivative according to claim 1, wherein Q is of formula (a-1):

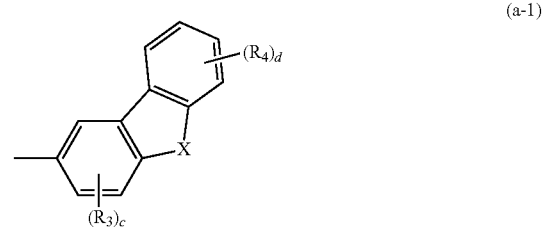

wherein $R_3$, $R_4$, c, d, and X are as defined in formula (a).

4. The aromatic amine derivative according to claim 1, wherein Q is of formula (a-2):

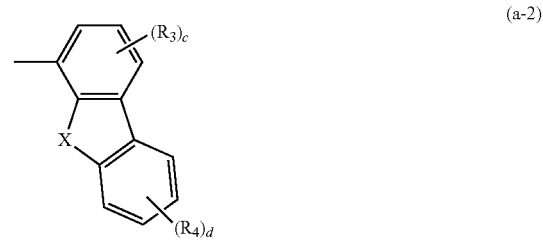

wherein $R_3$, $R_4$, c, d, and X are as defined in formula (a).

5. The aromatic amine derivative according to claim 1, wherein at least one of $L_1$ and $L_2$ is a single bond or a linking group of any one of formulae (b-1) to (b-3):

-continued (b-2)

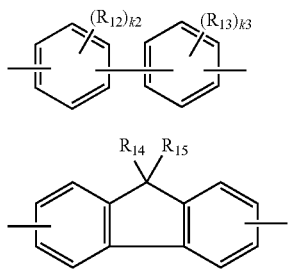

(b-3)

wherein:
each of $R_{11}$ to $R_{13}$ are independently a fluorine atom, a cyano group, a substituted or unsubstituted alkyl group having 1 to 20 carbon atoms, a substituted or unsubstituted cycloalkyl group having 3 to 20 carbon atoms, a substituted or unsubstituted alkoxy group having 1 to 20 carbon atoms, a substituted or unsubstituted haloalkyl group having 1 to 20 carbon atoms, a substituted or unsubstituted haloalkoxy group having 1 to 20 carbon atoms, a substituted or unsubstituted alkylsilyl group having 1 to 10 carbon atoms, a substituted or unsubstituted arylsilyl group having 6 to 30 carbon atoms, a substituted or unsubstituted aralkyl group having 7 to 30 carbon atoms, a substituted or unsubstituted aryl group having 6 to 30 ring carbon atoms, or a substituted or unsubstituted heteroaryl group having 5 to 30 ring carbon atoms, wherein adjacent $R_{11}$ groups, adjacent $R_{12}$ groups, and adjacent $R_{13}$ groups may be respectively bonded to each other to form a ring structure together with ring carbon atoms of the benzene ring;
each of $R_{14}$ and $R_{15}$ are independently a hydrogen atom, a substituted or unsubstituted alkyl group having 1 to 20 carbon atoms, a substituted or unsubstituted cycloalkyl group having 3 to 20 carbon atoms, a substituted or unsubstituted haloalkyl group having 1 to 20 carbon atoms, a substituted or unsubstituted aralkyl group having 7 to 30 carbon atoms, a substituted or unsubstituted aryl group having 6 to 30 ring carbon atoms, or a substituted or unsubstituted heteroaryl group having 5 to 30 ring carbon atoms; and
each of $k_1$ to $k_3$ are independently an integer of 0 to 4.

6. The aromatic amine derivative according to claim 5, wherein $L_1$ is a linking group of any one of formulae (b-1) to (b-3).

7. The aromatic amine derivative according to claim 5, wherein $L_2$ is a single bond or a linking group of any one of formulae (b-1) to (b-3).

8. The aromatic amine derivative according to claim 7, wherein $L_2$ is a single bond or a linking group of formula (b-1).

9. The aromatic amine derivative according to claim 1, wherein X is an oxygen atom.

10. The aromatic amine derivative according to claim 1, wherein X is a sulfur atom.

11. A material, comprising the aromatic amine derivative according to claim 1.

12. The material according to claim 11, wherein the material is a hole transporting material.

13. An organic electroluminescence device comprising an anode, a cathode, and an organic thin film layer between the anode and the cathode, wherein the organic thin film layer comprise a light emitting layer and a layer of the organic thin film layer comprises the aromatic amine derivative according to claim 1.

14. The organic electroluminescence device according to claim 13, wherein the organic thin film layer comprises a hole transporting layer and the hole transporting layer comprises the aromatic amine derivative.

15. The organic electroluminescence device according to claim 14, wherein a layer comprising an acceptor material is disposed in contact with the hole transporting layer.

16. The organic electroluminescence device according to claim 15, wherein the acceptor material is of formula (10):

(10)

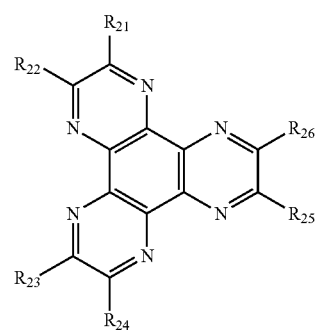

wherein each of $R_{21}$ to $R_{26}$ are independently a cyano group, —$CONH_2$, a carboxyl group, or —$COOR_{27}$, wherein $R_{27}$ is an alkyl group having 1 to 20 carbon atoms or a cycloalkyl group having 3 to 20 carbon atoms, and at least one pair selected from the group consisting of $R_{21}$ and $R_{22}$, $R_{23}$ and $R_{24}$, and $R_{25}$ and $R_{26}$ may be respectively bonded to each other to form a group —CO—O—CO—.

17. The organic electroluminescence device according to claim 13, wherein the light emitting layer comprises a phosphorescent emitting material.

18. The organic electroluminescence device according to claim 17, wherein the phosphorescent emitting material is an ortho metallated complex of at least one metal selected from the group consisting of iridium (Ir), osmium (Os) and platinum (Pt).

* * * * *